(12) United States Patent
Galetto

(10) Patent No.: US 11,919,961 B2
(45) Date of Patent: *Mar. 5, 2024

(54) CD123 SPECIFIC CHIMERIC ANTIGEN RECEPTORS FOR CANCER IMMUNOTHERAPY

(71) Applicant: CELLECTIS, Paris (FR)

(72) Inventor: Roman Galetto, Paris (FR)

(73) Assignee: CELLECTIS, Paris (FR)

( * ) Notice: Subject to any disclaimer, the term of this patent is extended or adjusted under 35 U.S.C. 154(b) by 492 days.

This patent is subject to a terminal disclaimer.

(21) Appl. No.: 17/124,971

(22) Filed: Dec. 17, 2020

(65) Prior Publication Data

US 2021/0163612 A1    Jun. 3, 2021

Related U.S. Application Data

(63) Continuation of application No. 15/925,182, filed on Mar. 19, 2018, now Pat. No. 10,988,541, which is a continuation of application No. 15/126,540, filed as application No. PCT/EP2015/000558 on Mar. 19, 2015, now Pat. No. 9,944,709.

(30) Foreign Application Priority Data

Mar. 19, 2014   (DK) .............................. PA201470137

(51) Int. Cl.
C07K 16/28     (2006.01)
A61K 39/00     (2006.01)
C07K 14/725    (2006.01)

(52) U.S. Cl.
CPC ...... C07K 16/2866 (2013.01); C07K 14/7051 (2013.01); A61K 2039/505 (2013.01); C07K 2317/24 (2013.01); C07K 2317/565 (2013.01); C07K 2317/62 (2013.01); C07K 2317/622 (2013.01); C07K 2319/03 (2013.01); C07K 2319/30 (2013.01)

(58) Field of Classification Search
CPC ............ C07K 14/7051; C07K 16/2866; C07K 16/00–468; A61K 39/395–39558; A61K 35/17; A61K 39/46–4631; A61K 39/464416
See application file for complete search history.

(56) References Cited

U.S. PATENT DOCUMENTS

| 9,944,709 B2 | 4/2018 | Galetto |
| 10,239,948 B2 | 3/2019 | Juillerat et al. |
| 10,988,541 B2 * | 4/2021 | Galetto ................ A61P 35/02 |
| 2007/0036773 A1 | 2/2007 | Cooper et al. |
| 2012/0060230 A1 | 3/2012 | Collingwood et al. |
| 2012/0328619 A1 | 12/2012 | Fey et al. |
| 2013/0315884 A1 | 11/2013 | Galetto et al. |
| 2014/0271582 A1 | 9/2014 | Forman et al. |
| 2014/0271635 A1 | 9/2014 | Brogdon et al. |
| 2014/0322212 A1 | 10/2014 | Brogdon et al. |
| 2017/0296623 A1 | 10/2017 | Juillerat et al. |

FOREIGN PATENT DOCUMENTS

| CN | 102762594 A | 10/2012 |
| CN | 103492406 A | 1/2014 |
| EP | 2332994 A1 | 6/2011 |
| JP | 2014-507118 | 3/2014 |
| JP | 2015-513920 | 5/2015 |
| JP | 2016-514457 | 5/2016 |
| WO | WO 2012/079000 A1 | 6/2012 |
| WO | WO 2013/123061 A1 | 8/2013 |
| WO | WO 2015/193406 A1 | 12/2015 |
| WO | WO 2016/097231 A2 | 6/2016 |
| WO | WO 2016/120220 A1 | 8/2016 |

OTHER PUBLICATIONS

Mannioui et al., "Treatment of B cells malignancies with anti-CD19 CAR+, TCR−, CD52-allogeneic T cells," 2013 *Journal for Immuno Therapy of Cancer* 1(Suppl 1): P34.
Poirot et al., "T-Cell Engineering For "off-The-shelf" Adoptive Immunotherapy," 2013 *American Society of Hematology* 122(21): 1661.
Galetto et al., "Pre-T cell receptor for improved expansion of TCR alpha disrupted T cells," 2013 *Journal for Immuno Therapy of Cancer* 1 (Suppl 1): P9.
Dutour et al., "In Vitro and In Vivo Antitumor Effect of Anti-CD33 Chimeric Receptor-Expressing EBV-CTL against CD33+ Acute Myeloid Leukemia," 2012 *Advances in Hematology*1 10 pages.
Marin et al., "Cytokine-induced killer cells for cell therapy of acute myeloid leukemia: improvement of their immune activity by expression of CD33-specific chimeric receptors," 2010 *hematologica* 95(12), 2144-2152.
O'Hear et al., "Anti-CD33 Chimeric Antigen Receptor Therapy For Acute Myeloid Leukemia," 2013 *American Society of Hematology* 122(21) 1441.
O'Hear et al., "Anti-CD33 chimeric antigen receptor targeting of acute myeloid leukemia," 2015 *hematologica* 100(3).
Sadelain et al., "The promise and potential pitfalls of chimeric antigen receptors," 2009 *Curr Opin Immunol.* 21(2): 215-223.

(Continued)

*Primary Examiner* — Jessica H Roark

(74) *Attorney, Agent, or Firm* — Casimir Jones, S.C.; Peter J. Schlueter

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a CD123 monoclonal antibody, conferring specific immunity against CD123 positive cells. The engineered immune cells endowed with such CARs are particularly suited for treating lymphomas and leukemia.

21 Claims, 15 Drawing Sheets

Specification includes a Sequence Listing.

(56) References Cited

OTHER PUBLICATIONS

Maus et al., "Antibody-modified T cells: CARs take the front seat for hematologic malignancies," 2014 *Blood* 123:17.
Schwemmlein et al., "A CD33-specific single-chain immunotoxin mediates potent apoptosis of cultured human myeloid leukaemia cells," 2006 *British Journal of Hematology* 133, 141-151.
Herrmann et al., "CD34+/CD38− stem cells in chronic myeloid leukemia express Siglec-3 (CD33) and are responsive to the CD33-targeting drug gemtuzumab/ozogamicin," 2012 *haematologica* 97(2).
De Lima et al., "Phase I/II study of gemtuzumab ozogamicin added to fludarabine, melphalan and allogeneic hematopoietic stem cell transplantation for high-risk CD33 positive myeloid leukemias and myelodysplastic syndrome," 2008 *Leukemia* 22, 258-264.
Sahara et al., "Clinicopathological and prognostic characteristics of CD33-positive multiple myeloma," 2006 *Eur J Haematol.* 77(1): 14-8.
Imai et al., "Chimeric receptors with 4-1BB signaling capacity provoke potent cytoxicity against acute lymphoblastic leukemia," 2004 *Leukemia* 18, 676-684.
Milone et al., "Chimeric Receptors Containing CD137 Signal Transduction Domains Mediate Enhanced Survival of T Cells and Increased Antileukemic Efficacy In Vivo," 2009 *Molecular Therapy* 17(8), 1453-1464.
Campana et al., "4-1BB Chimeric Antigen Receptors," 2014 *The Cancer Journal* 20(2).
Rillahan et al., "Disubstituted Sialic Acid Ligands Targeting Siglecs CD33 and CD22 Associated with Myeloid Leukaemias and B Cell Lymphomas," 2014 *Chem Sci.* 5(6), 2398-2406.
Collins English Dictionary, 1991 Third Ed., p. 774.
Wikipedia, "Methotrexate," Accessed on Nov. 5, 2020, 9 pages.
*Molecular Therapy* 21(Suppl 1), 2013, S154.
Mejstrikova et al., "Correlation of CD33 with poorer prognosis in childhood ALL implicates a potential of anti-CD33 frontline therapy," 2005 *Leukemia* 19, 1092-1094.
Ferrari et al., "CD33 is expressed on plasma cells of a significant number of myeloma patients, and may represent a therapeutic target," 2005 *Leukemia* 19, 2021-2022.
Wikipedia, "CD3 (immunology)," Accessed on Mar. 6, 2020, 3 pages.
Response to the Notice of Opposition filed Apr. 25, 2018, 9 pages.
Cruse at al., "Illustrated Dictionary of Immunology," 2003, 2$^{nd}$ ed., 270, 514.
Mardiros et al., "T cells expressing CD123-specific chimeric antigen receptors exhibit specific cytolytic effector functions and anti-tumor effects against human acute myeloid leukemia," 2013, *Blood* 122:18, 3138-3148.
Pizzitola et al., "Chimeric antigen receptors against CD33/CD123 antigens efficiently target primary acute myeloid leukemia cells in vivo," 2014, *Leukemia* 28, 1596-1605.

Rudikoff, et al., "Single amino acid substitution altering antigen-binding specificity," 1982, *Proc. Nat. Acad. Sci. USA.* Immunology 79: abstract on p. 1979.
Torikai et al., "A foundation for universal T-cell based immunotherapy: T cells engineered to express a CD19-specific chimeric-antigen-receptor and eliminate expression of endogenous TCR," 2012, *Blood* 119:24, 5697-5705.
Tsumoto, Kohei, "Antigen-antibody interaction analysis for antibody development," 2013, *Drug Delivery System* 28:5, 412-423.
Yarlin, A.A., "Osnovy immunologii," 1999, 172-174.
Zhong et al., "Chimeric Antigen Receptors Combining 4-1BB and CD28 Signaling Domains Augment PI3kinase/AKT/Bcl-XI Activation and CD8+ T Cell-mediated Tumor Eradication," 2010, *The American Society of Gene & Cell Therapy* 18:2, 413-420.
Almagro & Fransson, Frontiers in Bioscience 2008; 13: 1619-33.
Brown et al., J. Immunol. 1996; 156(9): 3285-91.
Bueno et al., haematologica 2004; 89: 58-69.
Campana et al., "4-1BB Chimeric Antigen Receptors," The Cancer Journal, vol. 20, Mar./Apr. 2014, pp. 134-140.
Gill et al., "Preclinical targeting of human acute myeloid leukemia and myeloablation using chimeric antigen receptor-modified T cells," Blood, vol. 123, Apr. 2014, pp. 2343-2354.
Han et al., J. Hematol. Oncol. 2013; 6:47, pp. 1-7.
International Search Report issued in International Patent Application No. PCT/EP2015/055848 dated Jun. 25, 2015.
JR Fromm, Cytometry Part B 2011; 80B: 91-99.
Kenderian et al., Cancer Res. 2014; 74: 6383-9.
Mardiros et al., "T cells expressing CD123-specific chimeric antigen receptors exhibit specific cytolytic effector functions and anti-tumor effects against human acute myeloid leukemia," Blood, vol. 122, Oct. 2013, pp. 3138-3148.
Milone et al., "Chimeric Receptors Containing CD137 Signal Transduction Domains Mediate Enhanced Survival of T Cells and Increased Antileukemic Efficacy in Vivo," Molecular Therapy, vol. 17, Aug. 2009, pp. 1453-1464.
Morgan et al., "Case Report of a Serious Adverse Event Following the Administration of T Cells Transduced With a Chimeric Antigen Receptor Recognizing ERBB2," Molecular Therapy, vol. 18, 2010, pp. 843-851.
Munoz et al., haematologica 2001; 86: 1261-69.
Pizzitola et al., "Chimeric antigen receptors against CD33/CD123 antigens efficiently target primary acute myeloid leukemia cells in vivo," Leukemia, 2014, pp. 1-10.
PJ Carter, Nat. Rev. Immunol. 2006; 6:343-57.
Reichert & Valge-Archer, Nat. Rev. Drug. Disc. 2007:6: 349-56.
Rudikoff et al., Proc. Nat'l Acad. Sci. USA 1982; 79: 1979-83.
Silwkowski et al., Science 2013; 341: 1192-98.
Testa et al., Biomarker Res. 2014; 2:4, pp. 1-11.
Tettamanti et al., "Targeting of acute myeloid leukaemia by cytokine-induced killer cells redirected with a novel CD123-specific chimeric antigen receptor," British Journal of Haematology, vol. 161, 2013, pp. 389-401.
Venkataraman et al., Am. J. Clin. Pathol. 2011; 136: 625-30.

\* cited by examiner

| Day post TD | Klon43-v3 | | 32716-v3 | |
| --- | --- | --- | --- | --- |
| | CAR | BFP | CAR | BFP |
| Donor 1, day 8 | 89% | 98% | 91% | 96% |
| Donor 2, day 10 | 93% | 94% | 88% | 88% |

SEQUENCE LISTING

<160> NUMBER OF SEQ ID NOS: 77

<210> SEQ ID NO 1
<211> LENGTH: 20
<212> TYPE: PRT
<213> ORGANISM: artificial sequence
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 21
<212> TYPE: PRT
<213> ORGANISM: artificial sequence
<220> FEATURE:
<223> OTHER INFORMATION: signal peptide

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 16
<212> TYPE: PRT
<213> ORGANISM: homo sapiens
<220> FEATURE:
<221> NAME/KEY: misc_feature
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
<220> FEATURE:

```
<221> NAME/KEY: misc_feature
<223> OTHER INFORMATION: Fragment of T-cell surface glycoprotein CD8
      alpha chain isoform 1 precursor (residues 138-206)

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
                35                  40                  45

<210> SEQ ID NO 5
<211> LENGTH: 231
<212> TYPE: PRT
<213> ORGANISM: homo sapiens
<220> FEATURE:
<221> NAME/KEY: misc_feature
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
                35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<221> NAME/KEY: misc_feature
<223> OTHER INFORMATION: CD8alpha transmembrane domain
```

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<221> NAME/KEY: misc_feature
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<221> NAME/KEY: misc_feature
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 9
<211> LENGTH: 112
<212> TYPE: PRT
<213> ORGANISM: homo sapiens
<220> FEATURE:
<221> NAME/KEY: misc_feature
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 10
<211> LENGTH: 15
<212> TYPE: PRT
<213> ORGANISM: artificial sequence
<220> FEATURE:
<223> OTHER INFORMATION: linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 141
<212> TYPE: PRT
<213> ORGANISM: artificial sequence
<220> FEATURE:
<223> OTHER INFORMATION: 7G3 heavy chain variable region

<400> SEQUENCE: 11

Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
                85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser
    130                 135                 140

<210> SEQ ID NO 12
<211> LENGTH: 134
<212> TYPE: PRT
<213> ORGANISM: artificial sequence
<220> FEATURE:
<223> OTHER INFORMATION: 7G3 light chain variable region

<400> SEQUENCE: 12

Met Glu Ser Gln Thr Gln Val Leu Met Ser Leu Leu Phe Trp Val Ser
1               5                   10                  15

Gly Thr Cys Gly Asp Phe Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Leu Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
```

100             105             110

Tyr Cys Gln Asn Asp Tyr Ser Tyr Pro Tyr Thr Phe Gly Gly Gly Thr
        115                 120                 125

Lys Leu Glu Ile Lys Arg
    130

<210> SEQ ID NO 13
<211> LENGTH: 140
<212> TYPE: PRT
<213> ORGANISM: artificial sequence
<220> FEATURE:
<223> OTHER INFORMATION: Old4 heavy chain variable region

<400> SEQUENCE: 13

Trp Thr Trp Arg Phe Leu Phe Val Val Ala Ala Ala Thr Gly Val Gln
1               5                   10                  15

Ser Gln Val Gln Leu Leu Gln Ser Gly Ala Glu Val Lys Lys Pro Gly
            20                  25                  30

Ser Ser Val Lys Val Ser Cys Lys Ala Ser Gly Gly Thr Phe Ser Thr
        35                  40                  45

Tyr Ala Ile Ser Trp Val Arg Gln Ala Pro Gly Gln Gly Leu Glu Trp
    50                  55                  60

Met Gly Gly Ile Ile Pro Ile Phe Gly Ile Val Asn Tyr Ala Gln Lys
65                  70                  75                  80

Phe Gln Gly Arg Val Thr Ile Thr Ala Asp Glu Ser Thr Ser Thr Ala
                85                  90                  95

Tyr Met Glu Leu Ser Ser Leu Arg Ser Glu Asp Thr Ala Val Tyr Tyr
            100                 105                 110

Cys Ala Arg Gly Gly Gly Ser Gly Pro Asp Val Leu Asp Ile Trp Gly
        115                 120                 125

Gln Gly Thr Met Val Thr Val Ser Ser Ala Ser Thr
    130                 135                 140

<210> SEQ ID NO 14
<211> LENGTH: 132
<212> TYPE: PRT
<213> ORGANISM: artificial sequence
<220> FEATURE:
<223> OTHER INFORMATION: Old4 light chain variable region

<400> SEQUENCE: 14

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
        35                  40                  45

Gln Gly Ile Arg Ser Tyr Leu Ala Trp Tyr Gln Gln Lys Pro Gly Lys
    50                  55                  60

Ala Pro Glu Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Ser Glu Asp Phe Ala Thr Tyr Tyr Cys Gln Gln
            100                 105                 110

Tyr Tyr Ser Phe Pro Tyr Thr Phe Gly Gln Gly Thr Lys Leu Glu Ile
        115                 120                 125

```
Lys Arg Thr Val
        130

<210> SEQ ID NO 15
<211> LENGTH: 115
<212> TYPE: PRT
<213> ORGANISM: artificial sequence
<220> FEATURE:
<223> OTHER INFORMATION: 26292 heavy chain variable region

<400> SEQUENCE: 15

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser
        115

<210> SEQ ID NO 16
<211> LENGTH: 107
<212> TYPE: PRT
<213> ORGANISM: artificial sequence
<220> FEATURE:
<223> OTHER INFORMATION: 26292 light chain variable region

<400> SEQUENCE: 16

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys
            100                 105

<210> SEQ ID NO 17
<211> LENGTH: 118
<212> TYPE: PRT
<213> ORGANISM: artificial sequence
<220> FEATURE:
<223> OTHER INFORMATION: 32716 heavy chain variable region

<400> SEQUENCE: 17

Gln Ile Gln Leu Val Gln Ser Gly Pro Glu Leu Lys Lys Pro Gly Glu
```

```
                1               5                  10                 15
        Thr Val Lys Ile Ser Cys Lys Ala Ser Gly Tyr Ile Phe Thr Asn Tyr
                        20                  25                 30
        Gly Met Asn Trp Val Lys Gln Ala Pro Gly Lys Ser Phe Lys Trp Met
                    35                  40                 45
        Gly Trp Ile Asn Thr Tyr Thr Gly Glu Ser Thr Tyr Ser Ala Asp Phe
             50                  55                  60
        Lys Gly Arg Phe Ala Phe Ser Leu Glu Thr Ser Ala Ser Thr Ala Tyr
        65                   70                  75                  80
        Leu His Ile Asn Asp Leu Lys Asn Glu Asp Thr Ala Thr Tyr Phe Cys
                            85                  90                  95
        Ala Arg Ser Gly Gly Tyr Asp Pro Met Asp Tyr Trp Gly Gln Gly Thr
                        100                 105                110
        Ser Val Thr Val Ser Ser
                    115

<210> SEQ ID NO 18
<211> LENGTH: 111
<212> TYPE: PRT
<213> ORGANISM: artificial sequence
<220> FEATURE:
<223> OTHER INFORMATION: 32716 light chain variable region

<400> SEQUENCE: 18

Asp Ile Val Leu Thr Gln Ser Pro Ala Ser Leu Ala Val Ser Leu Gly
        1               5                  10                 15
        Gln Arg Ala Thr Ile Ser Cys Arg Ala Ser Glu Ser Val Asp Asn Tyr
                        20                  25                 30
        Gly Asn Thr Phe Met His Trp Tyr Gln Gln Lys Pro Gly Gln Pro Pro
                    35                  40                 45
        Lys Leu Leu Ile Tyr Arg Ala Ser Asn Leu Glu Ser Gly Ile Pro Ala
             50                  55                  60
        Arg Phe Ser Gly Ser Gly Ser Arg Thr Asp Phe Thr Leu Thr Ile Asn
        65                   70                  75                  80
        Pro Val Glu Ala Asp Asp Val Ala Thr Tyr Tyr Cys Gln Gln Ser Asn
                            85                  90                  95
        Glu Asp Pro Pro Thr Phe Gly Ala Gly Thr Lys Leu Glu Leu Lys
                        100                 105                110

<210> SEQ ID NO 19
<211> LENGTH: 113
<212> TYPE: PRT
<213> ORGANISM: artificial sequence
<220> FEATURE:
<223> OTHER INFORMATION: Klon43 light chain variable region

<400> SEQUENCE: 19

Met Ala Asp Tyr Lys Asp Ile Val Met Thr Gln Ser His Lys Phe Met
        1               5                  10                 15
        Ser Thr Ser Val Gly Asp Arg Val Asn Ile Thr Cys Lys Ala Ser Gln
                        20                  25                 30
        Asn Val Asp Ser Ala Val Ala Trp Tyr Gln Gln Lys Pro Gly Gln Ser
                    35                  40                 45
        Pro Lys Ala Leu Ile Tyr Ser Ala Ser Tyr Arg Tyr Ser Gly Val Pro
             50                  55                  60
        Asp Arg Phe Thr Gly Arg Gly Ser Gly Thr Asp Phe Thr Leu Thr Ile
        65                   70                  75                  80
```

```
Ser Ser Val Gln Ala Glu Asp Leu Ala Val Tyr Tyr Cys Gln Gln Tyr
            85                  90                  95

Tyr Ser Thr Pro Trp Thr Phe Gly Gly Gly Thr Lys Leu Glu Ile Lys
            100                 105                 110

Arg

<210> SEQ ID NO 20
<211> LENGTH: 127
<212> TYPE: PRT
<213> ORGANISM: artificial sequence
<220> FEATURE:
<223> OTHER INFORMATION: Klon43 heavy chain variable region

<400> SEQUENCE: 20

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
            35                  40                  45

Ala Leu Ile Arg Ser Lys Ala Asp Gly Tyr Thr Thr Glu Tyr Ser Ala
50                  55                  60

Ser Val Lys Gly Arg Phe Thr Leu Ser Arg Asp Asp Ser Gln Ser Ile
65                  70                  75                  80

Leu Tyr Leu Gln Met Asn Ala Leu Arg Pro Glu Asp Ser Ala Thr Tyr
            85                  90                  95

Tyr Cys Ala Arg Asp Ala Ala Tyr Tyr Ser Tyr Ser Tyr Pro Glu Gly
            100                 105                 110

Ala Met Asp Tyr Trp Gly Gln Gly Thr Ser Val Thr Val Ser Ser
            115                 120                 125

<210> SEQ ID NO 21
<211> LENGTH: 119
<212> TYPE: PRT
<213> ORGANISM: artificial sequence
<220> FEATURE:
<223> OTHER INFORMATION: 12F1 heavy chain variable region

<400> SEQUENCE: 21

Val Gln Leu Gln Glu Ser Gly Pro Gly Leu Val Lys Pro Ser Gln Ser
1               5                   10                  15

Leu Ser Leu Thr Cys Ser Val Thr Asp Tyr Ser Ile Thr Ser Gly Tyr
            20                  25                  30

Tyr Trp Asn Trp Ile Arg Gln Phe Pro Gly Asn Lys Leu Glu Trp Met
            35                  40                  45

Gly Tyr Ile Ser Tyr Asp Gly Ser Asn Asn Tyr Asn Pro Ser Leu Lys
50                  55                  60

Asn Arg Ile Ser Ile Thr Arg Asp Thr Ser Lys Asn Gln Phe Phe Leu
65                  70                  75                  80

Lys Leu Ser Ser Val Thr Thr Glu Asp Thr Ala Thr Tyr Tyr Cys Ser
            85                  90                  95

Arg Gly Glu Gly Phe Tyr Phe Asp Ser Trp Gly Gln Gly Thr Thr Leu
            100                 105                 110

Thr Val Ser Ser Ala Arg Ser
            115

<210> SEQ ID NO 22
<211> LENGTH: 113
```

```
<212> TYPE: PRT
<213> ORGANISM: artificial sequence
<220> FEATURE:
<223> OTHER INFORMATION: 12F1 light chain variable region

<400> SEQUENCE: 22

Asp Ile Met Met Ser Gln Ser Pro Ser Ser Leu Ala Val Ser Val Gly
1               5                   10                  15

Glu Lys Phe Thr Met Thr Cys Lys Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys

<210> SEQ ID NO 23
<211> LENGTH: 484
<212> TYPE: PRT
<213> ORGANISM: artificial sequence
<220> FEATURE:
<223> OTHER INFORMATION: 7GR-1 polypeptide CAR sequence

<400> SEQUENCE: 23

Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
                85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser Gly Gly Gly
    130                 135                 140

Gly Ser Gly Gly Gly Ser Gly Gly Gly Ser Met Glu Ser Gln
145                 150                 155                 160

Thr Gln Val Leu Met Ser Leu Leu Phe Trp Val Ser Gly Thr Cys Gly
                165                 170                 175

Asp Phe Val Met Thr Gln Ser Pro Ser Ser Leu Thr Val Thr Ala Gly
            180                 185                 190

Glu Lys Val Thr Met Ser Cys Lys Ser Ser Gln Ser Leu Leu Asn Ser
        195                 200                 205
```

```
Gly Asn Gln Lys Asn Tyr Leu Thr Trp Tyr Leu Gln Lys Pro Gly Gln
    210                 215                 220

Pro Pro Lys Leu Leu Ile Tyr Trp Ala Ser Thr Arg Glu Ser Gly Val
225                 230                 235                 240

Pro Asp Arg Phe Thr Gly Ser Gly Ser Gly Thr Asp Phe Thr Leu Thr
                245                 250                 255

Ile Ser Ser Val Gln Ala Glu Asp Leu Ala Val Tyr Tyr Cys Gln Asn
                260                 265                 270

Asp Tyr Ser Tyr Pro Tyr Thr Phe Gly Gly Gly Thr Lys Leu Glu Ile
            275                 280                 285

Lys Arg Gly Leu Ala Val Ser Thr Ile Ser Ser Phe Phe Pro Pro Gly
    290                 295                 300

Tyr Gln Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
    355                 360                 365

Gly Cys Glu Leu Arg Val Lys Phe Ser Arg Ser Ala Asp Ala Pro Ala
370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
                420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 24
<211> LENGTH: 487
<212> TYPE: PRT
<213> ORGANISM: artificial sequence
<220> FEATURE:
<223> OTHER INFORMATION: 7GR-2 polypeptide CAR sequence

<400> SEQUENCE: 24

Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
                20                  25                  30

Pro Gly Ala Ser Val Lys Met Ser Cys Lys Ala Ser Gly Tyr Thr Phe
            35                  40                  45

Thr Asp Tyr Tyr Met Lys Trp Val Lys Gln Ser His Gly Lys Ser Leu
        50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
```

```
                    85                  90                  95
Thr Ala Tyr Met His Leu Asn Ser Leu Thr Ser Glu Asp Ser Ala Val
                100                 105                 110

Tyr Tyr Cys Thr Arg Ser His Leu Leu Arg Ala Ser Trp Phe Ala Tyr
                115                 120                 125

Trp Gly Gln Gly Thr Leu Val Thr Val Ser Ala Ala Ser Gly Gly Gly
        130                 135                 140

Gly Ser Gly Gly Gly Ser Gly Gly Gly Ser Met Glu Ser Gln
145                 150                 155                 160

Thr Gln Val Leu Met Ser Leu Leu Phe Trp Val Ser Gly Thr Cys Gly
                165                 170                 175

Asp Phe Val Met Thr Gln Ser Pro Ser Ser Leu Thr Val Thr Ala Gly
                180                 185                 190

Glu Lys Val Thr Met Ser Cys Lys Ser Ser Gln Ser Leu Leu Asn Ser
                195                 200                 205

Gly Asn Gln Lys Asn Tyr Leu Thr Trp Tyr Leu Gln Lys Pro Gly Gln
        210                 215                 220

Pro Pro Lys Leu Leu Ile Tyr Trp Ala Ser Thr Arg Glu Ser Gly Val
225                 230                 235                 240

Pro Asp Arg Phe Thr Gly Ser Gly Ser Gly Thr Asp Phe Thr Leu Thr
                245                 250                 255

Ile Ser Ser Val Gln Ala Glu Asp Leu Ala Val Tyr Tyr Cys Gln Asn
                260                 265                 270

Asp Tyr Ser Tyr Pro Tyr Thr Phe Gly Gly Gly Thr Lys Leu Glu Ile
                275                 280                 285

Lys Arg Gly Leu Ala Val Ser Thr Ile Ser Ser Phe Phe Pro Pro Gly
        290                 295                 300

Tyr Gln Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
                370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 25
```

<211> LENGTH: 513
<212> TYPE: PRT
<213> ORGANISM: artificial sequence
<220> FEATURE:
<223> OTHER INFORMATION: 7GR-3 polypeptide CAR sequence

<400> SEQUENCE: 25

```
Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
                85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser Gly Gly Gly
130                 135                 140

Gly Ser Gly Gly Gly Gly Ser Gly Gly Gly Gly Ser Met Glu Ser Gln
145                 150                 155                 160

Thr Gln Val Leu Met Ser Leu Leu Phe Trp Val Ser Gly Thr Cys Gly
                165                 170                 175

Asp Phe Val Met Thr Gln Ser Pro Ser Ser Leu Thr Val Thr Ala Gly
            180                 185                 190

Glu Lys Val Thr Met Ser Cys Lys Ser Ser Gln Ser Leu Leu Asn Ser
        195                 200                 205

Gly Asn Gln Lys Asn Tyr Leu Thr Trp Tyr Leu Gln Lys Pro Gly Gln
    210                 215                 220

Pro Pro Lys Leu Leu Ile Tyr Trp Ala Ser Thr Arg Glu Ser Gly Val
225                 230                 235                 240

Pro Asp Arg Phe Thr Gly Ser Gly Ser Gly Thr Asp Phe Thr Leu Thr
                245                 250                 255

Ile Ser Ser Val Gln Ala Glu Asp Leu Ala Val Tyr Tyr Cys Gln Asn
            260                 265                 270

Asp Tyr Ser Tyr Pro Tyr Thr Phe Gly Gly Gly Thr Lys Leu Glu Ile
        275                 280                 285

Lys Arg Thr Thr Thr Pro Ala Pro Arg Pro Pro Thr Pro Ala Pro Thr
    290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Tyr Ile Trp Ala Pro Leu Ala Gly Thr Cys Gly Val Leu Leu Leu Ser
            340                 345                 350

Leu Val Ile Thr Leu Tyr Cys Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380
```

```
Asp Gly Cys Ser Cys Arg Phe Pro Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
            500                 505                 510

Arg
```

<210> SEQ ID NO 26
<211> LENGTH: 516
<212> TYPE: PRT
<213> ORGANISM: artificial sequence
<220> FEATURE:
<223> OTHER INFORMATION: 7GR-4 polypeptide CAR sequence

<400> SEQUENCE: 26

```
Met Gly Trp Ser Trp Ile Phe Leu Phe Leu Val Ser Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
                85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser Gly Gly Gly
    130                 135                 140

Gly Ser Gly Gly Gly Ser Gly Gly Gly Ser Met Glu Ser Gln
145                 150                 155                 160

Thr Gln Val Leu Met Ser Leu Leu Phe Trp Val Ser Gly Thr Cys Gly
                165                 170                 175

Asp Phe Val Met Thr Gln Ser Pro Ser Ser Leu Thr Val Thr Ala Gly
            180                 185                 190

Glu Lys Val Thr Met Ser Cys Lys Ser Ser Gln Ser Leu Leu Asn Ser
        195                 200                 205

Gly Asn Gln Lys Asn Tyr Leu Thr Trp Tyr Leu Gln Lys Pro Gly Gln
    210                 215                 220
```

Pro Pro Lys Leu Leu Ile Tyr Trp Ala Ser Thr Arg Glu Ser Gly Val
225                 230                 235                 240

Pro Asp Arg Phe Thr Gly Ser Gly Ser Gly Thr Asp Phe Thr Leu Thr
            245                 250                 255

Ile Ser Ser Val Gln Ala Glu Asp Leu Ala Val Tyr Tyr Cys Gln Asn
        260                 265                 270

Asp Tyr Ser Tyr Pro Tyr Thr Phe Gly Gly Gly Thr Lys Leu Glu Ile
    275                 280                 285

Lys Arg Thr Thr Thr Pro Ala Pro Arg Pro Pro Thr Pro Ala Pro Thr
290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Ile Ser Phe Phe Leu Ala Leu Thr Ser Thr Ala Leu Leu Phe Leu Leu
            340                 345                 350

Phe Phe Leu Thr Leu Arg Phe Ser Val Val Lys Arg Gly Arg Lys Lys
        355                 360                 365

Leu Leu Tyr Ile Phe Lys Gln Pro Phe Met Arg Pro Val Gln Thr Thr
370                 375                 380

Gln Glu Glu Asp Gly Cys Ser Cys Arg Phe Pro Glu Glu Glu Glu Gly
385                 390                 395                 400

Gly Cys Glu Leu Arg Val Lys Phe Ser Arg Ser Ala Asp Ala Pro Ala
                405                 410                 415

Tyr Gln Gln Gly Gln Asn Gln Leu Tyr Asn Glu Leu Asn Leu Gly Arg
            420                 425                 430

Arg Glu Glu Tyr Asp Val Leu Asp Lys Arg Arg Gly Arg Asp Pro Glu
        435                 440                 445

Met Gly Gly Lys Pro Arg Arg Lys Asn Pro Gln Glu Gly Leu Tyr Asn
450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
                485                 490                 495

Leu Ser Thr Ala Thr Lys Asp Thr Tyr Asp Ala Leu His Met Gln Ala
            500                 505                 510

Leu Pro Pro Arg
        515

<210> SEQ ID NO 27
<211> LENGTH: 699
<212> TYPE: PRT
<213> ORGANISM: artificial sequence
<220> FEATURE:
<223> OTHER INFORMATION: 7GR-5 polypeptide CAR sequence

<400> SEQUENCE: 27

Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

-continued

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
            85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser Gly Gly Gly
    130                 135                 140

Gly Ser Gly Gly Gly Gly Ser Gly Gly Gly Gly Ser Met Glu Ser Gln
145                 150                 155                 160

Thr Gln Val Leu Met Ser Leu Leu Phe Trp Val Ser Gly Thr Cys Gly
            165                 170                 175

Asp Phe Val Met Thr Gln Ser Pro Ser Ser Leu Thr Val Thr Ala Gly
            180                 185                 190

Glu Lys Val Thr Met Ser Cys Lys Ser Ser Gln Ser Leu Leu Asn Ser
            195                 200                 205

Gly Asn Gln Lys Asn Tyr Leu Thr Trp Tyr Leu Gln Lys Pro Gly Gln
210                 215                 220

Pro Pro Lys Leu Leu Ile Tyr Trp Ala Ser Thr Arg Glu Ser Gly Val
225                 230                 235                 240

Pro Asp Arg Phe Thr Gly Ser Gly Ser Gly Thr Asp Phe Thr Leu Thr
                245                 250                 255

Ile Ser Ser Val Gln Ala Glu Asp Leu Ala Val Tyr Tyr Cys Gln Asn
            260                 265                 270

Asp Tyr Ser Tyr Pro Tyr Thr Phe Gly Gly Gly Thr Lys Leu Glu Ile
        275                 280                 285

Lys Arg Glu Pro Lys Ser Pro Asp Lys Thr His Thr Cys Pro Pro Cys
    290                 295                 300

Pro Ala Pro Pro Val Ala Gly Pro Ser Val Phe Leu Phe Pro Pro Lys
305                 310                 315                 320

Pro Lys Asp Thr Leu Met Ile Ala Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
        355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
            420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
    450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val

```
                485                 490                 495
Phe Ser Cys Ser Val Met His Glu Ala Leu His Asn His Tyr Thr Gln
                500                 505                 510

Lys Ser Leu Ser Leu Ser Pro Gly Lys Ile Tyr Ile Trp Ala Pro Leu
            515                 520                 525

Ala Gly Thr Cys Gly Val Leu Leu Leu Ser Leu Val Ile Thr Leu Tyr
        530                 535                 540

Cys Lys Arg Gly Arg Lys Lys Leu Leu Tyr Ile Phe Lys Gln Pro Phe
545                 550                 555                 560

Met Arg Pro Val Gln Thr Thr Gln Glu Glu Asp Gly Cys Ser Cys Arg
                565                 570                 575

Phe Pro Glu Glu Glu Glu Gly Gly Cys Glu Leu Arg Val Lys Phe Ser
                580                 585                 590

Arg Ser Ala Asp Ala Pro Ala Tyr Gln Gln Gly Gln Asn Gln Leu Tyr
            595                 600                 605

Asn Glu Leu Asn Leu Gly Arg Arg Glu Glu Tyr Asp Val Leu Asp Lys
        610                 615                 620

Arg Arg Gly Arg Asp Pro Glu Met Gly Gly Lys Pro Arg Arg Lys Asn
625                 630                 635                 640

Pro Gln Glu Gly Leu Tyr Asn Glu Leu Gln Lys Asp Lys Met Ala Glu
                645                 650                 655

Ala Tyr Ser Glu Ile Gly Met Lys Gly Glu Arg Arg Arg Gly Lys Gly
                660                 665                 670

His Asp Gly Leu Tyr Gln Gly Leu Ser Thr Ala Thr Lys Asp Thr Tyr
            675                 680                 685

Asp Ala Leu His Met Gln Ala Leu Pro Pro Arg
        690                 695

<210> SEQ ID NO 28
<211> LENGTH: 702
<212> TYPE: PRT
<213> ORGANISM: artificial sequence
<220> FEATURE:
<223> OTHER INFORMATION: 7GR-6 polypeptide CAR sequence

<400> SEQUENCE: 28

Met Gly Trp Ser Trp Ile Phe Leu Phe Leu Val Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Ile Pro Ser Asn Gly Ala Thr Phe Tyr Asn
65                  70                  75                  80

Gln Lys Phe Lys Gly Lys Ala Thr Leu Thr Val Asp Arg Ser Ser Ser
                85                  90                  95

Thr Ala Tyr Met His Leu Asn Ser Leu Thr Ser Glu Asp Ser Ala Val
            100                 105                 110

Tyr Tyr Cys Thr Arg Ser His Leu Leu Arg Ala Ser Trp Phe Ala Tyr
        115                 120                 125

Trp Gly Gln Gly Thr Leu Val Thr Val Ser Ala Ala Ser Gly Gly Gly
    130                 135                 140

Gly Ser Gly Gly Gly Gly Ser Gly Gly Gly Gly Ser Met Glu Ser Gln
```

```
            145                 150                 155                 160
        Thr Gln Val Leu Met Ser Leu Leu Phe Trp Val Ser Gly Thr Cys Gly
                            165                 170                 175
        Asp Phe Val Met Thr Gln Ser Pro Ser Ser Leu Thr Val Thr Ala Gly
                            180                 185                 190
        Glu Lys Val Thr Met Ser Cys Lys Ser Ser Gln Ser Leu Leu Asn Ser
                            195                 200                 205
        Gly Asn Gln Lys Asn Tyr Leu Thr Trp Tyr Leu Gln Lys Pro Gly Gln
                            210                 215                 220
        Pro Pro Lys Leu Leu Ile Tyr Trp Ala Ser Thr Arg Glu Ser Gly Val
        225                 230                 235                 240
        Pro Asp Arg Phe Thr Gly Ser Gly Ser Gly Thr Asp Phe Thr Leu Thr
                            245                 250                 255
        Ile Ser Ser Val Gln Ala Glu Asp Leu Ala Val Tyr Tyr Cys Gln Asn
                            260                 265                 270
        Asp Tyr Ser Tyr Pro Tyr Thr Phe Gly Gly Gly Thr Lys Leu Glu Ile
                            275                 280                 285
        Lys Arg Glu Pro Lys Ser Pro Asp Lys Thr His Thr Cys Pro Pro Cys
                            290                 295                 300
        Pro Ala Pro Pro Val Ala Gly Pro Ser Val Phe Leu Phe Pro Pro Lys
        305                 310                 315                 320
        Pro Lys Asp Thr Leu Met Ile Ala Arg Thr Pro Glu Val Thr Cys Val
                            325                 330                 335
        Val Val Asp Val Ser His Glu Asp Pro Glu Val Lys Phe Asn Trp Tyr
                            340                 345                 350
        Val Asp Gly Val Glu Val His Asn Ala Lys Thr Lys Pro Arg Glu Glu
                            355                 360                 365
        Gln Tyr Asn Ser Thr Tyr Arg Val Val Ser Val Leu Thr Val Leu His
                            370                 375                 380
        Gln Asp Trp Leu Asn Gly Lys Glu Tyr Lys Cys Lys Val Ser Asn Lys
        385                 390                 395                 400
        Ala Leu Pro Ala Pro Ile Glu Lys Thr Ile Ser Lys Ala Lys Gly Gln
                            405                 410                 415
        Pro Arg Glu Pro Gln Val Tyr Thr Leu Pro Pro Ser Arg Asp Glu Leu
                            420                 425                 430
        Thr Lys Asn Gln Val Ser Leu Thr Cys Leu Val Lys Gly Phe Tyr Pro
                            435                 440                 445
        Ser Asp Ile Ala Val Glu Trp Glu Ser Asn Gly Gln Pro Glu Asn Asn
        450                 455                 460
        Tyr Lys Thr Thr Pro Pro Val Leu Asp Ser Asp Gly Ser Phe Phe Leu
        465                 470                 475                 480
        Tyr Ser Lys Leu Thr Val Asp Lys Ser Arg Trp Gln Gln Gly Asn Val
                            485                 490                 495
        Phe Ser Cys Ser Val Met His Glu Ala Leu His Asn His Tyr Thr Gln
                            500                 505                 510
        Lys Ser Leu Ser Leu Ser Pro Gly Lys Ile Ile Ser Phe Phe Leu Ala
                            515                 520                 525
        Leu Thr Ser Thr Ala Leu Leu Phe Leu Leu Phe Leu Thr Leu Arg
                            530                 535                 540
        Phe Ser Val Val Lys Arg Gly Arg Lys Lys Leu Leu Tyr Ile Phe Lys
        545                 550                 555                 560
        Gln Pro Phe Met Arg Pro Val Gln Thr Thr Gln Glu Glu Asp Gly Cys
                            565                 570                 575
```

```
Ser Cys Arg Phe Pro Glu Glu Glu Gly Gly Cys Glu Leu Arg Val
            580                 585                 590

Lys Phe Ser Arg Ser Ala Asp Ala Pro Ala Tyr Gln Gln Gly Gln Asn
        595                 600                 605

Gln Leu Tyr Asn Glu Leu Asn Leu Gly Arg Arg Glu Gly Tyr Asp Val
    610                 615                 620

Leu Asp Lys Arg Arg Gly Arg Asp Pro Glu Met Gly Gly Lys Pro Arg
625                 630                 635                 640

Arg Lys Asn Pro Gln Glu Gly Leu Tyr Asn Glu Leu Gln Lys Asp Lys
                645                 650                 655

Met Ala Glu Ala Tyr Ser Glu Ile Gly Met Lys Gly Glu Arg Arg Arg
            660                 665                 670

Gly Lys Gly His Asp Gly Leu Tyr Gln Gly Leu Ser Thr Ala Thr Lys
        675                 680                 685

Asp Thr Tyr Asp Ala Leu His Met Gln Ala Leu Pro Pro Arg
    690                 695                 700
```

<210> SEQ ID NO 29
<211> LENGTH: 510
<212> TYPE: PRT
<213> ORGANISM: artificial sequence
<220> FEATURE:
<223> OTHER INFORMATION: Old4-3 polypeptide CAR sequence

<400> SEQUENCE: 29

```
Trp Thr Trp Arg Phe Leu Phe Val Val Ala Ala Ala Thr Gly Val Gln
1               5                   10                  15

Ser Gln Val Gln Leu Leu Gln Ser Gly Ala Glu Val Lys Lys Pro Gly
                20                  25                  30

Ser Ser Val Lys Val Ser Cys Lys Ala Ser Gly Gly Thr Phe Ser Thr
            35                  40                  45

Tyr Ala Ile Ser Trp Val Arg Gln Ala Pro Gly Gln Gly Leu Glu Trp
        50                  55                  60

Met Gly Gly Ile Ile Pro Ile Phe Gly Ile Val Asn Tyr Ala Gln Lys
65              70                  75                  80

Phe Gln Gly Arg Val Thr Ile Thr Ala Asp Glu Ser Thr Ser Thr Ala
                85                  90                  95

Tyr Met Glu Leu Ser Ser Leu Arg Ser Glu Asp Thr Ala Val Tyr Tyr
            100                 105                 110

Cys Ala Arg Gly Gly Gly Ser Gly Pro Asp Val Leu Asp Ile Trp Gly
        115                 120                 125

Gln Gly Thr Met Val Thr Val Ser Ser Ala Ser Thr Gly Gly Gly Gly
    130                 135                 140

Ser Gly Gly Gly Gly Ser Gly Gly Gly Ser Met Asp Met Arg Val
145                 150                 155                 160

Pro Ala Gln Leu Leu Gly Leu Leu Leu Leu Trp Leu Pro Gly Ala Arg
                165                 170                 175

Cys Val Ile Trp Met Thr Gln Ser Pro Ser Leu Leu Ser Ala Ser Thr
            180                 185                 190

Gly Asp Arg Val Thr Ile Ser Cys Arg Met Ser Gln Gly Ile Arg Ser
        195                 200                 205

Tyr Leu Ala Trp Tyr Gln Gln Lys Pro Gly Lys Ala Pro Glu Leu Leu
    210                 215                 220

Ile Tyr Ala Ala Ser Thr Leu Gln Ser Gly Val Pro Ser Arg Phe Ser
225                 230                 235                 240
```

Gly Ser Gly Ser Gly Thr Asp Phe Thr Leu Thr Ile Ser Ser Leu Gln
            245                 250                 255

Ser Glu Asp Phe Ala Thr Tyr Tyr Cys Gln Gln Tyr Tyr Ser Phe Pro
        260                 265                 270

Tyr Thr Phe Gly Gln Gly Thr Lys Leu Glu Ile Lys Arg Thr Val Thr
    275                 280                 285

Thr Thr Pro Ala Pro Arg Pro Pro Thr Pro Ala Pro Thr Ile Ala Ser
290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 30
<211> LENGTH: 431
<212> TYPE: PRT
<213> ORGANISM: artificial sequence
<220> FEATURE:
<223> OTHER INFORMATION: 26292-1 polypeptide CAR sequence

<400> SEQUENCE: 30

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
                100                 105                 110

Val Ser Ser Gly Gly Gly Ser Gly Gly Gly Ser Gly Gly Gly
        115                 120                 125

Gly Ser Asp Val Gln Ile Thr Gln Ser Pro Ser Tyr Leu Ala Ala Ser
        130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
                180                 185                 190

Ser Gly Ser Gly Ser Gly Thr Asp Phe Thr Leu Thr Ile Ser Ser Leu
                195                 200                 205

Glu Pro Glu Asp Phe Ala Met Tyr Tyr Cys Gln Gln His Asn Lys Tyr
                210                 215                 220

Pro Tyr Thr Phe Gly Gly Gly Thr Lys Leu Glu Ile Lys Gly Leu Ala
225                 230                 235                 240

Val Ser Thr Ile Ser Ser Phe Phe Pro Pro Gly Tyr Gln Ile Tyr Ile
                245                 250                 255

Trp Ala Pro Leu Ala Gly Thr Cys Gly Val Leu Leu Leu Ser Leu Val
                260                 265                 270

Ile Thr Leu Tyr Cys Lys Arg Gly Arg Lys Lys Leu Leu Tyr Ile Phe
                275                 280                 285

Lys Gln Pro Phe Met Arg Pro Val Gln Thr Thr Gln Glu Glu Asp Gly
                290                 295                 300

Cys Ser Cys Arg Phe Pro Glu Glu Glu Gly Gly Cys Glu Leu Arg
305                 310                 315                 320

Val Lys Phe Ser Arg Ser Ala Asp Ala Pro Ala Tyr Gln Gln Gly Gln
                325                 330                 335

Asn Gln Leu Tyr Asn Glu Leu Asn Leu Gly Arg Arg Glu Glu Tyr Asp
                340                 345                 350

Val Leu Asp Lys Arg Arg Gly Arg Asp Pro Glu Met Gly Gly Lys Pro
                355                 360                 365

Arg Arg Lys Asn Pro Gln Glu Gly Leu Tyr Asn Glu Leu Gln Lys Asp
370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
                405                 410                 415

Lys Asp Thr Tyr Asp Ala Leu His Met Gln Ala Leu Pro Pro Arg
                420                 425                 430

<210> SEQ ID NO 31
<211> LENGTH: 434
<212> TYPE: PRT
<213> ORGANISM: artificial sequence
<220> FEATURE:
<223> OTHER INFORMATION: 26292-2 polypeptide CAR sequence

<400> SEQUENCE: 31

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

-continued

```
Trp Met Asn Trp Val Lys Gln Arg Pro Asp Gln Gly Leu Glu Trp Ile
         35                  40                  45

Gly Arg Ile Asp Pro Tyr Asp Ser Glu Thr His Tyr Asn Gln Lys Phe
 50                  55                  60

Lys Asp Lys Ala Ile Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Asn Trp Asp Asp Tyr Trp Gly Gln Gly Thr Thr Leu Thr
                 100                 105                 110

Val Ser Ser Gly Gly Gly Gly Ser Gly Gly Gly Gly Ser Gly Gly Gly
                 115                 120                 125

Gly Ser Asp Val Gln Ile Thr Gln Ser Pro Ser Tyr Leu Ala Ala Ser
        130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                 165                 170                 175

Leu Ile Tyr Ser Gly Ser Thr Leu Gln Ser Gly Ile Pro Ser Arg Phe
                 180                 185                 190

Ser Gly Ser Gly Ser Gly Thr Asp Phe Thr Leu Thr Ile Ser Ser Leu
                 195                 200                 205

Glu Pro Glu Asp Phe Ala Met Tyr Tyr Cys Gln Gln His Asn Lys Tyr
        210                 215                 220

Pro Tyr Thr Phe Gly Gly Gly Thr Lys Leu Glu Ile Lys Gly Leu Ala
225                 230                 235                 240

Val Ser Thr Ile Ser Ser Phe Phe Pro Pro Gly Tyr Gln Ile Ile Ser
                 245                 250                 255

Phe Phe Leu Ala Leu Thr Ser Thr Ala Leu Leu Phe Leu Leu Phe Phe
                 260                 265                 270

Leu Thr Leu Arg Phe Ser Val Val Lys Arg Gly Arg Lys Lys Leu Leu
        275                 280                 285

Tyr Ile Phe Lys Gln Pro Phe Met Arg Pro Val Gln Thr Thr Gln Glu
        290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
                 325                 330                 335

Gln Gly Gln Asn Gln Leu Tyr Asn Glu Leu Asn Leu Gly Arg Arg Glu
                 340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
        370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                 405                 410                 415

Thr Ala Thr Lys Asp Thr Tyr Asp Ala Leu His Met Gln Ala Leu Pro
                 420                 425                 430

Pro Arg
```

```
<210> SEQ ID NO 32
<211> LENGTH: 460
<212> TYPE: PRT
<213> ORGANISM: artificial sequence
<220> FEATURE:
<223> OTHER INFORMATION: 26292-3 polypeptide CAR sequence

<400> SEQUENCE: 32
```

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Val Gln Ile Thr Gln Ser Pro Ser Tyr Leu Ala Ala Ser
    130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
            180                 185                 190

Ser Gly Ser Gly Ser Gly Thr Asp Phe Thr Leu Thr Ile Ser Ser Leu
        195                 200                 205

Glu Pro Glu Asp Phe Ala Met Tyr Tyr Cys Gln Gln His Asn Lys Tyr
    210                 215                 220

Pro Tyr Thr Phe Gly Gly Gly Thr Lys Leu Glu Ile Lys Thr Thr Thr
225                 230                 235                 240

Pro Ala Pro Arg Pro Pro Thr Pro Ala Pro Thr Ile Ala Ser Gln Pro
                245                 250                 255

Leu Ser Leu Arg Pro Glu Ala Cys Arg Pro Ala Ala Gly Gly Ala Val
            260                 265                 270

His Thr Arg Gly Leu Asp Phe Ala Cys Asp Ile Tyr Ile Trp Ala Pro
        275                 280                 285

Leu Ala Gly Thr Cys Gly Val Leu Leu Leu Ser Leu Val Ile Thr Leu
    290                 295                 300

Tyr Cys Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp

```
            370                 375                 380
Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
                420                 425                 430

Gly His Asp Gly Leu Tyr Gln Gly Leu Ser Thr Ala Thr Lys Asp Thr
                435                 440                 445

Tyr Asp Ala Leu His Met Gln Ala Leu Pro Pro Arg
    450                 455                 460

<210> SEQ ID NO 33
<211> LENGTH: 463
<212> TYPE: PRT
<213> ORGANISM: artificial sequence
<220> FEATURE:
<223> OTHER INFORMATION: 26292-4 polypeptide CAR sequence

<400> SEQUENCE: 33

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Met Asn Trp Val Lys Gln Arg Pro Asp Gln Gly Leu Glu Trp Ile
            35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
                100                 105                 110

Val Ser Ser Gly Gly Gly Gly Ser Gly Gly Gly Gly Ser Gly Gly Gly
            115                 120                 125

Gly Ser Asp Val Gln Ile Thr Gln Ser Pro Ser Tyr Leu Ala Ala Ser
    130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
            180                 185                 190

Ser Gly Ser Gly Ser Gly Thr Asp Phe Thr Leu Thr Ile Ser Ser Leu
    195                 200                 205

Glu Pro Glu Asp Phe Ala Met Tyr Tyr Cys Gln Gln His Asn Lys Tyr
210                 215                 220

Pro Tyr Thr Phe Gly Gly Gly Thr Lys Leu Glu Ile Lys Thr Thr Thr
225                 230                 235                 240

Pro Ala Pro Arg Pro Pro Thr Pro Ala Pro Thr Ile Ala Ser Gln Pro
                245                 250                 255

Leu Ser Leu Arg Pro Glu Ala Cys Arg Pro Ala Ala Gly Gly Ala Val
            260                 265                 270

His Thr Arg Gly Leu Asp Phe Ala Cys Asp Ile Ile Ser Phe Phe Leu
```

```
                275                 280                 285
Ala Leu Thr Ser Thr Ala Leu Leu Phe Leu Leu Phe Phe Leu Thr Leu
        290                 295                 300

Arg Phe Ser Val Val Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Gly Gly Cys Glu Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
        370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
450                 455                 460

<210> SEQ ID NO 34
<211> LENGTH: 646
<212> TYPE: PRT
<213> ORGANISM: artificial sequence
<220> FEATURE:
<223> OTHER INFORMATION: 26292-5 polypeptide CAR sequence

<400> SEQUENCE: 34

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Asn Trp Asp Asp Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Val Gln Ile Thr Gln Ser Pro Ser Tyr Leu Ala Ala Ser
    130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
```

```
                180                 185                 190
Ser Gly Ser Gly Ser Gly Thr Asp Phe Thr Leu Thr Ile Ser Ser Leu
            195                 200                 205

Glu Pro Glu Asp Phe Ala Met Tyr Tyr Cys Gln Gln His Asn Lys Tyr
        210                 215                 220

Pro Tyr Thr Phe Gly Gly Gly Thr Lys Leu Glu Ile Lys Glu Pro Lys
225                 230                 235                 240

Ser Pro Asp Lys Thr His Thr Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ala Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Ile Tyr Ile Trp Ala Pro Leu Ala Gly Thr Cys Gly
465                 470                 475                 480

Val Leu Leu Leu Ser Leu Val Ile Thr Leu Tyr Cys Lys Arg Gly Arg
                485                 490                 495

Lys Lys Leu Leu Tyr Ile Phe Lys Gln Pro Phe Met Arg Pro Val Gln
            500                 505                 510

Thr Thr Gln Glu Glu Asp Gly Cys Ser Cys Arg Phe Pro Glu Glu Glu
        515                 520                 525

Glu Gly Gly Cys Glu Leu Arg Val Lys Phe Ser Arg Ser Ala Asp Ala
    530                 535                 540

Pro Ala Tyr Gln Gln Gly Gln Asn Gln Leu Tyr Asn Glu Leu Asn Leu
545                 550                 555                 560

Gly Arg Arg Glu Glu Tyr Asp Val Leu Asp Lys Arg Arg Gly Arg Asp
                565                 570                 575

Pro Glu Met Gly Gly Lys Pro Arg Arg Lys Asn Pro Gln Glu Gly Leu
            580                 585                 590

Tyr Asn Glu Leu Gln Lys Asp Lys Met Ala Glu Ala Tyr Ser Glu Ile
        595                 600                 605
```

Gly Met Lys Gly Glu Arg Arg Gly Lys Gly His Asp Gly Leu Tyr
    610                 615                 620

Gln Gly Leu Ser Thr Ala Thr Lys Asp Thr Tyr Asp Ala Leu His Met
625                 630                 635                 640

Gln Ala Leu Pro Pro Arg
                645

<210> SEQ ID NO 35
<211> LENGTH: 649
<212> TYPE: PRT
<213> ORGANISM: artificial sequence
<220> FEATURE:
<223> OTHER INFORMATION: 26292-6 polypeptide CAR sequence

<400> SEQUENCE: 35

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Val Gln Ile Thr Gln Ser Pro Ser Tyr Leu Ala Ala Ser
    130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
            180                 185                 190

Ser Gly Ser Gly Ser Gly Thr Asp Phe Thr Leu Thr Ile Ser Ser Leu
        195                 200                 205

Glu Pro Glu Asp Phe Ala Met Tyr Tyr Cys Gln Gln His Asn Lys Tyr
    210                 215                 220

Pro Tyr Thr Phe Gly Gly Gly Thr Lys Leu Glu Ile Lys Glu Pro Lys
225                 230                 235                 240

Ser Pro Asp Lys Thr His Thr Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ala Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys Ile Ile Ser Phe Phe Leu Ala Leu Thr Ser Thr Ala
465                 470                 475                 480

Leu Leu Phe Leu Leu Phe Phe Leu Thr Leu Arg Phe Ser Val Val Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
            515                 520                 525

Glu Glu Glu Glu Gly Gly Cys Glu Leu Arg Val Lys Phe Ser Arg Ser
            530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
            595                 600                 605

Ser Glu Ile Gly Met Lys Gly Glu Arg Arg Arg Gly Lys Gly His Asp
            610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 36
<211> LENGTH: 438
<212> TYPE: PRT
<213> ORGANISM: artificial sequence
<220> FEATURE:
<223> OTHER INFORMATION: 32716-1 polypeptide CAR sequence

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

-continued

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Ser Gly Gly Gly Ser
            115                 120                 125

Gly Gly Gly Ser Asp Ile Val Leu Thr Gln Ser Pro Ala Ser Leu
        130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
        195                 200                 205

Thr Leu Thr Ile Asn Pro Val Glu Ala Asp Asp Val Ala Thr Tyr Tyr
    210                 215                 220

Cys Gln Gln Ser Asn Glu Asp Pro Pro Thr Phe Gly Ala Gly Thr Lys
225                 230                 235                 240

Leu Glu Leu Lys Gly Leu Ala Val Ser Thr Ile Ser Ser Phe Phe Pro
                245                 250                 255

Pro Gly Tyr Gln Ile Tyr Ile Trp Ala Pro Leu Ala Gly Thr Cys Gly
            260                 265                 270

Val Leu Leu Leu Ser Leu Val Ile Thr Leu Tyr Cys Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Gly Arg Asp
        355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
        435

-continued

<210> SEQ ID NO 37
<211> LENGTH: 441
<212> TYPE: PRT
<213> ORGANISM: artificial sequence
<220> FEATURE:
<223> OTHER INFORMATION: 32716-2 polypeptide CAR sequence

<400> SEQUENCE: 37

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Ser Gly Gly Gly Gly Ser
        115                 120                 125

Gly Gly Gly Gly Ser Asp Ile Val Leu Thr Gln Ser Pro Ala Ser Leu
    130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
        195                 200                 205

Thr Leu Thr Ile Asn Pro Val Glu Ala Asp Asp Val Ala Thr Tyr Tyr
    210                 215                 220

Cys Gln Gln Ser Asn Glu Asp Pro Pro Thr Phe Gly Ala Gly Thr Lys
225                 230                 235                 240

Leu Glu Leu Lys Gly Leu Ala Val Ser Thr Ile Ser Ser Phe Phe Pro
                245                 250                 255

Pro Gly Tyr Gln Ile Ile Ser Phe Phe Leu Ala Leu Thr Ser Thr Ala
            260                 265                 270

Leu Leu Phe Leu Leu Phe Phe Leu Thr Leu Arg Phe Ser Val Val Lys
        275                 280                 285

Arg Gly Arg Lys Lys Leu Leu Tyr Ile Phe Lys Gln Pro Phe Met Arg
    290                 295                 300

Pro Val Gln Thr Thr Gln Glu Glu Asp Gly Cys Ser Cys Arg Phe Pro
305                 310                 315                 320

Glu Glu Glu Glu Gly Gly Cys Glu Leu Arg Val Lys Phe Ser Arg Ser
                325                 330                 335

Ala Asp Ala Pro Ala Tyr Gln Gln Gly Gln Asn Gln Leu Tyr Asn Glu
            340                 345                 350

Leu Asn Leu Gly Arg Arg Glu Glu Tyr Asp Val Leu Asp Lys Arg Arg
        355                 360                 365
```

Gly Arg Asp Pro Glu Met Gly Gly Lys Pro Arg Arg Lys Asn Pro Gln
    370                 375                 380

Glu Gly Leu Tyr Asn Glu Leu Gln Lys Asp Lys Met Ala Glu Ala Tyr
385                 390                 395                 400

Ser Glu Ile Gly Met Lys Gly Glu Arg Arg Arg Gly Lys Gly His Asp
                405                 410                 415

Gly Leu Tyr Gln Gly Leu Ser Thr Ala Thr Lys Asp Thr Tyr Asp Ala
                420                 425                 430

Leu His Met Gln Ala Leu Pro Pro Arg
                435                 440

<210> SEQ ID NO 38
<211> LENGTH: 467
<212> TYPE: PRT
<213> ORGANISM: artificial sequence
<220> FEATURE:
<223> OTHER INFORMATION: 32716-3 polypeptide CAR sequence

<400> SEQUENCE: 38

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
                20                  25                  30

Gly Met Asn Trp Val Lys Gln Ala Pro Gly Lys Ser Phe Lys Trp Met
            35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
                100                 105                 110

Ser Val Thr Val Ser Ser Gly Gly Gly Ser Gly Gly Gly Gly Ser
            115                 120                 125

Gly Gly Gly Gly Ser Asp Ile Val Leu Thr Gln Ser Pro Ala Ser Leu
    130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
    195                 200                 205

Thr Leu Thr Ile Asn Pro Val Glu Ala Asp Asp Val Ala Thr Tyr Tyr
    210                 215                 220

Cys Gln Gln Ser Asn Glu Asp Pro Pro Thr Phe Gly Ala Gly Thr Lys
225                 230                 235                 240

Leu Glu Leu Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
                260                 265                 270

Pro Ala Ala Gly Gly Ala Val His Thr Arg Gly Leu Asp Phe Ala Cys
            275                 280                 285

```
Asp Ile Tyr Ile Trp Ala Pro Leu Ala Gly Thr Cys Gly Val Leu Leu
            290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
                355                 360                 365

Gln Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
                420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
450                 455                 460

Pro Pro Arg
465

<210> SEQ ID NO 39
<211> LENGTH: 470
<212> TYPE: PRT
<213> ORGANISM: artificial sequence
<220> FEATURE:
<223> OTHER INFORMATION: 32716-4 polypeptide CAR sequence

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
                20                  25                  30

Gly Met Asn Trp Val Lys Gln Ala Pro Gly Lys Ser Phe Lys Trp Met
            35                  40                  45

Gly Trp Ile Asn Thr Tyr Thr Gly Glu Ser Tyr Ser Ala Asp Phe
50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Gly Ser Gly Gly Gly Gly Ser
                115                 120                 125

Gly Gly Gly Gly Ser Asp Ile Val Leu Thr Gln Ser Pro Ala Ser Leu
130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175
```

```
Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
        195                 200                 205

Thr Leu Thr Ile Asn Pro Val Glu Ala Asp Asp Val Ala Thr Tyr Tyr
    210                 215                 220

Cys Gln Gln Ser Asn Glu Asp Pro Pro Thr Phe Gly Ala Gly Thr Lys
225                 230                 235                 240

Leu Glu Leu Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Ile Ser Phe Phe Leu Ala Leu Thr Ser Thr Ala Leu Leu Phe
    290                 295                 300

Leu Leu Phe Phe Leu Thr Leu Arg Phe Ser Val Val Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 40
<211> LENGTH: 653
<212> TYPE: PRT
<213> ORGANISM: artificial sequence
<220> FEATURE:
<223> OTHER INFORMATION: 32716-5 polypeptide CAR sequence

<400> SEQUENCE: 40

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60
```

```
Lys Gly Arg Phe Ala Phe Ser Leu Glu Thr Ser Ala Ser Thr Ala Tyr
 65                  70                  75                  80

Leu His Ile Asn Asp Leu Lys Asn Glu Asp Thr Ala Thr Tyr Phe Cys
                 85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Gly Ser Gly Gly Gly Gly Ser
            115                 120                 125

Gly Gly Gly Gly Ser Asp Ile Val Leu Thr Gln Ser Pro Ala Ser Leu
            130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
            195                 200                 205

Thr Leu Thr Ile Asn Pro Val Glu Ala Asp Asp Val Ala Thr Tyr Tyr
        210                 215                 220

Cys Gln Gln Ser Asn Glu Asp Pro Pro Thr Phe Gly Ala Gly Thr Lys
225                 230                 235                 240

Leu Glu Leu Lys Glu Pro Lys Ser Pro Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ala Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys Ile Tyr Ile Trp Ala
465                 470                 475                 480

Pro Leu Ala Gly Thr Cys Gly Val Leu Leu Leu Ser Leu Val Ile Thr
```

```
                    485                 490                 495
Leu Tyr Cys Lys Arg Gly Arg Lys Leu Leu Tyr Ile Phe Lys Gln
            500                 505                 510

Pro Phe Met Arg Pro Val Gln Thr Thr Gln Glu Glu Asp Gly Cys Ser
            515                 520                 525

Cys Arg Phe Pro Glu Glu Glu Gly Gly Cys Glu Leu Arg Val Lys
            530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
                580                 585                 590

Lys Asn Pro Gln Glu Gly Leu Tyr Asn Glu Leu Gln Lys Asp Lys Met
                595                 600                 605

Ala Glu Ala Tyr Ser Glu Ile Gly Met Lys Gly Glu Arg Arg Arg Gly
                610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 41
<211> LENGTH: 656
<212> TYPE: PRT
<213> ORGANISM: artificial sequence
<220> FEATURE:
<223> OTHER INFORMATION: 32716-6 polypeptide CAR sequence

<400> SEQUENCE: 41

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Gly Ser Gly Gly Gly Gly Ser
            115                 120                 125

Gly Gly Gly Gly Ser Asp Ile Val Leu Thr Gln Ser Pro Ala Ser Leu
130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
```

```
                    195                 200                 205
Thr Leu Thr Ile Asn Pro Val Glu Ala Asp Val Ala Thr Tyr Tyr
    210                 215                 220

Cys Gln Gln Ser Asn Glu Asp Pro Pro Thr Phe Gly Ala Gly Thr Lys
225                 230                 235                 240

Leu Glu Leu Lys Glu Pro Lys Ser Pro Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ala Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ile Ile Ser Phe Phe
465                 470                 475                 480

Leu Ala Leu Thr Ser Thr Ala Leu Leu Phe Leu Leu Phe Phe Leu Thr
                485                 490                 495

Leu Arg Phe Ser Val Val Lys Arg Gly Arg Lys Lys Leu Leu Tyr Ile
            500                 505                 510

Phe Lys Gln Pro Phe Met Arg Pro Val Gln Thr Thr Gln Glu Glu Asp
        515                 520                 525

Gly Cys Ser Cys Arg Phe Pro Glu Glu Glu Gly Gly Cys Glu Leu
    530                 535                 540

Arg Val Lys Phe Ser Arg Ser Ala Asp Ala Pro Ala Tyr Gln Gln Gly
545                 550                 555                 560

Gln Asn Gln Leu Tyr Asn Glu Leu Asn Leu Gly Arg Arg Glu Glu Tyr
                565                 570                 575

Asp Val Leu Asp Lys Arg Arg Gly Arg Asp Pro Glu Met Gly Gly Lys
            580                 585                 590

Pro Arg Arg Lys Asn Pro Gln Glu Gly Leu Tyr Asn Glu Leu Gln Lys
        595                 600                 605

Asp Lys Met Ala Glu Ala Tyr Ser Glu Ile Gly Met Lys Gly Glu Arg
    610                 615                 620
```

```
Arg Arg Gly Lys Gly His Asp Gly Leu Tyr Gln Gly Leu Ser Thr Ala
625                 630                 635                 640

Thr Lys Asp Thr Tyr Asp Ala Leu His Met Gln Ala Leu Pro Pro Arg
            645                 650                 655
```

<210> SEQ ID NO 42
<211> LENGTH: 449
<212> TYPE: PRT
<213> ORGANISM: artificial sequence
<220> FEATURE:
<223> OTHER INFORMATION: Klo43-1 polypeptide CAR sequence

<400> SEQUENCE: 42

```
Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Gly Lys Ala Leu Glu Trp Leu
        35                  40                  45

Ala Leu Ile Arg Ser Lys Ala Asp Gly Tyr Thr Thr Glu Tyr Ser Ala
    50                  55                  60

Ser Val Lys Gly Arg Phe Thr Leu Ser Arg Asp Asp Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Ser Val Thr Val Ser Ser Gly
        115                 120                 125

Gly Gly Gly Ser Gly Gly Gly Ser Gly Gly Gly Ser Met Ala
    130                 135                 140

Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                165                 170                 175

Asp Ser Ala Val Ala Trp Tyr Gln Gln Lys Pro Gly Gln Ser Pro Lys
            180                 185                 190

Ala Leu Ile Tyr Ser Ala Ser Tyr Arg Tyr Ser Gly Val Pro Asp Arg
        195                 200                 205

Phe Thr Gly Arg Gly Ser Gly Thr Asp Phe Thr Leu Thr Ile Ser Ser
    210                 215                 220

Val Gln Ala Glu Asp Leu Ala Val Tyr Tyr Cys Gln Gln Tyr Tyr Ser
225                 230                 235                 240

Thr Pro Trp Thr Phe Gly Gly Gly Thr Lys Leu Glu Ile Lys Arg Gly
                245                 250                 255

Leu Ala Val Ser Thr Ile Ser Ser Phe Phe Pro Pro Gly Tyr Gln Ile
            260                 265                 270

Tyr Ile Trp Ala Pro Leu Ala Gly Thr Cys Gly Val Leu Leu Leu Ser
        275                 280                 285

Leu Val Ile Thr Leu Tyr Cys Lys Arg Gly Arg Lys Lys Leu Leu Tyr
    290                 295                 300

Ile Phe Lys Gln Pro Phe Met Arg Pro Val Gln Thr Thr Gln Glu Glu
305                 310                 315                 320

Asp Gly Cys Ser Cys Arg Phe Pro Glu Glu Glu Glu Gly Gly Cys Glu
                325                 330                 335
```

```
Leu Arg Val Lys Phe Ser Arg Ser Ala Asp Ala Pro Ala Tyr Gln Gln
            340                 345                 350

Gly Gln Asn Gln Leu Tyr Asn Glu Leu Asn Leu Gly Arg Arg Glu Glu
            355                 360                 365

Tyr Asp Val Leu Asp Lys Arg Arg Gly Arg Asp Pro Glu Met Gly Gly
            370                 375                 380

Lys Pro Arg Arg Lys Asn Pro Gln Glu Gly Leu Tyr Asn Glu Leu Gln
385                 390                 395                 400

Lys Asp Lys Met Ala Glu Ala Tyr Ser Glu Ile Gly Met Lys Gly Glu
                405                 410                 415

Arg Arg Arg Gly Lys Gly His Asp Gly Leu Tyr Gln Gly Leu Ser Thr
            420                 425                 430

Ala Thr Lys Asp Thr Tyr Asp Ala Leu His Met Gln Ala Leu Pro Pro
            435                 440                 445

Arg

<210> SEQ ID NO 43
<211> LENGTH: 452
<212> TYPE: PRT
<213> ORGANISM: artificial sequence
<220> FEATURE:
<223> OTHER INFORMATION: Klo43-2 polypeptide CAR sequence

<400> SEQUENCE: 43

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
            35                  40                  45

Ala Leu Ile Arg Ser Lys Ala Asp Gly Tyr Thr Thr Glu Tyr Ser Ala
        50                  55                  60

Ser Val Lys Gly Arg Phe Thr Leu Ser Arg Asp Asp Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Ser Val Thr Val Ser Ser Gly
            115                 120                 125

Gly Gly Gly Ser Gly Gly Gly Gly Ser Gly Gly Gly Gly Ser Met Ala
        130                 135                 140

Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                165                 170                 175

Asp Ser Ala Val Ala Trp Tyr Gln Gln Lys Pro Gly Gln Ser Pro Lys
            180                 185                 190

Ala Leu Ile Tyr Ser Ala Ser Tyr Arg Tyr Ser Gly Val Pro Asp Arg
        195                 200                 205

Phe Thr Gly Arg Gly Ser Gly Thr Asp Phe Thr Leu Thr Ile Ser Ser
    210                 215                 220

Val Gln Ala Glu Asp Leu Ala Val Tyr Tyr Cys Gln Gln Tyr Tyr Ser
225                 230                 235                 240
```

```
Thr Pro Trp Thr Phe Gly Gly Gly Thr Lys Leu Glu Ile Lys Arg Gly
                245                 250                 255

Leu Ala Val Ser Thr Ile Ser Ser Phe Phe Pro Pro Gly Tyr Gln Ile
            260                 265                 270

Ile Ser Phe Phe Leu Ala Leu Thr Ser Thr Ala Leu Leu Phe Leu Leu
        275                 280                 285

Phe Phe Leu Thr Leu Arg Phe Ser Val Val Lys Arg Gly Arg Lys Lys
    290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
                325                 330                 335

Gly Cys Glu Leu Arg Val Lys Phe Ser Arg Ser Ala Asp Ala Pro Ala
            340                 345                 350

Tyr Gln Gln Gly Gln Asn Gln Leu Tyr Asn Glu Leu Asn Leu Gly Arg
        355                 360                 365

Arg Glu Glu Tyr Asp Val Leu Asp Lys Arg Arg Gly Arg Asp Pro Glu
    370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
        435                 440                 445

Leu Pro Pro Arg
    450

<210> SEQ ID NO 44
<211> LENGTH: 478
<212> TYPE: PRT
<213> ORGANISM: artificial sequence
<220> FEATURE:
<223> OTHER INFORMATION: Klo43-3 polypeptide CAR sequence

<400> SEQUENCE: 44

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Ala Leu Ile Arg Ser Lys Ala Asp Gly Tyr Thr Thr Glu Tyr Ser Ala
    50                  55                  60

Ser Val Lys Gly Arg Phe Thr Leu Ser Arg Asp Asp Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Ser Val Thr Val Ser Ser Gly
        115                 120                 125

Gly Gly Gly Ser Gly Gly Gly Gly Ser Gly Gly Gly Gly Ser Met Ala
    130                 135                 140
```

```
Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                165                 170                 175

Asp Ser Ala Val Ala Trp Tyr Gln Gln Lys Pro Gly Gln Ser Pro Lys
            180                 185                 190

Ala Leu Ile Tyr Ser Ala Ser Tyr Arg Tyr Ser Gly Val Pro Asp Arg
        195                 200                 205

Phe Thr Gly Arg Gly Ser Gly Thr Asp Phe Thr Leu Thr Ile Ser Ser
    210                 215                 220

Val Gln Ala Glu Asp Leu Ala Val Tyr Tyr Cys Gln Gln Tyr Tyr Ser
225                 230                 235                 240

Thr Pro Trp Thr Phe Gly Gly Gly Thr Lys Leu Glu Ile Lys Arg Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
            340                 345                 350

Ser Cys Arg Phe Pro Glu Glu Glu Gly Gly Cys Glu Leu Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 45
<211> LENGTH: 481
<212> TYPE: PRT
<213> ORGANISM: artificial sequence
<220> FEATURE:
<223> OTHER INFORMATION: Klo43-4 polypeptide CAR sequence

<400> SEQUENCE: 45

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30
```

```
Tyr Met Ser Trp Val Arg Gln Pro Pro Gly Lys Ala Leu Glu Trp Leu
         35                  40                  45

Ala Leu Ile Arg Ser Lys Ala Asp Gly Tyr Thr Thr Glu Tyr Ser Ala
 50                  55                  60

Ser Val Lys Gly Arg Phe Thr Leu Ser Arg Asp Asp Ser Gln Ser Ile
 65                  70                  75                  80

Leu Tyr Leu Gln Met Asn Ala Leu Arg Pro Glu Asp Ser Ala Thr Tyr
                 85                  90                  95

Tyr Cys Ala Arg Asp Ala Ala Tyr Tyr Ser Tyr Tyr Ser Pro Glu Gly
             100                 105                 110

Ala Met Asp Tyr Trp Gly Gln Gly Thr Ser Val Thr Val Ser Ser Gly
         115                 120                 125

Gly Gly Ser Gly Gly Gly Ser Gly Gly Gly Ser Met Ala
 130                 135                 140

Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                 165                 170                 175

Asp Ser Ala Val Ala Trp Tyr Gln Gln Lys Pro Gly Gln Ser Pro Lys
            180                 185                 190

Ala Leu Ile Tyr Ser Ala Ser Tyr Arg Tyr Ser Gly Val Pro Asp Arg
        195                 200                 205

Phe Thr Gly Arg Gly Ser Gly Thr Asp Phe Thr Leu Thr Ile Ser Ser
    210                 215                 220

Val Gln Ala Glu Asp Leu Ala Val Tyr Tyr Cys Gln Gln Tyr Tyr Ser
225                 230                 235                 240

Thr Pro Trp Thr Phe Gly Gly Gly Thr Lys Leu Glu Ile Lys Arg Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Ile Ser Phe
    290                 295                 300

Phe Leu Ala Leu Thr Ser Thr Ala Leu Leu Phe Leu Leu Phe Phe Leu
305                 310                 315                 320

Thr Leu Arg Phe Ser Val Val Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
```

450                 455                 460
Ala Thr Lys Asp Thr Tyr Asp Ala Leu His Met Gln Ala Leu Pro Pro
465                 470                 475                 480

Arg

<210> SEQ ID NO 46
<211> LENGTH: 664
<212> TYPE: PRT
<213> ORGANISM: artificial sequence
<220> FEATURE:
<223> OTHER INFORMATION: Klo43-5 polypeptide CAR sequence

<400> SEQUENCE: 46

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
                20                  25                  30

Tyr Met Ser Trp Val Arg Gln Pro Gly Lys Ala Leu Glu Trp Leu
            35                  40                  45

Ala Leu Ile Arg Ser Lys Ala Asp Gly Tyr Thr Thr Glu Tyr Ser Ala
        50                  55                  60

Ser Val Lys Gly Arg Phe Thr Leu Ser Arg Asp Asp Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Ser Val Thr Val Ser Ser Gly
        115                 120                 125

Gly Gly Gly Ser Gly Gly Gly Ser Gly Gly Gly Ser Met Ala
    130                 135                 140

Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                165                 170                 175

Asp Ser Ala Val Ala Trp Tyr Gln Gln Lys Pro Gly Gln Ser Pro Lys
            180                 185                 190

Ala Leu Ile Tyr Ser Ala Ser Tyr Arg Tyr Ser Gly Val Pro Asp Arg
        195                 200                 205

Phe Thr Gly Arg Gly Ser Gly Thr Asp Phe Thr Leu Thr Ile Ser Ser
    210                 215                 220

Val Gln Ala Glu Asp Leu Ala Val Tyr Tyr Cys Gln Gln Tyr Tyr Ser
225                 230                 235                 240

Thr Pro Trp Thr Phe Gly Gly Gly Thr Lys Leu Glu Ile Lys Arg Glu
                245                 250                 255

Pro Lys Ser Pro Asp Lys Thr His Thr Cys Pro Pro Cys Pro Ala Pro
            260                 265                 270

Pro Val Ala Gly Pro Ser Val Phe Leu Phe Pro Pro Lys Pro Lys Asp
        275                 280                 285

Thr Leu Met Ile Ala Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

```
Ser Thr Tyr Arg Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys Ile Tyr Ile Trp Ala Pro Leu Ala Gly Thr
                485                 490                 495

Cys Gly Val Leu Leu Leu Ser Leu Val Ile Thr Leu Tyr Cys Lys Arg
            500                 505                 510

Gly Arg Lys Lys Leu Leu Tyr Ile Phe Lys Gln Pro Phe Met Arg Pro
        515                 520                 525

Val Gln Thr Thr Gln Glu Glu Asp Gly Cys Ser Cys Arg Phe Pro Glu
    530                 535                 540

Glu Glu Glu Gly Gly Cys Glu Leu Arg Val Lys Phe Ser Arg Ser Ala
545                 550                 555                 560

Asp Ala Pro Ala Tyr Gln Gln Gly Gln Asn Gln Leu Tyr Asn Glu Leu
                565                 570                 575

Asn Leu Gly Arg Arg Glu Glu Tyr Asp Val Leu Asp Lys Arg Arg Gly
            580                 585                 590

Arg Asp Pro Glu Met Gly Gly Lys Pro Arg Arg Lys Asn Pro Gln Glu
        595                 600                 605

Gly Leu Tyr Asn Glu Leu Gln Lys Asp Lys Met Ala Glu Ala Tyr Ser
    610                 615                 620

Glu Ile Gly Met Lys Gly Glu Arg Arg Arg Gly Lys Gly His Asp Gly
625                 630                 635                 640

Leu Tyr Gln Gly Leu Ser Thr Ala Thr Lys Asp Thr Tyr Asp Ala Leu
                645                 650                 655

His Met Gln Ala Leu Pro Pro Arg
            660

<210> SEQ ID NO 47
<211> LENGTH: 667
<212> TYPE: PRT
<213> ORGANISM: artificial sequence
<220> FEATURE:
<223> OTHER INFORMATION: Klo43-6 polypeptide CAR sequence

<400> SEQUENCE: 47

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30
```

```
Tyr Met Ser Trp Val Arg Gln Pro Pro Gly Lys Ala Leu Glu Trp Leu
        35                  40                  45

Ala Leu Ile Arg Ser Lys Ala Asp Gly Tyr Thr Thr Glu Tyr Ser Ala
 50                  55                  60

Ser Val Lys Gly Arg Phe Thr Leu Ser Arg Asp Asp Ser Gln Ser Ile
 65                  70                  75                  80

Leu Tyr Leu Gln Met Asn Ala Leu Arg Pro Glu Asp Ser Ala Thr Tyr
                 85                  90                  95

Tyr Cys Ala Arg Asp Ala Ala Tyr Tyr Ser Tyr Tyr Ser Pro Glu Gly
                100                 105                 110

Ala Met Asp Tyr Trp Gly Gln Gly Thr Ser Val Thr Val Ser Ser Gly
                115                 120                 125

Gly Gly Gly Ser Gly Gly Gly Ser Gly Gly Gly Ser Met Ala
        130                 135                 140

Asp Tyr Lys Asp Ile Val Met Thr Gln Ser His Lys Phe Met Ser Thr
145                 150                 155                 160

Ser Val Gly Asp Arg Val Asn Ile Thr Cys Lys Ala Ser Gln Asn Val
                165                 170                 175

Asp Ser Ala Val Ala Trp Tyr Gln Gln Lys Pro Gly Gln Ser Pro Lys
                180                 185                 190

Ala Leu Ile Tyr Ser Ala Ser Tyr Arg Tyr Ser Gly Val Pro Asp Arg
                195                 200                 205

Phe Thr Gly Arg Gly Ser Gly Thr Asp Phe Thr Leu Thr Ile Ser Ser
210                 215                 220

Val Gln Ala Glu Asp Leu Ala Val Tyr Tyr Cys Gln Gln Tyr Tyr Ser
225                 230                 235                 240

Thr Pro Trp Thr Phe Gly Gly Gly Thr Lys Leu Glu Ile Lys Arg Glu
                245                 250                 255

Pro Lys Ser Pro Asp Lys Thr His Thr Cys Pro Pro Cys Pro Ala Pro
                260                 265                 270

Pro Val Ala Gly Pro Ser Val Phe Leu Phe Pro Pro Lys Pro Lys Asp
                275                 280                 285

Thr Leu Met Ile Ala Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Ser Phe Phe Leu Tyr Ser Lys
                435                 440                 445
```

```
Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys Ile Ile Ser Phe Phe Leu Ala Leu Thr Ser
                485                 490                 495

Thr Ala Leu Leu Phe Leu Leu Phe Leu Thr Leu Arg Phe Ser Val
            500                 505                 510

Val Lys Arg Gly Arg Lys Lys Leu Tyr Ile Phe Lys Gln Pro Phe
            515                 520                 525

Met Arg Pro Val Gln Thr Thr Gln Glu Glu Asp Gly Cys Ser Cys Arg
530                 535                 540

Phe Pro Glu Glu Glu Glu Gly Gly Cys Glu Leu Arg Val Lys Phe Ser
545                 550                 555                 560

Arg Ser Ala Asp Ala Pro Ala Tyr Gln Gln Gly Gln Asn Gln Leu Tyr
                565                 570                 575

Asn Glu Leu Asn Leu Gly Arg Arg Glu Glu Tyr Asp Val Leu Asp Lys
            580                 585                 590

Arg Arg Gly Arg Asp Pro Glu Met Gly Gly Lys Pro Arg Arg Lys Asn
            595                 600                 605

Pro Gln Glu Gly Leu Tyr Asn Glu Leu Gln Lys Asp Lys Met Ala Glu
610                 615                 620

Ala Tyr Ser Glu Ile Gly Met Lys Gly Glu Arg Arg Arg Gly Lys Gly
625                 630                 635                 640

His Asp Gly Leu Tyr Gln Gly Leu Ser Thr Ala Thr Lys Asp Thr Tyr
                645                 650                 655

Asp Ala Leu His Met Gln Ala Leu Pro Pro Arg
            660                 665

<210> SEQ ID NO 48
<211> LENGTH: 470
<212> TYPE: PRT
<213> ORGANISM: artificial sequence
<220> FEATURE:
<223> OTHER INFORMATION: 12F1-3 polypeptide CAR sequence

<400> SEQUENCE: 48

Val Gln Leu Gln Glu Ser Gly Pro Gly Leu Val Lys Pro Ser Gln Ser
1               5                   10                  15

Leu Ser Leu Thr Cys Ser Val Thr Asp Tyr Ser Ile Thr Ser Gly Tyr
            20                  25                  30

Tyr Trp Asn Trp Ile Arg Gln Phe Pro Gly Asn Lys Leu Glu Trp Met
        35                  40                  45

Gly Tyr Ile Ser Tyr Asp Gly Ser Asn Asn Tyr Asn Pro Ser Leu Lys
    50                  55                  60

Asn Arg Ile Ser Ile Thr Arg Asp Thr Ser Lys Asn Gln Phe Phe Leu
65                  70                  75                  80

Lys Leu Ser Ser Val Thr Thr Glu Asp Thr Ala Thr Tyr Tyr Cys Ser
                85                  90                  95

Arg Gly Glu Gly Phe Tyr Phe Asp Ser Trp Gly Gln Gly Thr Thr Leu
            100                 105                 110

Thr Val Ser Ser Ala Arg Ser Gly Gly Gly Gly Ser Gly Gly Gly Gly
        115                 120                 125

Ser Gly Gly Gly Gly Ser Asp Ile Met Met Ser Gln Ser Pro Ser Ser
    130                 135                 140
```

Leu Ala Val Ser Val Gly Glu Lys Phe Thr Met Thr Cys Lys Ser Ser
145                 150                 155                 160

Gln Ser Leu Phe Phe Gly Ser Thr Gln Lys Asn Tyr Leu Ala Trp Tyr
            165                 170                 175

Gln Gln Lys Pro Gly Gln Ser Pro Lys Leu Leu Ile Tyr Trp Ala Ser
            180                 185                 190

Thr Arg Glu Ser Gly Val Pro Asp Arg Phe Thr Gly Ser Gly Ser Gly
            195                 200                 205

Thr Asp Phe Thr Leu Ala Ile Ser Ser Val Met Pro Glu Asp Leu Ala
210                 215                 220

Val Tyr Tyr Cys Gln Gln Tyr Tyr Asn Tyr Pro Trp Thr Phe Gly Gly
225                 230                 235                 240

Gly Thr Lys Leu Glu Ile Lys Thr Thr Thr Pro Ala Pro Arg Pro Pro
            245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Ile Tyr Ile Trp Ala Pro Leu Ala Gly Thr Cys Gly
290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
            355                 360                 365

Pro Ala Tyr Gln Gln Gly Gln Asn Gln Leu Tyr Asn Glu Leu Asn Leu
            370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
            405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
            450                 455                 460

Gln Ala Leu Pro Pro Arg
465                 470

<210> SEQ ID NO 49
<211> LENGTH: 49
<212> TYPE: PRT
<213> ORGANISM: Artificial sequence
<220> FEATURE:
<223> OTHER INFORMATION: Target TALEN TRAC_T01

<400> SEQUENCE: 49

Thr Thr Gly Thr Cys Cys Cys Ala Cys Ala Gly Ala Thr Ala Thr Cys
1               5                   10                  15

Cys Ala Gly Ala Ala Cys Cys Cys Thr Gly Ala Cys Cys Cys Thr Gly
                20                  25                  30

```
Cys Cys Gly Thr Gly Thr Ala Cys Cys Ala Gly Cys Thr Gly Ala Gly
        35                  40                  45

Ala
```

<210> SEQ ID NO 50
<211> LENGTH: 530
<212> TYPE: PRT
<213> ORGANISM: Artificial sequence
<220> FEATURE:
<223> OTHER INFORMATION: TAL binding domain  TRAC_T01-L

<400> SEQUENCE: 50

```
Leu Thr Pro Gln Gln Val Val Ala Ile Ala Ser Asn Gly Gly Gly Lys
 1               5                  10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
```

```
            340                 345                 350
Ile Gly Gly Lys Gln Ala Leu Glu Thr Val Gln Ala Leu Leu Pro Val
            355                 360                 365
Leu Cys Gln Ala His Gly Leu Thr Pro Gln Gln Val Val Ala Ile Ala
            370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Gln Gln Val
            435                 440                 445
Val Ala Ile Ala Ser Asn Gly Gly Gly Lys Gln Ala Leu Glu Thr Val
            450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Gly Arg Pro Ala
            515                 520                 525
Leu Glu
    530
```

<210> SEQ ID NO 51
<211> LENGTH: 530
<212> TYPE: PRT
<213> ORGANISM: Artificial sequence
<220> FEATURE:
<223> OTHER INFORMATION: TAL binding domain TRAC_T01-R

<400> SEQUENCE: 51

```
Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Gln Gln Val Val Ala Ile Ala Ser Asn Gly Gly
            35                  40                  45
Gly Lys Gln Ala Leu Glu Thr Val Gln Arg Leu Leu Pro Val Leu Cys
        50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
                100                 105                 110
Ser Asn Ile Gly Gly Lys Gln Ala Leu Glu Thr Val Gln Ala Leu Leu
            115                 120                 125
Pro Val Leu Cys Gln Ala His Gly Leu Thr Pro Gln Gln Val Val Ala
        130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
```

```
                165                 170                 175
Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 52
<211> LENGTH: 2814
<212> TYPE: PRT
<213> ORGANISM: Artificial sequence
<220> FEATURE:
<223> OTHER INFORMATION: polynucleotide encoding  TRAC_T01-L TALEN
```

<400> SEQUENCE: 52

Ala Thr Gly Gly Gly Cys Gly Ala Thr Cys Cys Thr Ala Ala Ala Ala
1 5 10 15

Ala Gly Ala Ala Ala Cys Gly Thr Ala Ala Gly Gly Thr Cys Ala Thr
20 25 30

Cys Gly Ala Thr Thr Ala Cys Cys Cys Ala Thr Ala Cys Gly Ala Thr
35 40 45

Gly Thr Thr Cys Cys Ala Gly Ala Thr Thr Ala Cys Gly Cys Thr Ala
50 55 60

Thr Cys Gly Ala Thr Ala Thr Cys Gly Cys Cys Gly Ala Thr Cys Thr
65 70 75 80

Ala Cys Gly Cys Ala Cys Gly Cys Thr Cys Gly Gly Cys Thr Ala Cys
85 90 95

Ala Gly Cys Cys Ala Gly Cys Ala Gly Cys Ala Ala Cys Ala Gly Gly
100 105 110

Ala Gly Ala Ala Gly Ala Thr Cys Ala Ala Ala Cys Cys Gly Ala Ala
115 120 125

Gly Gly Thr Thr Cys Gly Thr Thr Cys Gly Ala Cys Ala Gly Thr Gly
130 135 140

Gly Cys Gly Cys Ala Gly Cys Ala Cys Cys Ala Cys Gly Ala Gly Gly
145 150 155 160

Cys Ala Cys Thr Gly Gly Thr Cys Gly Gly Cys Cys Ala Cys Gly Gly
165 170 175

Gly Thr Thr Thr Ala Cys Ala Cys Ala Cys Gly Cys Gly Cys Ala Cys
180 185 190

Ala Thr Cys Gly Thr Thr Gly Cys Gly Thr Thr Ala Ala Gly Cys Cys
195 200 205

Ala Ala Cys Ala Cys Cys Cys Gly Gly Cys Ala Gly Cys Gly Thr Thr
210 215 220

Ala Gly Gly Gly Ala Cys Cys Gly Thr Cys Gly Cys Thr Gly Thr Cys
225 230 235 240

Ala Ala Gly Thr Ala Thr Cys Ala Gly Gly Ala Cys Ala Thr Gly Ala
245 250 255

Thr Cys Gly Cys Ala Gly Cys Gly Thr Thr Gly Cys Cys Ala Gly Ala
260 265 270

Gly Gly Cys Gly Ala Cys Ala Cys Ala Cys Gly Ala Ala Gly Cys Gly
275 280 285

Ala Thr Cys Gly Thr Thr Gly Gly Cys Gly Thr Cys Gly Gly Cys Ala
290 295 300

Ala Ala Cys Ala Gly Thr Gly Gly Thr Cys Cys Gly Gly Cys Gly Cys
305 310 315 320

Ala Cys Gly Cys Gly Cys Thr Cys Thr Gly Gly Ala Gly Gly Cys Cys
325 330 335

Thr Thr Gly Cys Thr Cys Ala Cys Gly Gly Thr Gly Gly Cys Gly Gly
340 345 350

Gly Ala Gly Ala Gly Thr Thr Gly Ala Gly Ala Gly Gly Thr Cys Cys
355 360 365

Ala Cys Cys Gly Thr Thr Ala Cys Ala Gly Thr Thr Gly Gly Ala Cys
370 375 380

Ala Cys Ala Gly Gly Cys Cys Ala Ala Cys Thr Thr Cys Thr Cys Ala
385 390 395 400

Ala Gly Ala Thr Thr Gly Cys Ala Ala Ala Ala Cys Gly Thr Gly Gly
405 410 415

```
Cys Gly Gly Cys Gly Thr Gly Ala Cys Cys Gly Cys Ala Gly Thr Gly
                420                 425                 430

Gly Ala Gly Gly Cys Ala Gly Thr Gly Cys Ala Thr Gly Cys Ala Thr
            435                 440                 445

Gly Gly Cys Gly Cys Ala Ala Thr Gly Cys Ala Cys Thr Gly Ala Cys
        450                 455                 460

Gly Gly Gly Thr Gly Cys Cys Cys Gly Cys Thr Cys Ala Ala Cys
465                 470                 475                 480

Thr Thr Gly Ala Cys Cys Cys Cys Ala Gly Cys Ala Gly Gly
                485                 490                 495

Thr Gly Gly Thr Gly Gly Cys Cys Ala Thr Cys Gly Cys Cys Ala Gly
            500                 505                 510

Cys Ala Ala Thr Gly Gly Cys Gly Gly Thr Gly Gly Cys Ala Ala Gly
                515                 520                 525

Cys Ala Gly Gly Cys Gly Cys Thr Gly Gly Ala Gly Ala Cys Gly Gly
            530                 535                 540

Thr Cys Cys Ala Gly Cys Gly Gly Cys Thr Gly Thr Thr Gly Cys Cys
545                 550                 555                 560

Gly Gly Thr Gly Cys Thr Gly Thr Gly Cys Cys Ala Gly Gly Cys Cys
                565                 570                 575

Cys Ala Cys Gly Gly Cys Thr Thr Gly Ala Cys Cys Cys Cys Cys
            580                 585                 590

Ala Gly Cys Ala Gly Gly Thr Gly Gly Thr Gly Gly Cys Cys Ala Thr
        595                 600                 605

Cys Gly Cys Cys Ala Gly Cys Ala Ala Thr Ala Ala Thr Gly Gly Thr
    610                 615                 620

Gly Gly Cys Ala Ala Gly Cys Ala Gly Gly Cys Gly Cys Thr Gly Gly
625                 630                 635                 640

Ala Gly Ala Cys Gly Gly Thr Cys Cys Ala Gly Cys Gly Gly Cys Thr
            645                 650                 655

Gly Thr Thr Gly Cys Cys Gly Gly Thr Gly Cys Thr Gly Thr Gly Cys
                660                 665                 670

Cys Ala Gly Gly Cys Cys Cys Ala Cys Gly Gly Cys Thr Thr Gly Ala
            675                 680                 685

Cys Cys Cys Cys Cys Ala Gly Cys Ala Gly Gly Thr Gly Gly Thr
        690                 695                 700

Gly Gly Cys Cys Ala Thr Cys Gly Cys Cys Ala Gly Cys Ala Ala Thr
705                 710                 715                 720

Gly Gly Cys Gly Gly Thr Gly Gly Cys Ala Ala Gly Cys Ala Gly Gly
                725                 730                 735

Cys Gly Cys Thr Gly Gly Ala Gly Ala Cys Gly Gly Thr Cys Cys Ala
            740                 745                 750

Gly Cys Gly Gly Cys Thr Gly Thr Thr Gly Cys Cys Gly Gly Thr Gly
                755                 760                 765

Cys Thr Gly Thr Gly Cys Cys Ala Gly Gly Cys Cys Cys Ala Cys Gly
        770                 775                 780

Gly Cys Thr Thr Gly Ala Cys Cys Cys Cys Cys Gly Gly Ala Gly Cys
785                 790                 795                 800

Gly Gly Thr Gly Gly Thr Gly Gly Cys Cys Ala Thr Cys Gly Cys Cys
                805                 810                 815

Ala Gly Cys Cys Ala Cys Gly Ala Thr Gly Gly Cys Gly Gly Cys Ala
            820                 825                 830
```

Ala Gly Cys Ala Gly Gly Cys Thr Gly Gly Ala Gly Ala Cys
            835             840             845

Gly Gly Thr Cys Cys Ala Gly Cys Gly Gly Cys Thr Gly Thr Thr Gly
        850             855             860

Cys Cys Gly Gly Thr Gly Cys Thr Gly Thr Gly Cys Cys Ala Gly Gly
865             870             875             880

Cys Cys Cys Ala Cys Gly Gly Cys Thr Thr Gly Ala Cys Cys Cys
            885             890             895

Gly Gly Ala Gly Cys Ala Gly Gly Thr Gly Thr Gly Cys Cys
            900             905             910

Ala Thr Cys Gly Cys Cys Ala Gly Cys Ala Cys Gly Ala Thr Gly
        915             920             925

Gly Cys Gly Gly Cys Ala Ala Gly Cys Ala Gly Gly Cys Gly Cys Thr
        930             935             940

Gly Gly Ala Gly Ala Cys Gly Gly Thr Cys Cys Ala Gly Cys Gly Gly
945             950             955             960

Cys Thr Gly Thr Thr Gly Cys Cys Gly Gly Thr Gly Cys Thr Gly Thr
            965             970             975

Gly Cys Cys Ala Gly Gly Cys Cys Cys Ala Cys Gly Gly Cys Thr Thr
        980             985             990

Gly Ala Cys Cys Cys Gly Gly  Ala Gly Cys Ala Gly  Gly Thr Gly
        995             1000             1005

Gly Thr  Gly Gly Cys Cys Ala  Thr Cys Gly Cys Cys  Ala Gly Cys
    1010             1015             1020

Cys Ala  Cys Gly Ala Thr Gly  Gly Cys Gly Gly Cys  Ala Ala Gly
    1025             1030             1035

Cys Ala  Gly Gly Cys Gly Cys  Thr Gly Gly Ala Gly  Ala Cys Gly
    1040             1045             1050

Gly Thr  Cys Cys Ala Gly Cys  Gly Gly Cys Thr Gly  Thr Thr Gly
    1055             1060             1065

Cys Cys  Gly Gly Thr Gly Cys  Thr Gly Thr Gly Cys  Cys Ala Gly
    1070             1075             1080

Gly Cys  Cys Cys Ala Cys Gly  Gly Cys Thr Thr Gly  Ala Cys Cys
    1085             1090             1095

Cys Cys  Gly Gly Ala Gly Cys  Ala Gly Gly Thr Gly  Gly Thr Gly
    1100             1105             1110

Gly Cys  Cys Ala Thr Cys Gly  Cys Cys Ala Gly Cys  Ala Ala Thr
    1115             1120             1125

Ala Thr  Thr Gly Gly Thr Gly  Gly Cys Ala Ala Gly  Cys Ala Gly
    1130             1135             1140

Gly Cys  Gly Cys Thr Gly Gly  Ala Gly Ala Cys Gly  Gly Thr Gly
    1145             1150             1155

Cys Ala  Gly Gly Cys Gly Cys  Thr Gly Thr Thr Gly  Cys Cys Gly
    1160             1165             1170

Gly Thr  Gly Cys Thr Gly Thr  Gly Cys Cys Ala Gly  Gly Cys Cys
    1175             1180             1185

Cys Ala  Cys Gly Gly Cys Thr  Thr Gly Ala Cys Cys  Cys Cys Gly
    1190             1195             1200

Gly Ala  Gly Cys Ala Gly Gly  Thr Gly Gly Thr Gly  Gly Cys Cys
    1205             1210             1215

Ala Thr  Cys Gly Cys Cys Ala  Gly Cys Cys Ala Cys  Gly Ala Thr
    1220             1225             1230

Gly Gly  Cys Gly Gly Cys Ala  Ala Gly Cys Ala Gly  Gly Cys Gly

```
                    1235                1240                1245

Cys Thr Gly Gly Ala Gly Ala Cys Gly Gly Thr Cys Cys Ala Gly
            1250                1255                1260

Cys Gly Gly Cys Thr Gly Thr Thr Gly Cys Cys Gly Gly Thr Gly
            1265                1270                1275

Cys Thr Gly Thr Gly Cys Cys Ala Gly Gly Cys Cys Cys Ala Cys
            1280                1285                1290

Gly Gly Cys Thr Thr Gly Ala Cys Cys Cys Cys Gly Gly Ala Gly
            1295                1300                1305

Cys Ala Gly Gly Thr Gly Gly Thr Gly Gly Cys Cys Ala Thr Cys
            1310                1315                1320

Gly Cys Cys Ala Gly Cys Ala Ala Thr Ala Thr Thr Gly Gly Thr
            1325                1330                1335

Gly Gly Cys Ala Ala Gly Cys Ala Gly Gly Cys Gly Cys Thr Gly
            1340                1345                1350

Gly Ala Gly Ala Cys Gly Gly Thr Gly Cys Ala Gly Gly Cys Gly
            1355                1360                1365

Cys Thr Gly Thr Thr Gly Cys Cys Gly Gly Thr Gly Cys Thr Gly
            1370                1375                1380

Thr Gly Cys Cys Ala Gly Gly Cys Cys Cys Ala Cys Gly Gly Cys
            1385                1390                1395

Thr Thr Gly Ala Cys Cys Cys Cys Cys Ala Gly Cys Ala Gly Gly
            1400                1405                1410

Gly Thr Gly Gly Thr Gly Gly Cys Cys Ala Thr Cys Gly Cys Cys
            1415                1420                1425

Ala Gly Cys Ala Ala Thr Ala Ala Thr Gly Gly Thr Gly Gly Cys
            1430                1435                1440

Ala Ala Gly Cys Ala Gly Gly Cys Gly Cys Thr Gly Gly Ala Gly
            1445                1450                1455

Ala Cys Gly Gly Thr Cys Cys Ala Gly Cys Gly Gly Cys Thr Gly
            1460                1465                1470

Thr Thr Gly Cys Cys Gly Gly Thr Gly Cys Thr Gly Thr Gly Cys
            1475                1480                1485

Cys Ala Gly Gly Cys Cys Cys Ala Cys Gly Gly Cys Thr Thr Gly
            1490                1495                1500

Ala Cys Cys Cys Cys Gly Gly Ala Gly Cys Ala Gly Gly Thr Gly
            1505                1510                1515

Gly Thr Gly Gly Cys Cys Ala Thr Cys Gly Cys Cys Ala Gly Cys
            1520                1525                1530

Ala Ala Thr Ala Thr Thr Gly Gly Thr Gly Gly Cys Ala Ala Gly
            1535                1540                1545

Cys Ala Gly Gly Cys Gly Cys Thr Gly Gly Ala Gly Ala Cys Gly
            1550                1555                1560

Gly Thr Gly Cys Ala Gly Gly Cys Gly Cys Thr Gly Thr Thr Gly
            1565                1570                1575

Cys Cys Gly Gly Thr Gly Cys Thr Gly Thr Gly Cys Cys Ala Gly
            1580                1585                1590

Gly Cys Cys Cys Ala Cys Gly Gly Cys Thr Thr Gly Ala Cys Cys
            1595                1600                1605

Cys Cys Cys Cys Ala Gly Cys Ala Gly Gly Thr Gly Gly Thr Gly
            1610                1615                1620

Gly Cys Cys Ala Thr Cys Gly Cys Cys Ala Gly Cys Ala Ala Thr
            1625                1630                1635
```

-continued

Gly Gly Cys Gly Gly Thr Gly Gly Cys Ala Ala Gly Cys Ala Gly
    1640                1645                1650

Gly Cys Gly Cys Thr Gly Gly Ala Gly Ala Cys Gly Gly Thr Cys
    1655                1660                1665

Cys Ala Gly Cys Gly Gly Cys Thr Gly Thr Thr Gly Cys Cys Gly
    1670                1675                1680

Gly Thr Gly Cys Thr Gly Thr Gly Cys Cys Ala Gly Gly Cys Cys
    1685                1690                1695

Cys Ala Cys Gly Gly Cys Thr Thr Gly Ala Cys Cys Cys Gly
    1700                1705                1710

Gly Ala Gly Cys Ala Gly Gly Thr Gly Gly Thr Gly Gly Cys Cys
    1715                1720                1725

Ala Thr Cys Gly Cys Cys Ala Gly Cys Ala Ala Thr Ala Thr Thr
    1730                1735                1740

Gly Gly Thr Gly Gly Cys Ala Ala Gly Cys Ala Gly Gly Cys Gly
    1745                1750                1755

Cys Thr Gly Gly Ala Gly Ala Cys Gly Gly Thr Gly Cys Ala Gly
    1760                1765                1770

Gly Cys Gly Cys Thr Gly Thr Thr Gly Cys Cys Gly Gly Thr Gly
    1775                1780                1785

Cys Thr Gly Thr Gly Cys Cys Ala Gly Gly Cys Cys Cys Ala Cys
    1790                1795                1800

Gly Gly Cys Thr Thr Gly Ala Cys Cys Cys Cys Gly Gly Ala Gly
    1805                1810                1815

Cys Ala Gly Gly Thr Gly Gly Thr Gly Gly Cys Cys Ala Thr Cys
    1820                1825                1830

Gly Cys Cys Ala Gly Cys Ala Ala Thr Gly Gly Cys Gly Gly Thr
    1835                1840                1845

Gly Gly Cys Ala Ala Gly Cys Ala Gly Gly Cys Gly Cys Thr Gly
    1850                1855                1860

Gly Ala Gly Ala Cys Gly Gly Thr Cys Cys Ala Gly Cys Gly Gly
    1865                1870                1875

Cys Thr Gly Thr Thr Gly Cys Cys Gly Gly Thr Gly Cys Thr Gly
    1880                1885                1890

Thr Gly Cys Cys Ala Gly Gly Cys Cys Cys Ala Cys Gly Gly Cys
    1895                1900                1905

Thr Thr Gly Ala Cys Cys Cys Gly Gly Ala Gly Cys Ala Gly
    1910                1915                1920

Gly Thr Gly Gly Thr Gly Gly Cys Cys Ala Thr Cys Gly Cys Cys
    1925                1930                1935

Ala Gly Cys Cys Ala Cys Gly Ala Thr Gly Gly Cys Gly Gly Cys
    1940                1945                1950

Ala Ala Gly Cys Ala Gly Gly Cys Gly Cys Thr Gly Gly Ala Gly
    1955                1960                1965

Ala Cys Gly Gly Thr Cys Cys Ala Gly Cys Gly Gly Cys Thr Gly
    1970                1975                1980

Thr Thr Gly Cys Cys Gly Gly Thr Gly Cys Thr Gly Thr Gly Cys
    1985                1990                1995

Cys Ala Gly Gly Cys Cys Cys Ala Cys Gly Gly Cys Thr Thr Gly
    2000                2005                2010

Ala Cys Cys Cys Cys Thr Cys Ala Gly Cys Ala Gly Gly Thr Gly
    2015                2020                2025

```
Gly Thr Gly Gly Cys Cys Ala Thr Cys Gly Cys Cys Ala Gly Cys
        2030                2035            2040

Ala Ala Thr Gly Gly Cys Gly Gly Cys Gly Gly Cys Ala Gly Gly
        2045                2050            2055

Cys Cys Gly Gly Cys Gly Cys Thr Gly Gly Ala Gly Ala Gly Cys
        2060                2065            2070

Ala Thr Thr Gly Thr Thr Gly Cys Cys Ala Gly Thr Thr Ala
        2075                2080            2085

Thr Cys Thr Cys Gly Cys Cys Cys Thr Gly Ala Thr Cys Cys Gly
        2090                2095            2100

Gly Cys Gly Thr Thr Gly Gly Cys Cys Gly Cys Gly Thr Thr Gly
        2105                2110            2115

Ala Cys Cys Ala Ala Cys Gly Ala Cys Cys Ala Cys Cys Thr Cys
        2120                2125            2130

Gly Thr Cys Gly Cys Cys Thr Thr Gly Gly Cys Cys Thr Gly Cys
        2135                2140            2145

Cys Thr Cys Gly Gly Cys Gly Gly Gly Cys Gly Thr Cys Cys Thr
        2150                2155            2160

Gly Cys Gly Cys Thr Gly Gly Ala Thr Gly Cys Ala Gly Thr Gly
        2165                2170            2175

Ala Ala Ala Ala Ala Gly Gly Gly Ala Thr Thr Gly Gly Gly Gly
        2180                2185            2190

Gly Ala Thr Cys Cys Thr Ala Thr Cys Ala Gly Cys Cys Gly Thr
        2195                2200            2205

Thr Cys Cys Cys Ala Gly Cys Thr Gly Gly Thr Gly Ala Ala Gly
        2210                2215            2220

Thr Cys Cys Gly Ala Gly Cys Thr Gly Gly Ala Gly Gly Ala Gly
        2225                2230            2235

Ala Ala Gly Ala Ala Ala Thr Cys Cys Gly Ala Gly Thr Thr Gly
        2240                2245            2250

Ala Gly Gly Cys Ala Cys Ala Ala Gly Cys Thr Gly Ala Ala Gly
        2255                2260            2265

Thr Ala Cys Gly Thr Gly Cys Cys Cys Ala Cys Gly Ala Ala Gly
        2270                2275            2280

Thr Ala Cys Ala Thr Cys Gly Ala Gly Cys Thr Gly Ala Thr Cys
        2285                2290            2295

Gly Ala Gly Ala Thr Cys Gly Cys Cys Gly Gly Ala Ala Ala Cys
        2300                2305            2310

Ala Gly Cys Ala Cys Cys Ala Gly Gly Ala Cys Cys Gly Thr
        2315                2320            2325

Ala Thr Cys Cys Thr Gly Gly Ala Gly Ala Thr Gly Ala Ala Gly
        2330                2335            2340

Gly Thr Gly Ala Thr Gly Gly Ala Gly Thr Thr Cys Thr Thr Cys
        2345                2350            2355

Ala Thr Gly Ala Ala Gly Gly Thr Gly Thr Ala Cys Gly Gly Cys
        2360                2365            2370

Thr Ala Cys Ala Gly Gly Gly Cys Ala Ala Gly Cys Ala Cys
        2375                2380            2385

Cys Thr Gly Gly Gly Cys Gly Gly Cys Thr Cys Cys Ala Gly Gly
        2390                2395            2400

Ala Ala Gly Cys Cys Gly Ala Cys Gly Gly Cys Gly Cys Cys
        2405                2410            2415

Ala Thr Cys Thr Ala Cys Ala Cys Cys Gly Thr Gly Gly Gly Cys
```

-continued

```
            2420                2425                 2430

Thr Cys Cys Cys Cys Cys Ala Thr Cys Gly Ala Cys Thr Ala Cys
        2435                2440                2445

Gly Gly Cys Gly Thr Gly Ala Thr Cys Gly Thr Gly Gly Ala Cys
        2450                2455                2460

Ala Cys Cys Ala Ala Gly Gly Cys Cys Thr Ala Cys Thr Cys Cys
        2465                2470                2475

Gly Gly Cys Gly Gly Cys Thr Ala Cys Ala Ala Cys Cys Thr Gly
        2480                2485                2490

Cys Cys Cys Ala Thr Cys Gly Gly Cys Cys Ala Gly Gly Cys Cys
        2495                2500                2505

Gly Ala Cys Gly Ala Ala Ala Thr Gly Cys Ala Gly Ala Gly Gly
        2510                2515                2520

Thr Ala Cys Gly Thr Gly Gly Ala Gly Gly Ala Gly Ala Ala Cys
        2525                2530                2535

Cys Ala Gly Ala Cys Cys Ala Gly Gly Ala Ala Cys Ala Ala Gly
        2540                2545                2550

Cys Ala Cys Ala Thr Cys Ala Ala Cys Cys Cys Ala Ala Cys
        2555                2560                2565

Gly Ala Gly Thr Gly Gly Thr Gly Gly Ala Ala Gly Gly Thr Gly
        2570                2575                2580

Thr Ala Cys Cys Cys Cys Thr Cys Cys Ala Gly Cys Gly Thr Gly
        2585                2590                2595

Ala Cys Cys Gly Ala Gly Thr Thr Cys Ala Ala Gly Thr Thr Cys
        2600                2605                2610

Cys Thr Gly Thr Thr Cys Gly Thr Gly Thr Cys Cys Gly Gly Cys
        2615                2620                2625

Cys Ala Cys Thr Thr Cys Ala Ala Gly Gly Gly Cys Ala Ala Cys
        2630                2635                2640

Thr Ala Cys Ala Ala Gly Gly Cys Cys Cys Ala Gly Cys Thr Gly
        2645                2650                2655

Ala Cys Cys Ala Gly Gly Cys Thr Gly Ala Ala Cys Cys Ala Cys
        2660                2665                2670

Ala Thr Cys Ala Cys Cys Ala Ala Cys Thr Gly Cys Ala Ala Cys
        2675                2680                2685

Gly Gly Cys Gly Cys Cys Gly Thr Gly Cys Thr Gly Thr Cys Cys
        2690                2695                2700

Gly Thr Gly Gly Ala Gly Gly Ala Gly Cys Thr Cys Cys Thr Gly
        2705                2710                2715

Ala Thr Cys Gly Gly Cys Gly Gly Cys Gly Ala Gly Ala Thr Gly
        2720                2725                2730

Ala Thr Cys Ala Ala Gly Gly Cys Cys Gly Gly Cys Ala Cys Cys
        2735                2740                2745

Cys Thr Gly Ala Cys Cys Thr Gly Gly Ala Gly Gly Ala Gly
        2750                2755                2760

Gly Thr Gly Ala Gly Gly Ala Gly Gly Ala Ala Gly Thr Thr Cys
        2765                2770                2775

Ala Ala Cys Ala Ala Cys Gly Gly Cys Gly Ala Gly Ala Thr Cys
        2780                2785                2790

Ala Ala Cys Thr Thr Cys Gly Cys Gly Gly Cys Cys Gly Ala Cys
        2795                2800                2805

Thr Gly Ala Thr Ala Ala
        2810
```

<210> SEQ ID NO 53
<211> LENGTH: 2832
<212> TYPE: PRT
<213> ORGANISM: Artificial sequence
<220> FEATURE:
<223> OTHER INFORMATION: polynucleotide encoding TRAC_T01-R TALEN

<400> SEQUENCE: 53

```
Ala Thr Gly Gly Gly Cys Gly Ala Thr Cys Cys Thr Ala Ala Ala
 1               5                   10                  15

Ala Gly Ala Ala Ala Cys Gly Thr Ala Ala Gly Gly Thr Cys Ala Thr
                20                  25                  30

Cys Gly Ala Thr Ala Ala Gly Gly Ala Gly Ala Cys Cys Gly Cys Cys
                35                  40                  45

Gly Cys Thr Gly Cys Cys Ala Ala Gly Thr Thr Cys Gly Ala Gly Ala
            50                  55                  60

Gly Ala Cys Ala Gly Cys Ala Cys Ala Thr Gly Gly Ala Cys Ala Gly
65                  70                  75                  80

Cys Ala Thr Cys Gly Ala Thr Ala Thr Cys Gly Cys Cys Gly Ala Thr
                85                  90                  95

Cys Thr Ala Cys Gly Cys Ala Cys Gly Cys Thr Cys Gly Gly Cys Thr
                100                 105                 110

Ala Cys Ala Gly Cys Cys Ala Gly Cys Ala Gly Cys Ala Ala Cys Ala
            115                 120                 125

Gly Gly Ala Gly Ala Ala Gly Ala Thr Cys Ala Ala Ala Cys Cys Gly
        130                 135                 140

Ala Ala Gly Gly Thr Thr Cys Gly Thr Thr Cys Gly Ala Cys Ala Gly
145                 150                 155                 160

Thr Gly Gly Cys Gly Cys Ala Gly Cys Ala Cys Cys Ala Cys Gly Ala
                165                 170                 175

Gly Gly Cys Ala Cys Thr Gly Gly Thr Cys Gly Gly Cys Cys Ala Cys
                180                 185                 190

Gly Gly Gly Thr Thr Thr Ala Cys Ala Cys Ala Cys Gly Cys Gly Cys
            195                 200                 205

Ala Cys Ala Thr Cys Gly Thr Thr Gly Cys Gly Thr Thr Ala Ala Gly
        210                 215                 220

Cys Cys Ala Ala Cys Ala Cys Cys Gly Gly Cys Ala Gly Cys Gly Gly
225                 230                 235                 240

Thr Thr Ala Gly Gly Ala Cys Cys Gly Thr Cys Gly Cys Thr Gly Gly
                245                 250                 255

Thr Cys Ala Ala Gly Thr Ala Thr Cys Ala Gly Gly Ala Cys Ala Thr
                260                 265                 270

Gly Ala Thr Cys Gly Cys Ala Gly Cys Gly Thr Thr Gly Cys Cys Ala
            275                 280                 285

Gly Ala Gly Gly Cys Gly Ala Cys Ala Cys Gly Ala Ala Gly Gly Gly
        290                 295                 300

Cys Gly Ala Thr Cys Gly Thr Thr Gly Gly Cys Gly Thr Cys Gly Gly
305                 310                 315                 320

Cys Ala Ala Ala Cys Ala Gly Thr Gly Gly Thr Cys Cys Gly Gly Cys
                325                 330                 335

Gly Cys Ala Cys Gly Cys Gly Cys Thr Cys Thr Gly Ala Gly Gly Gly
                340                 345                 350

Cys Cys Thr Thr Gly Cys Thr Cys Ala Cys Gly Gly Thr Gly Gly Cys
            355                 360                 365
```

```
Gly Gly Gly Ala Gly Ala Gly Thr Thr Gly Ala Gly Ala Gly Gly Thr
        370                 375                 380
Cys Cys Ala Cys Cys Gly Thr Thr Ala Cys Ala Gly Thr Thr Gly Gly
385                 390                 395                 400
Ala Cys Ala Cys Ala Gly Gly Cys Cys Ala Ala Cys Thr Thr Cys Thr
                405                 410                 415
Cys Ala Ala Gly Ala Thr Thr Gly Cys Ala Ala Ala Cys Gly Thr
            420                 425                 430
Gly Gly Cys Gly Gly Cys Gly Thr Gly Ala Cys Cys Gly Cys Ala Gly
            435                 440                 445
Thr Gly Gly Ala Gly Gly Cys Ala Gly Thr Gly Cys Ala Thr Gly Cys
    450                 455                 460
Ala Thr Gly Gly Cys Gly Cys Ala Ala Thr Gly Cys Ala Cys Thr Gly
465                 470                 475                 480
Ala Cys Gly Gly Thr Gly Cys Cys Cys Gly Cys Thr Cys Ala
                485                 490                 495
Ala Cys Thr Thr Gly Ala Cys Cys Cys Gly Gly Ala Gly Cys Ala
            500                 505                 510
Gly Gly Thr Gly Gly Thr Gly Gly Cys Cys Ala Thr Cys Gly Cys Cys
            515                 520                 525
Ala Gly Cys Cys Ala Cys Gly Ala Thr Gly Gly Cys Gly Gly Cys Ala
530                 535                 540
Ala Gly Cys Ala Gly Gly Cys Gly Cys Thr Gly Gly Ala Gly Ala Cys
545                 550                 555                 560
Gly Gly Thr Cys Cys Ala Gly Cys Gly Gly Cys Thr Gly Thr Thr Gly
                565                 570                 575
Cys Cys Gly Gly Thr Gly Cys Thr Gly Thr Gly Cys Cys Ala Gly Gly
            580                 585                 590
Cys Cys Cys Ala Cys Gly Gly Cys Thr Thr Gly Ala Cys Cys Cys
            595                 600                 605
Cys Cys Ala Gly Cys Ala Gly Gly Thr Gly Gly Thr Gly Gly Cys Cys
    610                 615                 620
Ala Thr Cys Gly Cys Cys Ala Gly Cys Ala Thr Gly Gly Cys Gly
625                 630                 635                 640
Gly Thr Gly Gly Cys Ala Ala Gly Cys Ala Gly Gly Cys Gly Cys Thr
            645                 650                 655
Gly Gly Ala Gly Ala Cys Gly Gly Thr Cys Cys Ala Gly Cys Gly Gly
            660                 665                 670
Cys Thr Gly Thr Thr Gly Cys Cys Gly Gly Thr Gly Cys Thr Gly Thr
        675                 680                 685
Gly Cys Cys Ala Gly Gly Cys Cys Cys Ala Cys Gly Cys Thr Thr
    690                 695                 700
Gly Ala Cys Cys Cys Gly Gly Ala Gly Cys Ala Gly Gly Thr Gly
705                 710                 715                 720
Gly Thr Gly Gly Cys Cys Ala Thr Cys Gly Cys Cys Ala Gly Cys
                725                 730                 735
Ala Cys Gly Ala Thr Gly Gly Cys Gly Gly Cys Ala Ala Gly Cys Ala
            740                 745                 750
Gly Gly Cys Gly Cys Thr Gly Gly Ala Gly Ala Cys Gly Gly Thr Cys
            755                 760                 765
Cys Ala Gly Cys Gly Gly Cys Thr Gly Thr Thr Gly Cys Cys Gly Gly
    770                 775                 780
```

```
Thr Gly Cys Thr Gly Thr Gly Cys Cys Ala Gly Cys Cys Cys Ala
785                 790                 795                 800

Cys Gly Gly Cys Thr Thr Gly Ala Cys Cys Cys Gly Gly Ala Gly
            805                 810                 815

Cys Ala Gly Gly Thr Gly Gly Thr Gly Gly Cys Cys Ala Thr Cys Gly
                820                 825                 830

Cys Cys Ala Gly Cys Ala Ala Thr Ala Thr Thr Gly Gly Thr Gly Gly
        835                 840                 845

Cys Ala Ala Gly Cys Ala Gly Gly Cys Gly Cys Thr Gly Gly Ala Gly
    850                 855                 860

Ala Cys Gly Gly Thr Gly Cys Ala Gly Gly Cys Gly Cys Thr Gly Thr
865                 870                 875                 880

Thr Gly Cys Cys Gly Gly Thr Gly Cys Thr Gly Thr Gly Cys Cys Ala
                885                 890                 895

Gly Gly Cys Cys Cys Ala Cys Gly Gly Cys Thr Thr Gly Ala Cys Cys
            900                 905                 910

Cys Cys Cys Cys Ala Gly Cys Ala Gly Gly Thr Gly Gly Thr Gly Gly
        915                 920                 925

Cys Cys Ala Thr Cys Gly Cys Cys Ala Gly Cys Ala Ala Thr Ala Ala
    930                 935                 940

Thr Gly Gly Thr Gly Gly Cys Ala Ala Gly Cys Ala Gly Gly Cys Gly
945                 950                 955                 960

Cys Thr Gly Gly Ala Gly Ala Cys Gly Gly Thr Cys Cys Ala Gly Cys
                965                 970                 975

Gly Gly Cys Thr Gly Thr Thr Gly Cys Cys Gly Gly Thr Gly Cys Thr
            980                 985                 990

Gly Thr Gly Cys Cys Ala Gly Gly Cys Cys Cys Ala Cys Gly Gly Cys
        995                 1000                1005

Thr Thr Gly Ala Cys Cys Cys Cys Gly Gly Ala Gly Cys Ala Gly
    1010                1015                1020

Gly Thr Gly Gly Thr Gly Gly Cys Cys Ala Thr Cys Gly Cys Cys
    1025                1030                1035

Ala Gly Cys Cys Ala Cys Gly Ala Thr Gly Gly Cys Gly Gly Cys
    1040                1045                1050

Ala Ala Gly Cys Ala Gly Gly Cys Gly Cys Thr Gly Gly Ala Gly
    1055                1060                1065

Ala Cys Gly Gly Thr Cys Cys Ala Gly Cys Gly Gly Cys Thr Gly
    1070                1075                1080

Thr Thr Gly Cys Cys Gly Gly Thr Gly Cys Thr Gly Thr Gly Cys
    1085                1090                1095

Cys Ala Gly Gly Cys Cys Cys Ala Cys Gly Gly Cys Thr Thr Gly
    1100                1105                1110

Ala Cys Cys Cys Cys Cys Ala Gly Cys Ala Gly Gly Thr Gly Gly
    1115                1120                1125

Thr Gly Gly Cys Cys Ala Thr Cys Gly Cys Cys Ala Gly Cys
    1130                1135                1140

Ala Ala Thr Gly Gly Cys Gly Gly Thr Gly Gly Cys Ala Ala Gly
    1145                1150                1155

Cys Ala Gly Gly Cys Gly Cys Thr Gly Gly Ala Gly Ala Cys Gly
    1160                1165                1170

Gly Thr Cys Cys Ala Gly Cys Gly Gly Cys Thr Gly Thr Thr Gly
    1175                1180                1185

Cys Cys Gly Gly Thr Gly Cys Thr Gly Thr Gly Cys Cys Ala Gly
```

-continued

```
             1190                1195                1200
Gly Cys Cys Cys Ala Cys Gly Gly Cys Thr Thr Gly Ala Cys Cys
             1205                1210                1215
Cys Cys Cys Cys Ala Gly Cys Ala Gly Gly Thr Gly Gly Thr Gly
             1220                1225                1230
Gly Cys Cys Ala Thr Cys Gly Cys Cys Ala Gly Cys Ala Ala Thr
             1235                1240                1245
Ala Ala Thr Gly Gly Thr Gly Gly Cys Ala Ala Gly Cys Ala Gly
             1250                1255                1260
Gly Cys Gly Cys Thr Gly Gly Ala Gly Ala Cys Gly Gly Thr Cys
             1265                1270                1275
Cys Ala Gly Cys Gly Gly Cys Thr Gly Thr Thr Gly Cys Cys Gly
             1280                1285                1290
Gly Thr Gly Cys Thr Gly Thr Gly Cys Cys Ala Gly Gly Cys Cys
             1295                1300                1305
Cys Ala Cys Gly Gly Cys Thr Thr Gly Ala Cys Cys Cys Cys Cys
             1310                1315                1320
Cys Ala Gly Cys Ala Gly Gly Thr Gly Thr Gly Gly Cys Cys
             1325                1330                1335
Ala Thr Cys Gly Cys Cys Ala Gly Cys Ala Ala Thr Ala Ala Thr
             1340                1345                1350
Gly Gly Thr Gly Gly Cys Ala Ala Gly Cys Ala Gly Gly Cys Gly
             1355                1360                1365
Cys Thr Gly Gly Ala Gly Ala Cys Gly Gly Thr Cys Cys Ala Gly
             1370                1375                1380
Cys Gly Gly Cys Thr Gly Thr Thr Gly Cys Cys Gly Gly Thr Gly
             1385                1390                1395
Cys Thr Gly Thr Gly Cys Cys Ala Gly Gly Cys Cys Cys Ala Cys
             1400                1405                1410
Gly Gly Cys Thr Thr Gly Ala Cys Cys Cys Cys Cys Cys Ala Gly
             1415                1420                1425
Cys Ala Gly Gly Thr Gly Thr Gly Gly Cys Cys Ala Thr Cys
             1430                1435                1440
Gly Cys Cys Ala Gly Cys Ala Ala Thr Gly Gly Cys Gly Gly Thr
             1445                1450                1455
Gly Gly Cys Ala Ala Gly Cys Ala Gly Gly Cys Gly Cys Thr Gly
             1460                1465                1470
Gly Ala Gly Ala Cys Gly Gly Thr Cys Cys Ala Gly Cys Gly Gly
             1475                1480                1485
Cys Thr Gly Thr Thr Gly Cys Cys Gly Gly Thr Gly Cys Thr Gly
             1490                1495                1500
Thr Gly Cys Cys Ala Gly Gly Cys Cys Cys Ala Cys Gly Gly Cys
             1505                1510                1515
Thr Thr Gly Ala Cys Cys Cys Gly Gly Ala Gly Cys Ala Gly
             1520                1525                1530
Gly Thr Gly Gly Thr Gly Gly Cys Cys Ala Thr Cys Gly Cys Cys
             1535                1540                1545
Ala Gly Cys Ala Ala Thr Ala Thr Thr Gly Gly Thr Gly Gly Cys
             1550                1555                1560
Ala Ala Gly Cys Ala Gly Gly Cys Gly Cys Thr Gly Gly Ala Gly
             1565                1570                1575
Ala Cys Gly Gly Thr Gly Cys Ala Gly Gly Cys Gly Cys Thr Gly
             1580                1585                1590
```

```
Thr Thr Gly Cys Cys Gly Gly Thr Gly Cys Thr Gly Thr Gly Cys
1595                 1600                1605

Cys Ala Gly Gly Cys Cys Cys Ala Cys Gly Gly Cys Thr Thr Gly
1610                 1615                1620

Ala Cys Cys Cys Cys Gly Gly Ala Gly Cys Ala Gly Gly Thr Gly
1625                 1630                1635

Gly Thr Gly Gly Cys Cys Ala Thr Cys Gly Cys Cys Ala Gly Cys
1640                 1645                1650

Cys Ala Cys Gly Ala Thr Gly Gly Cys Gly Gly Cys Ala Ala Gly
1655                 1660                1665

Cys Ala Gly Gly Cys Gly Cys Thr Gly Gly Ala Gly Ala Cys Gly
1670                 1675                1680

Gly Thr Cys Cys Ala Gly Cys Gly Gly Cys Thr Gly Thr Thr Gly
1685                 1690                1695

Cys Cys Gly Gly Thr Gly Cys Thr Gly Thr Gly Cys Cys Ala Gly
1700                 1705                1710

Gly Cys Cys Cys Ala Cys Gly Gly Cys Thr Thr Gly Ala Cys Cys
1715                 1720                1725

Cys Cys Gly Gly Ala Gly Cys Ala Gly Gly Thr Gly Gly Thr Gly
1730                 1735                1740

Gly Cys Cys Ala Thr Cys Gly Cys Cys Ala Gly Cys Ala Ala Thr
1745                 1750                1755

Ala Thr Thr Gly Gly Thr Gly Gly Cys Ala Ala Gly Cys Ala Gly
1760                 1765                1770

Gly Cys Gly Cys Thr Gly Gly Ala Gly Ala Cys Gly Gly Thr Gly
1775                 1780                1785

Cys Ala Gly Gly Cys Gly Cys Thr Gly Thr Thr Gly Cys Cys Gly
1790                 1795                1800

Gly Thr Gly Cys Thr Gly Thr Gly Cys Cys Ala Gly Gly Cys Cys
1805                 1810                1815

Cys Ala Cys Gly Gly Cys Thr Thr Gly Ala Cys Cys Cys Cys Gly
1820                 1825                1830

Gly Ala Gly Cys Ala Gly Gly Thr Gly Gly Thr Gly Gly Cys Cys
1835                 1840                1845

Ala Thr Cys Gly Cys Cys Ala Gly Cys Cys Ala Cys Gly Ala Thr
1850                 1855                1860

Gly Gly Cys Gly Gly Cys Ala Ala Gly Cys Ala Gly Gly Cys Gly
1865                 1870                1875

Cys Thr Gly Gly Ala Gly Ala Cys Gly Gly Thr Gly Cys Ala Gly
1880                 1885                1890

Cys Gly Gly Cys Thr Gly Thr Thr Gly Cys Cys Gly Gly Thr Gly
1895                 1900                1905

Cys Thr Gly Thr Gly Cys Cys Ala Gly Gly Cys Cys Cys Ala Cys
1910                 1915                1920

Gly Gly Cys Thr Thr Gly Ala Cys Cys Cys Cys Cys Cys Ala Gly
1925                 1930                1935

Cys Ala Gly Gly Thr Gly Gly Thr Gly Gly Cys Cys Ala Thr Cys
1940                 1945                1950

Gly Cys Cys Ala Gly Cys Ala Ala Thr Ala Ala Thr Gly Gly Thr
1955                 1960                1965

Gly Gly Cys Ala Ala Gly Cys Ala Gly Gly Cys Gly Cys Thr Gly
1970                 1975                1980
```

```
Gly Ala Gly Ala Cys Gly Gly Thr Cys Cys Ala Gly Cys Gly Gly
    1985                1990                1995

Cys Thr Gly Thr Thr Gly Cys Cys Gly Gly Thr Gly Cys Thr Gly
    2000                2005                2010

Thr Gly Cys Cys Ala Gly Gly Cys Cys Cys Ala Cys Gly Gly Cys
    2015                2020                2025

Thr Thr Gly Ala Cys Cys Cys Cys Thr Cys Ala Gly Cys Ala Gly
    2030                2035                2040

Gly Thr Gly Gly Thr Gly Gly Cys Cys Ala Thr Cys Gly Cys Cys
    2045                2050                2055

Ala Gly Cys Ala Ala Thr Gly Gly Cys Gly Gly Cys Gly Gly Cys
    2060                2065                2070

Ala Gly Gly Cys Cys Gly Gly Cys Gly Cys Thr Gly Gly Ala Gly
    2075                2080                2085

Ala Gly Cys Ala Thr Thr Gly Thr Thr Gly Cys Cys Cys Ala Gly
    2090                2095                2100

Thr Thr Ala Thr Cys Thr Cys Gly Cys Cys Cys Thr Gly Ala Thr
    2105                2110                2115

Cys Cys Gly Gly Cys Gly Thr Thr Gly Gly Cys Cys Gly Cys Gly
    2120                2125                2130

Thr Thr Gly Ala Cys Ala Ala Cys Gly Ala Cys Cys Ala Cys Cys
    2135                2140                2145

Cys Thr Cys Gly Thr Cys Gly Cys Cys Thr Thr Gly Gly Cys Cys
    2150                2155                2160

Thr Gly Cys Cys Thr Cys Gly Gly Cys Gly Gly Gly Cys Gly Thr
    2165                2170                2175

Cys Cys Thr Gly Cys Gly Cys Thr Gly Gly Ala Thr Gly Cys Ala
    2180                2185                2190

Gly Thr Gly Ala Ala Ala Ala Ala Gly Gly Ala Thr Thr Gly
    2195                2200                2205

Gly Gly Gly Gly Ala Thr Cys Cys Thr Ala Thr Cys Ala Gly Cys
    2210                2215                2220

Cys Gly Thr Thr Cys Cys Ala Gly Cys Thr Gly Gly Thr Gly
    2225                2230                2235

Ala Ala Gly Thr Cys Cys Gly Ala Gly Cys Thr Gly Gly Ala Gly
    2240                2245                2250

Gly Ala Gly Ala Ala Gly Ala Ala Ala Thr Cys Cys Gly Ala Gly
    2255                2260                2265

Thr Thr Gly Ala Gly Gly Cys Ala Cys Ala Ala Gly Cys Thr Gly
    2270                2275                2280

Ala Ala Gly Thr Ala Cys Gly Thr Gly Cys Cys Cys Cys Ala Cys
    2285                2290                2295

Gly Ala Gly Thr Ala Cys Ala Thr Cys Gly Ala Gly Cys Thr Gly
    2300                2305                2310

Ala Thr Cys Gly Ala Gly Ala Thr Cys Gly Cys Cys Cys Gly Gly
    2315                2320                2325

Ala Ala Cys Ala Gly Cys Ala Cys Cys Cys Ala Gly Gly Ala Cys
    2330                2335                2340

Cys Gly Thr Ala Thr Cys Cys Thr Gly Gly Ala Gly Ala Thr Gly
    2345                2350                2355

Ala Ala Gly Gly Thr Gly Ala Thr Gly Gly Ala Gly Thr Thr Cys
    2360                2365                2370

Thr Thr Cys Ala Thr Gly Ala Ala Gly Gly Thr Gly Thr Ala Cys
```

```
    2375                2380                2385

Gly Gly  Cys Thr Ala Cys Ala  Gly Gly Gly Gly Cys  Ala Ala Gly
    2390                2395                2400

Cys Ala  Cys Cys Thr Gly Gly  Gly Cys Gly Gly Cys  Thr Cys Cys
    2405                2410                2415

Ala Gly  Gly Ala Ala Gly Cys  Cys Cys Gly Ala Cys  Gly Gly Cys
    2420                2425                2430

Gly Cys  Cys Ala Thr Cys Thr  Ala Cys Ala Cys Cys  Gly Thr Gly
    2435                2440                2445

Gly Gly  Cys Thr Cys Cys Cys  Cys Cys Ala Thr Cys  Gly Ala Cys
    2450                2455                2460

Thr Ala  Cys Gly Gly Cys Gly  Thr Gly Ala Thr Cys  Gly Thr Gly
    2465                2470                2475

Gly Ala  Cys Ala Cys Cys Ala  Ala Gly Gly Cys Cys  Thr Ala Cys
    2480                2485                2490

Thr Cys  Cys Gly Gly Cys Gly  Gly Cys Thr Ala Cys  Ala Ala Cys
    2495                2500                2505

Cys Thr  Gly Cys Cys Cys Ala  Thr Cys Gly Gly Cys  Cys Ala Gly
    2510                2515                2520

Gly Cys  Cys Gly Ala Cys Gly  Ala Ala Ala Thr Gly  Cys Ala Gly
    2525                2530                2535

Ala Gly  Gly Thr Ala Cys Gly  Thr Gly Gly Ala Gly  Gly Ala Gly
    2540                2545                2550

Ala Ala  Cys Cys Ala Gly Ala  Cys Cys Ala Gly Gly  Ala Ala Cys
    2555                2560                2565

Ala Ala  Gly Cys Ala Cys Ala  Thr Cys Ala Ala Cys  Cys Cys Cys
    2570                2575                2580

Ala Ala  Cys Gly Ala Gly Thr  Gly Gly Thr Gly Gly  Ala Ala Gly
    2585                2590                2595

Gly Thr  Gly Thr Ala Cys Cys  Cys Cys Thr Cys Cys  Ala Gly Cys
    2600                2605                2610

Gly Thr  Gly Ala Cys Cys Gly  Ala Gly Thr Thr Cys  Ala Ala Gly
    2615                2620                2625

Thr Thr  Cys Cys Thr Gly Thr  Thr Cys Gly Thr Gly  Thr Cys Cys
    2630                2635                2640

Gly Gly  Cys Cys Ala Cys Thr  Thr Cys Ala Ala Gly  Gly Gly Cys
    2645                2650                2655

Ala Ala  Cys Thr Ala Cys Ala  Ala Gly Gly Cys Cys  Cys Ala Gly
    2660                2665                2670

Cys Thr  Gly Ala Cys Cys Ala  Gly Gly Cys Thr Gly  Ala Ala Cys
    2675                2680                2685

Cys Ala  Cys Ala Thr Cys Ala  Cys Cys Ala Ala Cys  Thr Gly Cys
    2690                2695                2700

Ala Ala  Cys Gly Gly Cys Gly  Cys Cys Gly Thr Gly  Cys Thr Gly
    2705                2710                2715

Thr Cys  Cys Gly Thr Gly Gly  Ala Gly Gly Ala Gly  Cys Thr Cys
    2720                2725                2730

Cys Thr  Gly Ala Thr Cys Gly  Gly Cys Gly Gly Cys  Gly Ala Gly
    2735                2740                2745

Ala Thr  Gly Ala Thr Cys Ala  Ala Gly Gly Cys Cys  Gly Gly Cys
    2750                2755                2760

Ala Cys  Cys Cys Thr Gly Ala  Cys Cys Cys Thr Gly  Gly Ala Gly
    2765                2770                2775
```

Gly Ala Gly Gly Thr Gly Ala Gly Gly Ala Gly Ala Ala Gly
        2780            2785                2790

Thr Thr Cys Ala Ala Cys Ala Ala Cys Gly Gly Cys Gly Ala Gly
    2795            2800                2805

Ala Thr Cys Ala Ala Cys Thr Thr Cys Gly Cys Gly Gly Cys Cys
    2810            2815                2820

Gly Ala Cys Thr Gly Ala Thr Ala Ala
    2825            2830

<210> SEQ ID NO 54
<211> LENGTH: 113
<212> TYPE: PRT
<213> ORGANISM: Artificial sequence
<220> FEATURE:
<223> OTHER INFORMATION: Humanized scFv Klon43 Variant VL1

<400> SEQUENCE: 54

Met Ala Asp Tyr Lys Asp Ile Val Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Ala Leu Ile Tyr Ser Ala Ser Tyr Arg Tyr Ser Gly Val Pro
    50                  55                  60

Ser Arg Phe Ser Gly Arg Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg

<210> SEQ ID NO 55
<211> LENGTH: 113
<212> TYPE: PRT
<213> ORGANISM: Artificial sequence
<220> FEATURE:
<223> OTHER INFORMATION: Humanized scFv Klon43 Variant VL2

<400> SEQUENCE: 55

Met Ala Asp Tyr Lys Asp Ile Gln Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Ala Leu Ile Tyr Ser Ala Ser Tyr Arg Tyr Ser Gly Val Pro
    50                  55                  60

Ser Arg Phe Ser Gly Arg Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg

```
<210> SEQ ID NO 56
<211> LENGTH: 113
<212> TYPE: PRT
<213> ORGANISM: Artificial sequence
<220> FEATURE:
<223> OTHER INFORMATION: Humanized scFv Klon43 Variant VL3

<400> SEQUENCE: 56

Met Ala Asp Tyr Lys Asp Ile Gln Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Ala Leu Ile Tyr Ser Ala Ser Tyr Arg Tyr Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg

<210> SEQ ID NO 57
<211> LENGTH: 113
<212> TYPE: PRT
<213> ORGANISM: Artificial sequence
<220> FEATURE:
<223> OTHER INFORMATION: Humanized scFv Klon43 Variant VL4

<400> SEQUENCE: 57

Met Ala Asp Tyr Lys Asp Ile Gln Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Leu Leu Ile Tyr Ser Ala Ser Tyr Arg Tyr Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg

<210> SEQ ID NO 58
<211> LENGTH: 113
<212> TYPE: PRT
<213> ORGANISM: Artificial sequence
<220> FEATURE:
<223> OTHER INFORMATION: Humanized scFv Klon43 Variant VL5

<400> SEQUENCE: 58

Met Ala Asp Tyr Lys Asp Ile Gln Met Thr Gln Ser Pro Ser Ser Val
1               5                   10                  15
```

```
Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Leu Leu Ile Tyr Ser Ala Ser Tyr Arg Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg
```

<210> SEQ ID NO 59
<211> LENGTH: 113
<212> TYPE: PRT
<213> ORGANISM: Artificial sequence
<220> FEATURE:
<223> OTHER INFORMATION: Humanized scFv Klon43 Variant VL6

<400> SEQUENCE: 59

```
Met Ala Asp Tyr Lys Asp Ile Gln Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Leu Leu Ile Tyr Ser Ala Ser Tyr Gly Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg
```

<210> SEQ ID NO 60
<211> LENGTH: 127
<212> TYPE: PRT
<213> ORGANISM: Artificial sequence
<220> FEATURE:
<223> OTHER INFORMATION: Humanized scFv Klon43 variant VH1

<400> SEQUENCE: 60

```
Glu Val Lys Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Leu Ile Arg Ser Lys Ala Asp Gly Tyr Thr Thr Glu Tyr Ser Ala
    50                  55                  60

Ser Val Lys Gly Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Val Tyr
```

85                  90                  95

Tyr Cys Ala Arg Asp Ala Ala Tyr Tyr Ser Tyr Tyr Ser Pro Glu Gly
                100                 105                 110

Ala Met Asp Tyr Trp Gly Gln Gly Thr Leu Val Thr Val Ser Ser
        115                 120                 125

<210> SEQ ID NO 61
<211> LENGTH: 127
<212> TYPE: PRT
<213> ORGANISM: Artificial sequence
<220> FEATURE:
<223> OTHER INFORMATION: Humanized scFv Klon43 variant VH2

<400> SEQUENCE: 61

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
                20                  25                  30

Tyr Met Ser Trp Val Arg Gln Ala Pro Gly Lys Gly Leu Glu Trp Val
            35                  40                  45

Gly Leu Ile Arg Ser Lys Ala Asp Gly Tyr Thr Thr Glu Tyr Ser Ala
50                  55                  60

Ser Val Lys Gly Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Val Tyr
                85                  90                  95

Tyr Cys Ala Arg Asp Ala Ala Tyr Tyr Ser Tyr Tyr Ser Pro Glu Gly
                100                 105                 110

Ala Met Asp Tyr Trp Gly Gln Gly Thr Leu Val Thr Val Ser Ser
        115                 120                 125

<210> SEQ ID NO 62
<211> LENGTH: 127
<212> TYPE: PRT
<213> ORGANISM: Artificial sequence
<220> FEATURE:
<223> OTHER INFORMATION: Humanized scFv Klon43 variant VH3

<400> SEQUENCE: 62

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
                20                  25                  30

Tyr Met Ser Trp Val Arg Gln Ala Pro Gly Lys Gly Leu Glu Trp Val
            35                  40                  45

Gly Leu Ile Arg Ser Lys Ala Asp Gly Tyr Thr Thr Glu Tyr Ser Ala
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Ala Ala Tyr Tyr Ser Tyr Tyr Ser Pro Glu Gly
                100                 105                 110

Ala Met Asp Tyr Trp Gly Gln Gly Thr Leu Val Thr Val Ser Ser
        115                 120                 125

<210> SEQ ID NO 63
<211> LENGTH: 127

<212> TYPE: PRT
<213> ORGANISM: Artificial sequence
<220> FEATURE:
<223> OTHER INFORMATION: Humanized scFv Klon43 variant VH4

<400> SEQUENCE: 63

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Ser Lys Ala Asp Gly Tyr Thr Thr Glu Tyr Ser Ala
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Leu Val Thr Val Ser Ser
        115                 120                 125

<210> SEQ ID NO 64
<211> LENGTH: 127
<212> TYPE: PRT
<213> ORGANISM: Artificial sequence
<220> FEATURE:
<223> OTHER INFORMATION: Humanized scFv Klon43 variant VH5

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Ser Lys Ala Asp Gly Tyr Thr Thr Glu Tyr Ala Ala
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Ala Ala Tyr Tyr Ser Tyr Tyr Ser Pro Glu Gly
            100                 105                 110

Ala Met Asp Tyr Trp Gly Gln Gly Thr Leu Val Thr Val Ser Ser
        115                 120                 125

<210> SEQ ID NO 65
<211> LENGTH: 127
<212> TYPE: PRT
<213> ORGANISM: Artificial sequence
<220> FEATURE:
<223> OTHER INFORMATION: Humanized scFv Klon43 variant VH6

<400> SEQUENCE: 65

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr

```
                  20                  25                  30
Tyr Met Ser Trp Val Arg Gln Ala Pro Gly Lys Gly Leu Glu Trp Val
                  35                  40                  45
Gly Leu Ile Arg Ser Lys Ala Asp Gly Tyr Thr Thr Glu Tyr Ala Ala
            50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Lys Thr Glu Asp Thr Ala Val Tyr
                    85                  90                  95
Tyr Cys Ala Arg Asp Ala Ala Tyr Tyr Ser Tyr Tyr Ser Pro Glu Gly
                100                 105                 110
Ala Met Asp Tyr Trp Gly Gln Gly Thr Leu Val Thr Val Ser Ser
            115                 120                 125

<210> SEQ ID NO 66
<211> LENGTH: 127
<212> TYPE: PRT
<213> ORGANISM: Artificial sequence
<220> FEATURE:
<223> OTHER INFORMATION: Humanized scFv Klon43 variant VH7

<400> SEQUENCE: 66

Glu Val Gln Leu Val Glu Ser Gly Gly Gly Leu Val Gln Pro Gly Arg
1               5                   10                  15
Ser Leu Arg Leu Ser Cys Thr Ala Ser Gly Phe Thr Phe Thr Asp Tyr
                  20                  25                  30
Tyr Met Ser Trp Val Arg Gln Ala Pro Gly Lys Gly Leu Glu Trp Val
                  35                  40                  45
Gly Phe Ile Arg Ser Lys Ala Asp Gly Tyr Thr Thr Glu Tyr Ala Ala
            50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Lys Thr Glu Asp Thr Ala Val Tyr
                    85                  90                  95
Tyr Cys Thr Arg Asp Ala Ala Tyr Tyr Ser Tyr Tyr Ser Pro Glu Gly
                100                 105                 110
Ala Met Asp Tyr Trp Gly Gln Gly Thr Leu Val Thr Val Ser Ser
            115                 120                 125

<210> SEQ ID NO 67
<211> LENGTH: 8
<212> TYPE: PRT
<213> ORGANISM: Artificial sequence
<220> FEATURE:
<223> OTHER INFORMATION: CDR1

<400> SEQUENCE: 67

Gly Phe Thr Phe Thr Asp Tyr Tyr
1               5

<210> SEQ ID NO 68
<211> LENGTH: 9
<212> TYPE: PRT
<213> ORGANISM: Artificial sequence
<220> FEATURE:
<223> OTHER INFORMATION: CDR2

<400> SEQUENCE: 68

Arg Ser Lys Ala Asp Gly Tyr Thr Thr
1               5
```

```
<210> SEQ ID NO 69
<211> LENGTH: 18
<212> TYPE: PRT
<213> ORGANISM: Artificial sequence
<220> FEATURE:
<223> OTHER INFORMATION: CDR3

<400> SEQUENCE: 69

Ala Arg Asp Ala Ala Tyr Tyr Ser Tyr Tyr Ser Pro Glu Gly Ala Met
1               5                   10                  15

Asp Tyr

<210> SEQ ID NO 70
<211> LENGTH: 6
<212> TYPE: PRT
<213> ORGANISM: Artificial sequence
<220> FEATURE:
<223> OTHER INFORMATION: CDR4

<400> SEQUENCE: 70

Gln Asn Val Asp Ser Ala
1               5

<210> SEQ ID NO 71
<211> LENGTH: 3
<212> TYPE: PRT
<213> ORGANISM: Artificial Sequence
<220> FEATURE:
<223> OTHER INFORMATION: CDR5

<400> SEQUENCE: 71

Ser Ala Ser
1

<210> SEQ ID NO 72
<211> LENGTH: 9
<212> TYPE: PRT
<213> ORGANISM: Artificial sequence
<220> FEATURE:
<223> OTHER INFORMATION: CDR6

<400> SEQUENCE: 72

Gln Gln Tyr Tyr Ser Thr Pro Trp Thr
1               5

<210> SEQ ID NO 73
<211> LENGTH: 117
<212> TYPE: PRT
<213> ORGANISM: Artificial sequence
<220> FEATURE:
<223> OTHER INFORMATION: hVH Klo43-3 generic
<220> FEATURE:
<221> NAME/KEY: misc_feature
<222> LOCATION: (1)..(25)
<223> OTHER INFORMATION: Any amino acid
<220> FEATURE:
<221> NAME/KEY: misc_feature
<222> LOCATION: (34)..(50)
<223> OTHER INFORMATION: Any amino acid
<220> FEATURE:
<221> NAME/KEY: misc_feature
<222> LOCATION: (61)..(88)
<223> OTHER INFORMATION: Any amino acid
<220> FEATURE:
<221> NAME/KEY: misc_feature
<222> LOCATION: (107)..(117)
<223> OTHER INFORMATION: Any amino acid
```

<400> SEQUENCE: 73

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Gly Phe Thr Phe Thr Asp Tyr
            20                  25                  30

Tyr Xaa Xaa Xaa Xaa Xaa Xaa Xaa Xaa Xaa Xaa Xaa Xaa Xaa Xaa
        35                  40                  45

Xaa Xaa Ile Arg Ser Lys Ala Asp Gly Tyr Thr Thr Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Ala Arg Asp Ala Ala Tyr Tyr Ser
                85                  90                  95

Tyr Tyr Ser Pro Glu Gly Ala Met Asp Tyr Xaa Xaa Xaa Xaa Xaa
                100                 105                 110

Xaa Xaa Xaa Xaa Xaa
        115
```

<210> SEQ ID NO 74
<211> LENGTH: 111
<212> TYPE: PRT
<213> ORGANISM: Artificial sequence
<220> FEATURE:
<223> OTHER INFORMATION: hVL Klo43-3 generic
<220> FEATURE:
<221> NAME/KEY: misc_feature
<222> LOCATION: (1)..(31)
<223> OTHER INFORMATION: Any amino acid
<220> FEATURE:
<221> NAME/KEY: misc_feature
<222> LOCATION: (38)..(54)
<223> OTHER INFORMATION: Any amino acid
<220> FEATURE:
<221> NAME/KEY: misc_feature
<222> LOCATION: (58)..(93)
<223> OTHER INFORMATION: Any amino acid
<220> FEATURE:
<221> NAME/KEY: misc_feature
<222> LOCATION: (103)..(111)
<223> OTHER INFORMATION: Any amino acid

<400> SEQUENCE: 74

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Gln
            20                  25                  30

Asn Val Asp Ser Ala Xaa Xaa Xaa Xaa Xaa Xaa Xaa Xaa Xaa Xaa Xaa
        35                  40                  45

Xaa Xaa Xaa Xaa Xaa Xaa Ser Ala Ser Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Gln Gln Tyr
                85                  90                  95

Tyr Ser Thr Pro Trp Thr Xaa Xaa Xaa Xaa Xaa Xaa Xaa Xaa
                100                 105                 110
```

<210> SEQ ID NO 75
<211> LENGTH: 470
<212> TYPE: PRT
<213> ORGANISM: Artificial sequence
<220> FEATURE:

<223> OTHER INFORMATION: Klo43-1+SP

<400> SEQUENCE: 75

```
Met Ala Leu Pro Val Thr Ala Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
        115                 120                 125

Tyr Ser Pro Glu Gly Ala Met Asp Tyr Trp Gly Gln Gly Thr Ser Val
    130                 135                 140

Thr Val Ser Ser Gly Gly Gly Ser Gly Gly Gly Ser Gly Gly Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
            180                 185                 190

Ala Ser Gln Asn Val Asp Ser Ala Val Ala Trp Tyr Gln Gln Lys Pro
        195                 200                 205

Gly Gln Ser Pro Lys Ala Leu Ile Tyr Ser Ala Ser Tyr Arg Tyr Ser
    210                 215                 220

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
                245                 250                 255

Gln Gln Tyr Tyr Ser Thr Pro Trp Thr Phe Gly Gly Gly Thr Lys Leu
            260                 265                 270

Glu Ile Lys Arg Gly Leu Ala Val Ser Thr Ile Ser Ser Phe Phe Pro
        275                 280                 285

Pro Gly Tyr Gln Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400
```

```
Pro Glu Met Gly Gly Lys Pro Arg Arg Lys Asn Pro Gln Glu Gly Leu
            405                 410                 415

Tyr Asn Glu Leu Gln Lys Asp Lys Met Ala Glu Ala Tyr Ser Glu Ile
        420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 76
<211> LENGTH: 499
<212> TYPE: PRT
<213> ORGANISM: Artificial sequence
<220> FEATURE:
<223> OTHER INFORMATION: Klo43-3+SP

<400> SEQUENCE: 76

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
        115                 120                 125

Tyr Ser Pro Glu Gly Ala Met Asp Tyr Trp Gly Gln Gly Thr Ser Val
    130                 135                 140

Thr Val Ser Ser Gly Gly Gly Gly Ser Gly Gly Gly Gly Ser Gly Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
            180                 185                 190

Ala Ser Gln Asn Val Asp Ser Ala Val Ala Trp Tyr Gln Gln Lys Pro
        195                 200                 205

Gly Gln Ser Pro Lys Ala Leu Ile Tyr Ser Ala Ser Tyr Arg Tyr Ser
    210                 215                 220

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
                245                 250                 255

Gln Gln Tyr Tyr Ser Thr Pro Trp Thr Phe Gly Gly Gly Thr Lys Leu
            260                 265                 270

Glu Ile Lys Arg Thr Thr Thr Pro Ala Pro Arg Pro Pro Thr Pro Ala
        275                 280                 285
```

```
Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
                340                 345                 350

Leu Tyr Ile Phe Lys Gln Pro Phe Met Arg Pro Val Gln Thr Thr Gln
                355                 360                 365

Glu Glu Asp Gly Cys Ser Cys Arg Phe Pro Glu Glu Glu Glu Gly Gly
370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
                420                 425                 430

Gly Gly Lys Pro Arg Arg Lys Asn Pro Gln Glu Gly Leu Tyr Asn Glu
                435                 440                 445

Leu Gln Lys Asp Lys Met Ala Glu Ala Tyr Ser Glu Ile Gly Met Lys
450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 77
<211> LENGTH: 685
<212> TYPE: PRT
<213> ORGANISM: Artificial sequence
<220> FEATURE:
<223> OTHER INFORMATION: Klo43-5+SP

<400> SEQUENCE: 77

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
                20                  25                  30

Val Gln Pro Gly Gly Ser Leu Ser Leu Ser Cys Ala Ala Ser Gly Phe
            35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
                100                 105                 110

Asp Ser Ala Thr Tyr Tyr Cys Ala Arg Asp Ala Ala Tyr Tyr Ser Tyr
            115                 120                 125

Tyr Ser Pro Glu Gly Ala Met Asp Tyr Trp Gly Gln Gly Thr Ser Val
    130                 135                 140

Thr Val Ser Ser Gly Gly Gly Gly Ser Gly Gly Gly Gly Ser Gly Gly
```

```
            145                 150                 155                 160
Gly Gly Ser Met Ala Asp Tyr Lys Asp Ile Val Met Thr Gln Ser His
                165                 170                 175
Lys Phe Met Ser Thr Ser Val Gly Asp Arg Val Asn Ile Thr Cys Lys
                180                 185                 190
Ala Ser Gln Asn Val Asp Ser Ala Val Ala Trp Tyr Gln Gln Lys Pro
                195                 200                 205
Gly Gln Ser Pro Lys Ala Leu Ile Tyr Ser Ala Ser Tyr Arg Tyr Ser
    210                 215                 220
Gly Val Pro Asp Arg Phe Thr Gly Arg Gly Ser Gly Thr Asp Phe Thr
225                 230                 235                 240
Leu Thr Ile Ser Ser Val Gln Ala Glu Asp Leu Ala Val Tyr Tyr Cys
                245                 250                 255
Gln Gln Tyr Tyr Ser Thr Pro Trp Thr Phe Gly Gly Gly Thr Lys Leu
                260                 265                 270
Glu Ile Lys Arg Glu Pro Lys Ser Pro Asp Lys Thr His Thr Cys Pro
                275                 280                 285
Pro Cys Pro Ala Pro Pro Val Ala Gly Pro Ser Val Phe Leu Phe Pro
    290                 295                 300
Pro Lys Pro Lys Asp Thr Leu Met Ile Ala Arg Thr Pro Glu Val Thr
305                 310                 315                 320
Cys Val Val Val Asp Val Ser His Glu Asp Pro Glu Val Lys Phe Asn
                325                 330                 335
Trp Tyr Val Asp Gly Val Glu Val His Asn Ala Lys Thr Lys Pro Arg
                340                 345                 350
Glu Glu Gln Tyr Asn Ser Thr Tyr Arg Val Val Ser Val Leu Thr Val
                355                 360                 365
Leu His Gln Asp Trp Leu Asn Gly Lys Glu Tyr Lys Cys Lys Val Ser
    370                 375                 380
Asn Lys Ala Leu Pro Ala Pro Ile Glu Lys Thr Ile Ser Lys Ala Lys
385                 390                 395                 400
Gly Gln Pro Arg Glu Pro Gln Val Tyr Thr Leu Pro Pro Ser Arg Asp
                405                 410                 415
Glu Leu Thr Lys Asn Gln Val Ser Leu Thr Cys Leu Val Lys Gly Phe
                420                 425                 430
Tyr Pro Ser Asp Ile Ala Val Glu Trp Glu Ser Asn Gly Gln Pro Glu
                435                 440                 445
Asn Asn Tyr Lys Thr Thr Pro Pro Val Leu Asp Ser Asp Gly Ser Phe
    450                 455                 460
Phe Leu Tyr Ser Lys Leu Thr Val Asp Lys Ser Arg Trp Gln Gln Gly
465                 470                 475                 480
Asn Val Phe Ser Cys Ser Val Met His Glu Ala Leu His Asn His Tyr
                485                 490                 495
Thr Gln Lys Ser Leu Ser Leu Ser Pro Gly Lys Ile Tyr Ile Trp Ala
                500                 505                 510
Pro Leu Ala Gly Thr Cys Gly Val Leu Leu Leu Ser Leu Val Ile Thr
                515                 520                 525
Leu Tyr Cys Lys Arg Gly Arg Lys Lys Leu Leu Tyr Ile Phe Lys Gln
    530                 535                 540
Pro Phe Met Arg Pro Val Gln Thr Thr Gln Glu Glu Asp Gly Cys Ser
545                 550                 555                 560
Cys Arg Phe Pro Glu Glu Glu Glu Gly Gly Cys Glu Leu Arg Val Lys
                565                 570                 575
```

-continued

```
Phe Ser Arg Ser Ala Asp Ala Pro Ala Tyr Gln Gln Gly Gln Asn Gln
            580                 585                 590

Leu Tyr Asn Glu Leu Asn Leu Gly Arg Arg Glu Glu Tyr Asp Val Leu
        595                 600                 605

Asp Lys Arg Arg Gly Arg Asp Pro Glu Met Gly Gly Lys Pro Arg Arg
610                         615                 620

Lys Asn Pro Gln Glu Gly Leu Tyr Asn Glu Leu Gln Lys Asp Lys Met
625                 630                 635                 640

Ala Glu Ala Tyr Ser Glu Ile Gly Met Lys Gly Glu Arg Arg Arg Gly
                645                 650                 655

Lys Gly His Asp Gly Leu Tyr Gln Gly Leu Ser Thr Ala Thr Lys Asp
            660                 665                 670

Thr Tyr Asp Ala Leu His Met Gln Ala Leu Pro Pro Arg
        675                 680                 685
```

CD123 SPECIFIC CHIMERIC ANTIGEN RECEPTORS FOR CANCER IMMUNOTHERAPY

CROSS REFERENCE TO RELATED APPLICATIONS

This application is a continuation of U.S. Application Ser. No. 15/925,182. filed Mar. 19, 2018, which received a Notice of Allowance on Dec. 30, 2020, which is continuation of U.S. Application Ser. No. 15/126,540. filed Sep. 15, 2016. now U.S. Pat. No. 9,944,709. issued Apr. 17, 2018, which is a national phase application under 35 U.S.C. § 371 of PCT International Application No. PCT/EP2015/055848, filed Mar. 19, 2015, which claims priority to Danish Application No. PA201470137, filed Mar. 19, 2014, each of which are hereby incorporated by reference in its entirety.

SEQUENCE LISTING STATEMENT

The contents of the electronic sequence listing titled (2020-12-17_36656-303_SQL_ST25.txt; Size: 233,906 bytes; and Date of Creation: Dec. 17, 2020) is herein incorporated by reference in its entirety.

FIELD OF THE INVENTION

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a CD123 monoclonal antibody, conferring specific immunity against CD123 positive cells. Interleukin 3 receptor alpha chain (CD123) has been identified as being frequently over-expressed on Leukemia tumor cells, especially in the case of acute myeloid leukemia (AML), compared to normal hematopoietic stem cells. The engineered immune cells endowed with the CARs according to the invention show higher efficiency in view of treating lymphomas and leukemia.

Background of the Invention

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-188 (CD137) have been added alone (second generation) or in combination (third generation) to enhance survival and Increase proliferation of CAR modified T cells. CARs have successfully allowed T cells to be redirected against antigens expressed at the surface of tumor cells from various malignancies including lymphomas and solid tumors (Jena, Dotti et al. 2010).

Meanwhile, induction treatments for acute myeloid leukemia (AML) have remained largely unchanged for nearly 50 years and AML remains a disease of poor prognosis. Acute myeloid leukemia (AML) is a disease characterized by the rapid proliferation of immature myeloid cells in the bone marrow resulting in dysfunctional hematopoiesis. Although standard induction chemotherapy can induce complete remissions, many patients eventually relapse and succumb to the disease, calling for the development of novel therapeutics for AML.

Recent advances in the immunophenotyping of AML cells have revealed several AML associated cell surface antigens that may act as targets for future therapies. The interleukin 3 receptor alpha chain (IL-3R$\alpha$; CD123—NCBI reference: NP_001254642) has been identified as a potential immunotherapeutic target since it is over-expressed on AML tumor cells compared to normal hematopoietic stem cells. Additionally, two phase I trials for CD123-specific therapeutics have been completed with both drugs displaying good safety profiles (ClinicalTrials.gov ID: NCT00401739 and NCT00397579). Unfortunately, these CD123 targeting drugs had limited efficacy suggesting that alternative, and more potent and specific therapies targeting CD123 are required to observe anti-leukemic activity. A possibly more potent alternative therapy for the treatment of Leukemia could be the use of T cells expressing chimeric antigen receptors (CARs) that redirect T cell specificity towards cell surface tumor associated antigens (TAAs) in an MHC-independent manner.

Several groups have developed CARs targeting various antigens for the treatment of 8-cell malignancies. However, CAR engineered T cells for the treatment of AML remain scarce.

In particular, there is still a need to improve construction of CARs that show better compatibility with T-cell proliferation, in order to allow the cells expressing such CARs to reach significant clinical advantage.

In addition, there is a need to improve CD123 CARs having the capacity to proliferate and target selectively CD123 expressing cells.

Further, the use of such CAR expressing immune T cell targeting CD123 in combination with cytotoxic chemotherapy agents as a treatment usually employed as anticancer treatments remains a problem.

Several cytotoxic agents such as anti-metabolites, alkylating agents, anthracyclines, DNA methyltransferase Inhibitors, platinum compounds and spindle poisons have been developed to kill cancer cells, in particular cancer cells expressing CD123.

These chemotherapy agents can be detrimental to the establishment of robust anti-tumor immunocompetent cells due to their non-specific toxicity. Small molecule-based therapies targeting cell proliferation pathways may also hamper the establishment of anti-tumor immunity.

Thus, there is also a need of developing T cells targeting CD123 that would be specific and compatible with the use of drugs, in particular of anti-cancer chemotherapies, such as those affecting cell proliferation.

Thus, to use "off-the-shelf" allogeneic therapeutic cells in conjunction with chemotherapy, the inventors develop a method of engineering allogeneic T-cell, less allogenic and resistant to chemotherapeutic agents. The therapeutic benefits afforded by this strategy should be enhanced by the synergistic effects between chemotherapy and immunotherapy. Moreover, drug resistance can also benefit from the ability to selectively expand the engineered T-cell thereby avoiding the problems due to inefficient gene transfer to these cells.

SUMMARY OF THE INVENTION

The inventors have generated CD123 specific CAR having different design and comprising different scFV derived from CD123 specific antibodies. These CD123 specific CAR are designated CD123 specific CAR or anti-CD123 CAR, or 123 CAR, or "CAR of the invention" indiscriminately.

In particular, The Inventors have developed CD123 specific CAR comprising a scFV derived from Klon43 with different architectures and identified highly specific and very selective CARs constructions that bind to CD123 expressing cells and selectively destroy CD123 expressing cancer cells.

Following non-specific activation in vitro (e.g. with anti CD3/CD28 coated beads and recombinant IL2), T-cells from donors have been transformed with polynucleotides expressing these CARs using viral transduction. In certain instances, the T-cells were further engineered to create non-alloreactive T-cells, more especially by disruption of a component of TCR ($\alpha\beta$-T-Cell receptors) to prevent Graft versus host reaction.

T-cells were further engineered to create T cells resistant to anti-cancer drugs, to be used in combination with said classical anti-cancer drugs.

The resulting engineered T-cells displayed reactivity in-vitro against CD123 positive cells to various extend, showing that the CARs of the present invention contribute to antigen dependent activation, and also proliferation, of the T-cells, making them useful for immunotherapy.

The resulting engineered T-cells displayed reactivity in-vivo against CD123 positive cells and significantly reduce the number of cancer cells in vivo.

The engineered T-cells of the invention are designed to display in-vivo reactivity against CD123 positive cells, can be used in concomitance with anti-cancer drugs, are well tolerated. In a particular embodiment, the engineered T-cells of the invention remain efficient even after several administrations, making them useful for immunotherapy as a first treatment (induction), as a consolidation treatment, as a treatment in combination with classical anticancer chemotherapy. The polypeptides and polynucleotide sequences encoding the CARs of the present invention are detailed in the present specification.

The engineered immune cells of the present invention are particularly useful for therapeutic applications such as B-cell lymphoma or leukemia treatments.

TABLE 1

Sequence of the different CAR components

Figure 1:
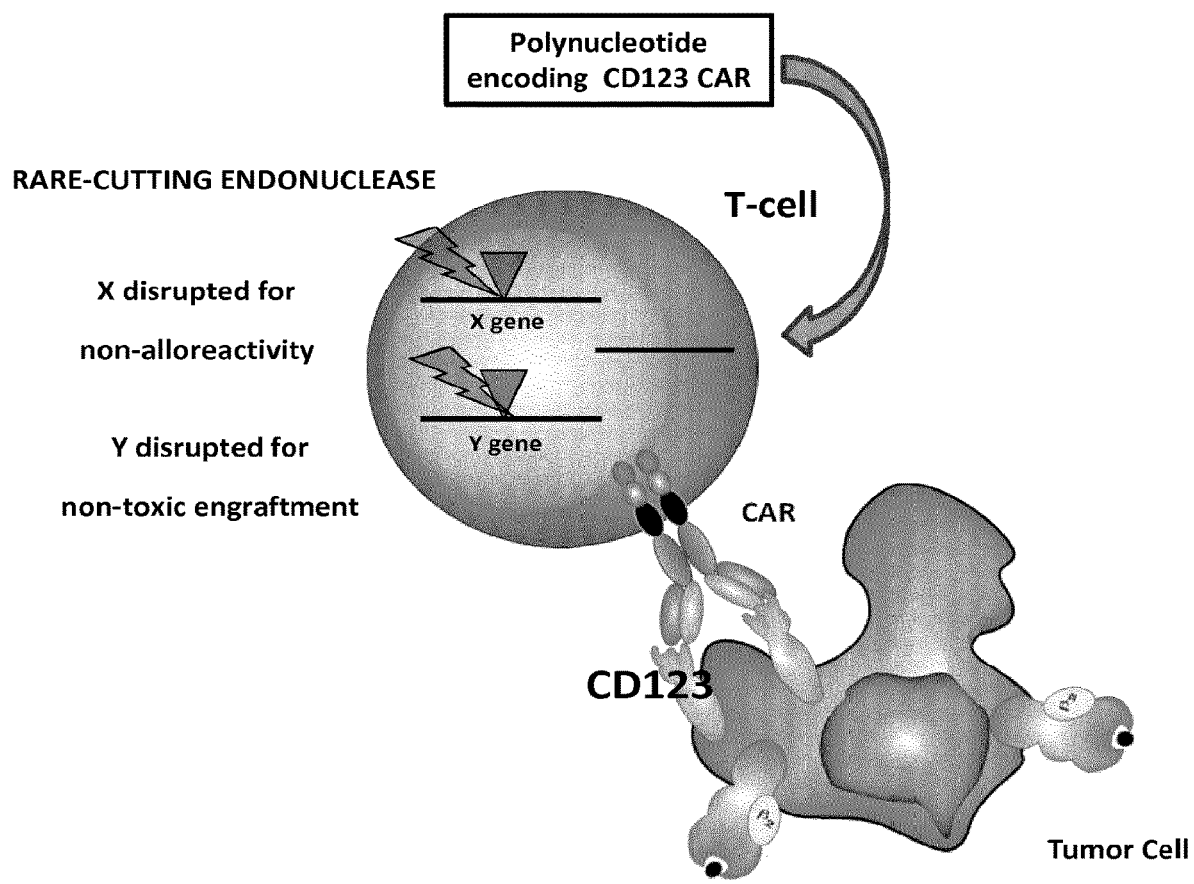
FIG. 1: Schematic representation of an engineered immune cell according to the invention. The engineered immune cell presented in this figure is a T-cell transduced with a retroviral polypeptide encoding CAR. This T-Cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or HPRT (with respect to 6-Thioguanine)

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| FcγRIIIα hinge | SEQ ID NO. 3 | GLAVSTISSFFPPGYQ |
| CD8α hinge | SEQ ID NO. 4 | TTTPAPRPPTPAPTIASQPLSLRPEACRPAAG GAVHTRGLDFACD |
| IgG1 hinge | SEQ ID NO. 5 | EPKSPDKTHTCPPCPAPPVAGPSVFLFPPKP KDTLMIARTPEVTCVVVDVSHEDPEVKFNW YVDGVEVHNAKTKPREEQYNSTYRVVSVLT VLHQDWLNGKEYKCKVSNKALPAPIEKTISK AKGQPREPQVYTLPPSRDELTKNQVSLTCLV KGFYPSDIAVEWESNGQPENNYKTTPPVLD SDGSFFLYSKLTVDKSRWQQGNVFSCSVM HEALHNHYTQKSLSLSPGK |
| CD8α transmembrane domain | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |
| 41BB intracellular domain | SEQ ID NO. 8 | KRGRKKLLYIFKQPFMRPVQTTQEEDGCSC RFPEEEEGGCEL |
| CD3ζ intracellular domain | SEQ ID NO. 9 | RVKFSRSADAPAYQQGQNQLYNELNLGRR EEYDVLDKRRGRDPEMGGKPRRKNPQEGL YNELQKDKMAEAYSEIGMKGERRRGKGHD GLYQGLSTATKDTYDALHMQALPPR |
| Linker | SEQ ID NO. 10 | GGGGSGGGGSGGGGS |

TABLE 2

Sequence of the different CAR components

| ScFv sequences | SEQ ID # | Raw amino acid sequence |
|---|---|---|
| 7G3 heavy chain variable region | SEQ ID NO. 11 | MGWSWIFLFLVSGTGGVLSEVQLQQSGPELVKPGASV KMSCKASGYTFTDYYMKWVKQSHGKSLEWIGDIIPSNG ATFYNQKFKGKATLTVDRSSSTAYMHLNSLTSEDSAVYY CTRSHLLRASWFAYWGQGTLVTVSAAS |
| 7G3 light chain variable region | SEQ ID NO. 12 | MESQTQVLMSLLFWVSGTCGDFVMTQSPSSLTVTAGE KVTMSCKSSQSLLNSGNQKNYLTWYLQKPGQPPKLLIY WASTRESGVPDRFTGSGSGTDFTLTISSVQAEDLAVYYC QNDYSYPYTFGGGTKLEIKR |
| Old4 heavy chain variable region | SEQ ID NO. 13 | WTWRFLFVVAAATGVQSQVQLLQSGAEVKKPGSSVKV SCKASGGTFSTYAISWVRQAPGQGLEWMGGIIPIFGIV NYAQKFQGRVTITADESTSTAYMELSSLRSEDTAVYYCA RGGGSGPDVLDIWGQGTMVTVSSAST |
| Old4 light chain variable region | SEQ ID NO. 14 | MDMRVPAQLLGLLLLWLPGARCVIWMTQSPSLLSAST GDRVTISCRMSQGIRSYLAWYQQKPGKAPELLIYAASTL QSGVPSRFSGSGSGTDFTLTISSLQSEDFATYYCQQYYSF PYTFGQGTKLEIKRTV |
| 26292 heavy chain variable region | SEQ ID NO. 15 | QVQLQQPGAELVRPGASVKLSCKASGYTFTSYWMNW VKQRPDQGLEWIGRIDPYDSETHYNQKFKDKAILTVDKS SSTAYMQLSSLTSEDSAVYYCARGNWDDYWGQGTTLT VSS |

TABLE 2-continued

Sequence of the different CAR components

| ScFv sequences | SEQ ID # | Raw amino acid sequence |
| --- | --- | --- |
| 26292 light chain variable region | SEQ ID NO. 16 | DVQITQSPSYLAASPGETITINCRASKSISKDLAWYQEKP GKTNKLLIYSGSTLQSGIPSRFSGSGSGTDFTLTISSLEPED FAMYYCQQHNKYPYTFGGGTKLEIK |
| 32716 heavy chain variable region | SEQ ID NO. 17 | QIQLVQSGPELKKPGETVKISCKASGYIFTNYGMNWVK QAPGKSFKWMGWINTYTGESTYSADFKGRFAFSLETSA STAYLHINDLKNEDTATYFCARSGGYDPMDYWGQGTS VTVSS |
| 32716 light chain variable region | SEQ ID NO. 18 | DIVLTQSPASLAVSLGQRATISCRASESVDNYGNTFMH WYQQKPGQPPKLLIYRASNLESGIPARFSGSGSRTDFTLT INPVEADDVATYYCQQSNEDPPTFGAGTKLELK |
| Klon43 heavy chain variable region | SEQ ID NO. 19 | MADYKDIVMTQSHKFMSTSVGDRVNITCKASQNVDSA VAWYQQKPGQSPKALIYSASYRYSGVPDRFTGRGSGTD FTLTISSVQAEDLAVYYCQYYSTPWTFGGGTKLEIKR |
| Klon43 light chain variable region | SEQ ID NO. 20 | EVKLVESGGGLVQPGGSLSLSCAASGFTFTDYYMSWVR QPPGKALEWLALIRSKADGYTTEYSASVKGRFTLSRDDS QSILYLQMNALRPEDSATYYCARDAAYYSYYSPEGAMD YWGQGTSVTVSS |
| 12F1 heavy chain variable region | SEQ ID NO. 21 | VQLQESGPGLVKPSQSLSLTCSVTDYSITSGYYWNWIRQ FPGNKLEWMGYISYDGSNNYNPSLKNRISITRDTSKNQF FLKLSSVTTEDTATYYCSRGEGFYFDSWGQGTTLTVSSA RS |
| 12F1 light chain variable region | SEQ ID NO. 22 | DIMMSQSPSSLAVSVGEKFTMTCKSSQSLFFGSTQKNYL AWYQQKPGQSPKLLIYWASTRESGVPDRFTGSGSGTDF TLAISSVMPEDLAVYYCQQYYNYPWTFGGGTKLEIK |

TABLE 3

CAR of structure V-1

CAR Structure

| CAR Designation V-1 | signal peptide (optional) | VH | VL | FcγRIIIα hinge | CD8α TM | 41BB-IC | CD3ζ CD |
| --- | --- | --- | --- | --- | --- | --- | --- |
| 7G3-1 (SEQ ID NO. 23) | SEQ ID NO. 1 | SEQ ID NO. 11 | SEQ ID NO. 12 | SEQ ID NO. 3 | SEQ ID NO. 6 | SEQ ID NO. 8 | SEQ ID NO. 9 |
| 26292-1 (SEQ ID NO. 30) | SEQ ID NO. 1 | SEQ ID NO. 15 | SEQ ID NO. 16 | SEQ ID NO. 3 | SEQ ID NO. 6 | SEQ ID NO. 8 | SEQ ID NO. 9 |
| 32716-1 (SEQ ID NO. 36) | SEQ ID NO. 1 | SEQ ID NO. 17 | SEQ ID NO. 18 | SEQ ID NO. 3 | SEQ ID NO. 6 | SEQ ID NO. 8 | SEQ ID NO. 9 |
| Klo43-1 SEQ ID NO. 42) | SEQ ID NO. 1 | SEQ ID NO. 19 | SEQ ID NO. 20 | SEQ ID NO. 3 | SEQ ID NO. 6 | SEQ ID NO. 8 | SEQ ID NO. 9 |

TABLE 4

CAR of structure V-2

CAR Structure

| CAR Designation V-2 | signal peptide (optional) | VH | VL | FcγRIIIα hinge | 41BB-TM | 41BB-IC | CD3ζ CD |
| --- | --- | --- | --- | --- | --- | --- | --- |
| 7G3-2 (SEQ ID NO. 24) | SEQ ID NO. 1 | SEQ ID NO. 11 | SEQ ID NO. 12 | SEQ ID NO. 3 | SEQ ID NO. 7 | SEQ ID NO. 8 | SEQ ID NO. 9 |
| 26292-2 (SEQ ID NO. 31) | SEQ ID NO. 1 | SEQ ID NO. 15 | SEQ ID NO. 16 | SEQ ID NO. 3 | SEQ ID NO. 7 | SEQ ID NO. 8 | SEQ ID NO. 9 |

TABLE 4-continued

CAR of structure V-2

| CAR Designation V-2 | signal peptide (optional) | VH | VL | FcγRIIIα hinge | 41BB-TM | 41BB-IC | CD3ζ CD |
|---|---|---|---|---|---|---|---|
| 32716-2 (SEQ ID NO. 37) | SEQ ID NO. 1 | SEQ ID NO. 17 | SEQ ID NO. 18 | SEQ ID NO. 3 | SEQ ID NO. 7 | SEQ ID NO. 8 | SEQ ID NO. 9 |
| Klo43-2 (SEQ ID NO. 43) | SEQ ID NO. 1 | SEQ ID NO. 19 | SEQ ID NO. 20 | SEQ ID NO. 3 | SEQ ID NO. 7 | SEQ ID NO. 8 | SEQ ID NO. 9 |

TABLE 5

CAR of structure V-3

| CAR Designation V-3 | signal peptide (optional) | VH | VL | CD8α hinge | CD8α TM | 41BB-IC | CD3ζ CD |
|---|---|---|---|---|---|---|---|
| 7G3-3 (SEQ ID NO. 25) | SEQ ID NO. 1 | SEQ ID NO. 11 | SEQ ID NO. 12 | SEQ ID NO. 4 | SEQ ID NO. 6 | SEQ ID NO. 8 | SEQ ID NO. 9 |
| Old4-3 (SEQ ID NO. 29) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| 26292-3 (SEQ ID NO. 32) | SEQ ID NO. 1 | SEQ ID NO. 15 | SEQ ID NO. 16 | SEQ ID NO. 4 | SEQ ID NO. 6 | SEQ ID NO. 8 | SEQ ID NO. 9 |
| 32716-3 (SEQ ID NO. 38) | SEQ ID NO. 1 | SEQ ID NO. 17 | SEQ ID NO. 18 | SEQ ID NO. 4 | SEQ ID NO. 6 | SEQ ID NO. 8 | SEQ ID NO. 9 |
| Klo43-3 (SEQ ID NO. 44) | SEQ ID NO. 1 | SEQ ID NO. 20 | SEQ ID NO. 19 | SEQ ID NO. 4 | SEQ ID NO. 6 | SEQ ID NO. 8 | SEQ ID NO. 9 |
| 12SF1-3 (SEQ ID NO. 48) | SEQ ID NO. 1 | SEQ ID NO. 21 | SEQ ID NO. 22 | SEQ ID NO. 4 | SEQ ID NO. 6 | SEQ ID NO. 8 | SEQ ID NO. 9 |

TABLE 6

CAR of structure V-4

| CAR Designation V-4 | signal peptide (optional) | VH | VL | CD8α hinge | 41BB-TM | 41BB-IC | CD3ζ CD |
|---|---|---|---|---|---|---|---|
| 7G3-4 (SEQ ID NO. 26) | SEQ ID NO. 1 | SEQ ID NO. 11 | SEQ ID NO. 12 | SEQ ID NO. 4 | SEQ ID NO. 7 | SEQ ID NO. 8 | SEQ ID NO. 9 |
| 26292-4 (SEQ ID NO. 33) | SEQ ID NO. 1 | SEQ ID NO. 15 | SEQ ID NO. 16 | SEQ ID NO. 4 | SEQ ID NO. 7 | SEQ ID NO. 8 | SEQ ID NO. 9 |
| 32716-4 (SEQ ID NO. 39) | SEQ ID NO. 1 | SEQ ID NO. 17 | SEQ ID NO. 18 | SEQ ID NO. 4 | SEQ ID NO. 7 | SEQ ID NO. 8 | SEQ ID NO. 9 |
| Klo43-4 (SEQ ID NO. 45) | SEQ ID NO. 1 | SEQ ID NO. 19 | SEQ ID NO. 20 | SEQ ID NO. 4 | SEQ ID NO. 7 | SEQ ID NO. 8 | SEQ ID NO. 9 |

TABLE 7

CAR of structure V-5

| CAR Designation V-5 | signal peptide (optional) | VH | VL | IgG1 hinge | CD8α TM | 41BB-IC | CD3ζ CD |
|---|---|---|---|---|---|---|---|
| 7G3-5 (SEQ ID NO. 27) | SEQ ID NO. 1 | SEQ ID NO. 11 | SEQ ID NO. 12 | SEQ ID NO. 5 | SEQ ID NO. 6 | SEQ ID NO. 8 | SEQ ID NO. 9 |
| 26292-5 (SEQ ID NO. 34) | SEQ ID NO. 1 | SEQ ID NO. 15 | SEQ ID NO. 16 | SEQ ID NO. 5 | SEQ ID NO. 6 | SEQ ID NO. 8 | SEQ ID NO. 9 |
| 32716-5 (SEQ ID NO. 40) | SEQ ID NO. 1 | SEQ ID NO. 17 | SEQ ID NO. 18 | SEQ ID NO. 5 | SEQ ID NO. 6 | SEQ ID NO. 8 | SEQ ID NO. 9 |
| Klo43-5 (SEQ ID NO. 46) | SEQ ID NO. 1 | SEQ ID NO. 20 | SEQ ID NO. 19 | SEQ ID NO. 5 | SEQ ID NO. 6 | SEQ ID NO. 8 | SEQ ID NO. 9 |

TABLE 8

CAR of structure V-6

| CAR Designation V-6 | signal peptide (optional) | VH | VL | IgG1 hinge | 41BB-TM | 41BB-IC | CD3ζ CD |
|---|---|---|---|---|---|---|---|
| 7G3-6 (SEQ ID NO. 28) | SEQ ID NO. 1 | SEQ ID NO. 11 | SEQ ID NO. 12 | SEQ ID NO. 5 | SEQ ID NO. 7 | SEQ ID NO. 8 | SEQ ID NO. 9 |
| 26292-6 (SEQ ID NO. 35) | SEQ ID NO. 1 | SEQ ID NO. 15 | SEQ ID NO. 16 | SEQ ID NO. 5 | SEQ ID NO. 7 | SEQ ID NO. 8 | SEQ ID NO. 9 |
| 32716-6 (SEQ ID NO. 41) | SEQ ID NO. 1 | SEQ ID NO. 17 | SEQ ID NO. 18 | SEQ ID NO. 5 | SEQ ID NO. 7 | SEQ ID NO. 8 | SEQ ID NO. 9 |
| Klo43-6 (SEQ ID NO. 47) | SEQ ID NO. 1 | SEQ ID NO. 20 | NO.19 | SEQ ID NO. 5 | SEQ ID NO. 7 | SEQ ID NO. 8 | SEQ ID NO. 9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are Incorporated by reference in their entirety, In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. i. Gait ed., 1984); Mullis et al. U.S. Pat. No. 4,683,195; Nucleic Acid Hybridization (8. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Figure 2:
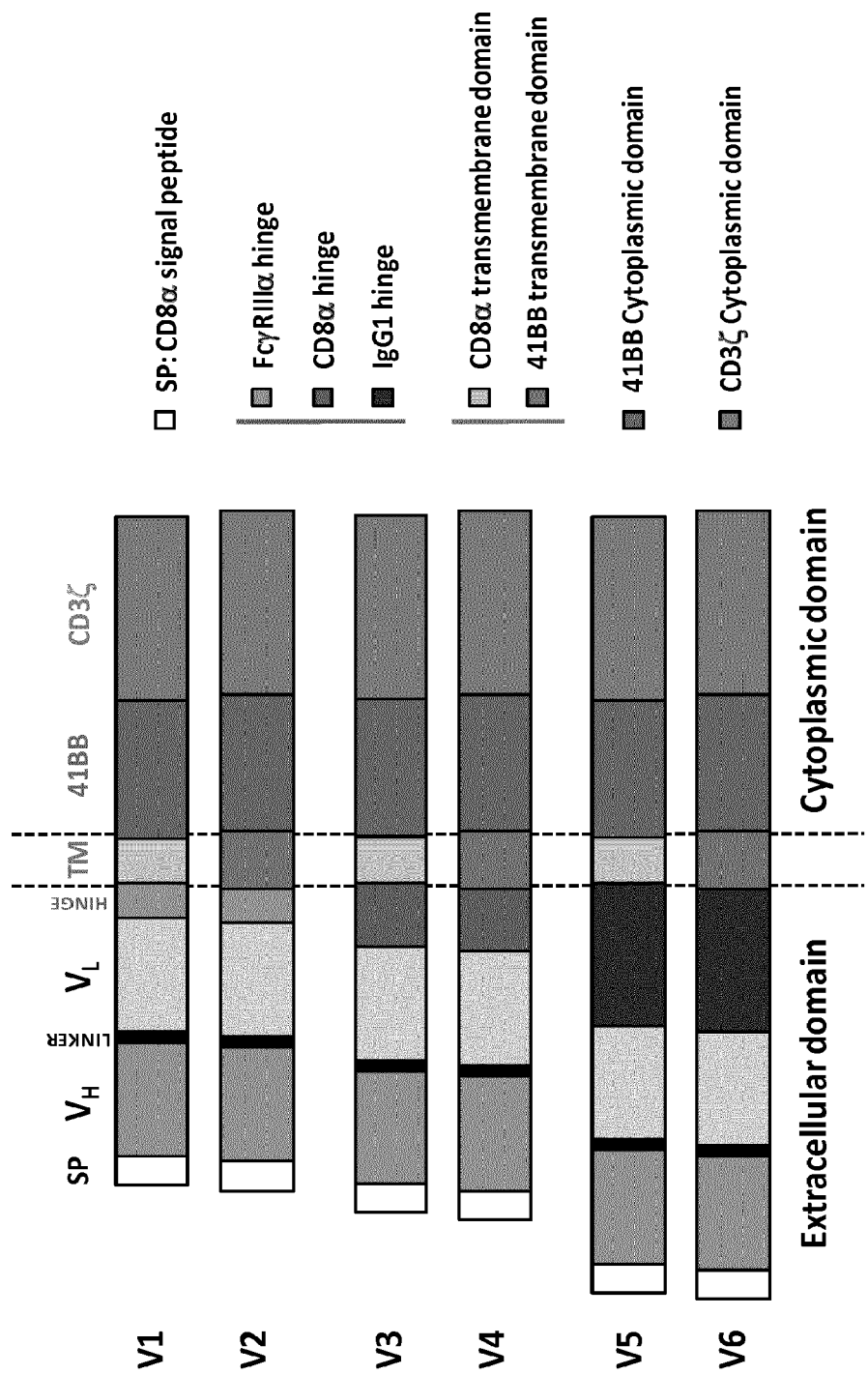
FIG. 2: Schematic representation of the different CAR Architecture (V1 to V6) of the invention (123 CAR)

The present invention discloses a CD123 specific chimeric antigen receptor ("123 CAR" or "CAR") having one of the polypeptide structure selected from V1 to V6, as illustrated in FIG. 2, said structure comprising an extra cellular ligand binding-domain comprising VH and VL from a monoclonal anti-CD123 antibody, a hinge, a transmembrane domain, a cytoplasmic domain including a CD3 zeta signaling domain and a co-stimulatory domain from 4-1BB, said 123 CAR having at least 80% sequence identity with either SEQ ID NO. 42, SEQ ID NO. 44, SEQ ID NO. 46, SEQ ID NO. 29 or SEQ ID NO. 48.

The present invention discloses a CD123 specific chimeric antigen receptor (123 CAR) having one of the polypeptide structure selected from V1, V3 and V5, as illustrated in FIG. 2, said structure comprising an extra cellular ligand binding-domain comprising VH and VL from a monoclonal anti-CD123 antibody, a hinge, a transmembrane domain, a cytoplasmic domain including a CD3 zeta signaling domain and a co-stimulatory domain from 4-1BB, said 123 CAR having at least 80% sequence identity with either SEQ ID NO. 42, SEQ ID NO. 44 or SEQ ID NO. 46.

The present invention discloses a CD123 specific chimeric antigen receptor (123 CAR) having one of the polypeptide structure selected from V1, V3 and VS, as illustrated in FIG. 2, said structure comprising an extra cellular ligand binding-domain comprising VH and VL from a monoclonal anti-CD123 antibody, a hinge, a transmembrane domain, a cytoplasmic domain including a CD3 zeta signaling domain and a co-stimulatory domain from 4-1BB, said 123 CAR having at least 80% sequence identity with either SEQ ID NO. 75, SEQ ID NO. 76, SEQ ID NO. 77.

The present invention discloses a specific chimeric antigen receptor (123 CAR) having a polypeptide structure V3 as illustrated in FIG. 2, and described above wherein said 123 CAR has at least 80% sequence identity with SEQ ID NO. 42.

The present invention discloses a specific chimeric antigen receptor (123 CAR) having a polypeptide structure V3 as illustrated in FIG. 2, and described above, wherein said 123 CAR has at least 80% sequence identity with SEQ ID NO, 44.

The present invention discloses a specific chimeric antigen receptor (123 CAR) having a polypeptide structure V3 as illustrated in FIG. 2, and described above wherein said 123 CAR has at least 80% sequence identity with SEQ ID NO. 46.

The present invention discloses a specific chimeric antigen receptor (123 CAR) having a polypeptide structure V3 as illustrated in FIG. 2, and described above wherein said 123 CAR has at least 80% sequence identity with SEQ ID NO., 75.

The present invention discloses a specific chimeric antigen receptor (123 CAR) having a polypeptide structure V3 as illustrated in FIG. 2, and described above wherein said 123 CAR has at least 80% sequence identity with SEQ ID NO. 76.

The present invention discloses a specific chimeric antigen receptor (123 CAR) having a polypeptide structure V3 as illustrated in FIG. 2, and described above wherein said 123 CAR has at least 80% sequence identity with SEQ ID NO. 77.

The present invention discloses a CD123 specific chimeric antigen receptor (CAR) having a polypeptide structure V3 as illustrated in FIG. 2, and described above said structure comprising an extra cellular ligand binding-domain VH and VL from a monoclonal anti-CD123 antibody comprising the following CDR sequences:

```
                                    (SEQ ID NO 67)
GFTFTDYY, (SEQ ID NO 68)
RSKADGYTT, (SEQ ID NO 69)
ARDAAYYSYYSPEGAMDY,
and (SEQ ID NO 70)
QNVDSA, (SEQ ID NO 71)
SAS, (SEQ ID NO 72)
QQYYSTPWT,
``` and said structure comprising:
a hinge, a transmembrane domain and a cytoplasmic domain including a CD3 zeta signaling domain and a co-stimulatory domain from 4-1BB.

The present invention discloses a CD123 specific chimeric antigen receptor (123 CAR) as above, wherein said extra cellular ligand binding-domain VH and VL is humanized.

The present invention discloses a CD123 specific chimeric antigen receptor (123 CAR) as above, wherein said extra cellular ligand binding-domain is humanized.

The present invention discloses a CD123 specific chimeric antigen receptor (123 CAR) as above, said CD123 specific chimeric antigen receptor is humanized.

The present invention discloses a CD123 specific chimeric antigen receptor (123 CAR) as above, wherein said extra cellular ligand binding-domain VH and VL from a monoclonal anti-CD123 antibody comprises the following sequence

```
                                    (SEQ ID NO 73)
XXXXXXXXXXXXXXXXXXXXXXXXXXXXXXGFTFTDYYXXXXXXXXXXXX

XXXXXIRSKADGYTTXXXXXXXXXXXXXXXXXXXXXXXXXXXARDAAYY

SYYSPEGAMDYXXXXXXXXXXX
and (SEQ ID NO 74)
XXXXXXXXXXXXXXXXXXXXXXXXXXXXXXXXQNVDSAXXXXXXXXXXXXX

XXXXSASXXXXXXXXXXXXXXXXXXXXXXXXXXXXXXXXXXXQQYYSTP

WTXXXXXXXXXX,
``` wherein X is an amino acid.
an amino acid can be anyone of the amino acid, for example alanine, asparagine, aspartic acid, cysteine, glutamine, glutamic acid, glycine histidine, isoleucine, leucine, lysine, methionine, phenylalanine, proline, serine, threonine, tryptophan, tyrosine, valine, aspartic acid, glutamic acid.

The present invention discloses a CD123 specific chimeric antigen receptor (CAR) as described above, wherein said extra cellular ligand binding-domain VH and VL from a monoclonal anti-CD123 antibody respectively comprise at least one of the following sequences:

```
(Variant VH1: SEQ ID NO. 60):
EVKLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS,
```

-continued (Variant VH2: SEQ ID NO. 61):
EVQLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS, (Variant VH3: SEQ ID NO. 62):
EVQLVESGGGLVQPGRSLRLSCTASGFTFTDYYMSWVRQAPGKGLEWVGL

IRSKADGYTTEYSASVKGRFTISRDDSKSIAYLQMNSLKTEDTAVYYCAR

DAAYYSYYSPEGAMDYWGQGTLVTVSS, (Variant VH4: SEQ ID NO. 63):
EVQLVESGGGLVQPGRSLRLSCTASGFTFTDYYMSWVRQAPGKGLEWVGF

IRSKADGYTTEYSASVKGRFTISRDDSKSIAYLQMNSLKTEDTAVYYCAR

DAAYYSYYSPEGAMDYWGQGTLVTVSS, (Variant VH5: SEQ ID NO. 64):
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCAR

DAAYYSYYSPEGAMDYWGQGTLVTVSS, (Variant VH6: SEQ ID NO. 65):
EVQLVESGGGLVQPGRSLRLSCTASGFTFTDYYMSWVRQAPGKGLEWVGL

IRSKADGYTTEYAASVKGRFTISRDDSKSIAYLQMNSLKTEDTAVYYCAR

DAAYYSYYSPEGAMDYWGQGTLVTVSS, (Variant VH7: SEQ ID NO. 66):
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCTR

DAAYYSYYSPEGAMDYWGQGTLVTVSS,

Variant VL1: SEQ ID NO. 54):
MADYKDIVMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR,

Variant VL2: SEQ ID NO. 55):
MADYKDIQMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR,

Variant VL3: SEQ ID NO. 56):
MADYKDIQMTQSPSSVSASVGDRVTITCRASQNVDSAVAWYQQKPGKAPK

ALIYSASYRYSGVPSRFSGSGSGTDFTLTISSLQPEDFATYYCQQYYSTP

WTFGQGTKVEIKR,

Variant VL4: SEQ ID NO. 57):
MADYKDIQMTQSPSSVSASVGDRVTITCRASQNVDSAVAWYQQKPGKAPK

LLIYSASYRYSGVPSRFSGSGSGTDFTLTISSLQPEDFATYYCQQYYSTP

WTFGQGTKVEIKR,

Variant VL5: SEQ ID NO. 58):
MADYKDIQMTQSPSSVSASVGDRVTITCRASQNVDSAVAWYQQKPGKAPK

LLIYSASYRQSGVPSRFSGSGSGTDFTLTISSLQPEDFATYYCQQYYSTP

WTFGQGTKVEIKR,
and

Variant VL6: SEQ ID NO. 59):
MADYKDIQMTQSPSSVSASVGDRVTITCRASQNVDSAVAWYQQKPGKAPK

LLIYSASYGQSGVPSRFSGSGSGTDFTLTISSLQPEDFATYYCQQYYSTP

WTFGQGTKVEIKR,
or a combination thereof.

The present invention discloses a CD123 specific chimeric antigen receptor (CAR) as is described above, wherein said extra cellular ligand binding-domain VH and VL from a monoclonal anti-CD123 antibody respectively comprise at least one of the following sequences:

(SEQ ID NO. 60)
EVKLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS, (SEQ ID NO. 61)
EVQLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS, (SEQ ID NO. 62)
EVQLVESGGGLVQPGRSLRLSCTASGFTFTDYYMSWVRQAPGKGLEWVGL

IRSKADGYTTEYSASVKGRFTISRDDSKSIAYLQMNSLKTEDTAVYYCAR

DAAYYSYYSPEGAMDYWGQGTLVTVSS, (SEQ ID NO. 63)
EVQLVESGGGLVQPGRSLRLSCTASGFTFTDYYMSWVRQAPGKGLEWVGF

IRSKADGYTTEYSASVKGRFTISRDDSKSIAYLQMNSLKTEDTAVYYCAR

DAAYYSYYSPEGAMDYWGQGTLVTVSS, (SEQ ID NO. 64)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCAR

DAAYYSYYSPEGAMDYWGQGTLVTVSS, (SEQ ID NO. 65)
EVQLVESGGGLVQPGRSLRLSCTASGFTFTDYYMSWVRQAPGKGLEWVGL

IRSKADGYTTEYAASVKGRFTISRDDSKSIAYLQMNSLKTEDTAVYYCAR

DAAYYSYYSPEGAMDYWGQGTLVTVSS, (SEQ ID NO. 66)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCTR

DAAYYSYYSPEGAMDYWGQGTLVTVSS, (SEQ ID NO. 54)
MADYKDIVMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR, (SEQ ID NO. 55)
MADYKDIQMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR,

-continued

```
                                              (SEQ ID NO. 56)
MADYKDIQMTQSPSSVSASVGDRVTITCRASQNVDSAVAWYQQKPGKAPK

ALIYSASYRYSGVPSRFSGSGSGTDFTLTISSLQPEDFATYYCQQYYSTP

WTFGQGTKVEIKR, (SEQ ID NO. 57)
MADYKDIQMTQSPSSVSASVGDRVTITCRASQNVDSAVAWYQQKPGKAPK

LLIYSASYRYSGVPSRFSGSGSGTDFTLTISSLQPEDFATYYCQQYYSTP

WTFGQGTKVEIKR, (SEQ ID NO. 58)
MADYKDIQMTQSPSSVSASVGDRVTITCRASQNVDSAVAWYQQKPGKAPK

LLIYSASYRQSGVPSRFSGSGSGTDFTLTISSLQPEDFATYYCQQYYSTP

WTFGQGTKVEIKR,
and (SEQ ID NO. 59)
MADYKDIQMTQSPSSVSASVGDRVTITCRASQNVDSAVAWYQQKPGKAPK

LLIYSASYGQSGVPSRFSGSGSGTDFTLTISSLQPEDFATYYCQQYYSTP

WTFGQGTKVEIKR,
``` or a combination thereof.

Advantageously, the present invention discloses a CD123 specific chimeric antigen receptor (CAR) as described above, wherein said extra cellular ligand binding-domain VH and VL from a monoclonal anti-CD123 antibody respectively comprise at least one of the following sequences:

```
                                              (SEQ ID NO. 60)
EVKLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS, (SEQ ID NO. 61)
EVQLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS, (SEQ ID NO. 62)
EVQLVESGGGLVQPGRSLRLSCTASGFTFTDYYMSWVRQAPGKGLEWVGL

IRSKADGYTTEYSASVKGRFTISRDDSKSIAYLQMNSLKTEDTAVYYCAR

DAAYYSYYSPEGAMDYWGQGTLVTVSS, (SEQ ID NO. 63)
EVQLVESGGGLVQPGRSLRLSCTASGFTFTDYYMSWVRQAPGKGLEWVGF

IRSKADGYTTEYSASVKGRFTISRDDSKSIAYLQMNSLKTEDTAVYYCAR

DAAYYSYYSPEGAMDYWGQGTLVTVSS, (SEQ ID NO. 64)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCAR

DAAYYSYYSPEGAMDYWGQGTLVTVSS, (SEQ ID NO. 65)
EVQLVESGGGLVQPGRSLRLSCTASGFTFTDYYMSWVRQAPGKGLEWVGL

IRSKADGYTTEYAASVKGRFTISRDDSKSIAYLQMNSLKTEDTAVYYCAR

DAAYYSYYSPEGAMDYWGQGTLVTVSS, (SEQ ID NO. 66)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCTR

DDYYSYYSPEGAMDYWGQGTLVTVSS
``` and at least one of the following sequences:

```
                                              (SEQ ID NO. 54)
MADYKDIVMTQSPSSVSASVGDRVTITCRASQNVDSAVAWYQQKPGKAPK

ALIYSASYRYSGVPSRFSGRGSGTDFTLTISSLQPEDFATYYCQQYYST

PWTFGQGTKVEIKR, (SEQ ID NO. 55)
MADYKDIQMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR, (SEQ ID NO. 56)
MADYKDIQMTQSPSSVSASVGDRVTITCRASQNVDSAVAWYQQKPGKAPK

ALIYSASYRYSGVPSRFSGSGSGTDFTLTISSLQPEDFATYYCQQYYSTP

WTFGQGTKVEIKR, (SEQ ID NO. 57)
MADYKDIQMTQSPSSVSASVGDRVTITCRASQNVDSAVAWYQQKPGKAPK

LLIYSASYRYSGVPSRFSGSGSGTDFTLTISSLQPEDFATYYCQQYYSTP

WTFGQGTKVEIKR, (SEQ ID NO. 58)
MADYKDIQMTQSPSSVSASVGDRVTITCRASQNVDSAVAWYQQKPGKAPK

LLIYSASYRQSGVPSRFSGSGSGTDFTLTISSLQPEDFATYYCQQYYSTP

WTFGQGTKVEIKR, (SEQ ID NO. 59)
MADYKDIQMTQSPSSVSASVGDRVTITCRASQNVDSAVAWYQQKPGKAPK

LLIYSASYGQSGVPSRFSGSGSGTDFTLTISSLQPEDFATYYCQQYYSTP

WTFGQGTKVEIKR.
```

The present invention discloses a CD123 specific CAR as described above, wherein said structure V3 comprises a CD8 alpha hinge and a CD8 alpha transmembrane domain.

The present invention discloses a CD123 specific CAR as described above, wherein said structure V3 comprises a CD8 alpha hinge, 41BBS cytoplasmic domain and a CD8 alpha transmembrane domain.

The present invention discloses a CD123 specific CAR as described above, wherein said structure V3 comprises a CD8 alpha hinge and a 4-1BB transmembrane domain.

The present invention discloses a CD123 specific CAR as above, wherein said VH and VL have at least 80% identity with a polypeptide sequence selected from SEQ ID NO, 20 and SEQ ID NO. 19.

The present invention discloses a CD123 specific CAR as above, wherein said VH and VL have at least 80% identity with a polypeptide of SEQ ID NO. 20 and/or of SEQ ID NO. 19.

The present invention discloses a CD123 specific CAR as above further comprising another extracellular ligand binding domain which is not specific for CD123.

The present invention discloses a CD123 specific CAR as above, further comprising a signal peptide, preferably of SEQ ID NO 1 or SEQ ID NO 2.

The present invention discloses a CD123 specific CAR as above, wherein a linker of SEQ ID NO 10 is inserted between VH and VL The present invention discloses a polynucleotide encoding a CD123 specific chimeric antigen receptor according to any one of the CD123 specific CAR described above, said polynucleotide further comprising a signal peptide, preferably of SEQ ID NO 1 or SEQ ID NO 2.

The present invention discloses an expression vector comprising a polynucleotide as above.

The present invention discloses an engineered immune cell expressing at the cell surface membrane a CD123 specific chimeric antigen receptor as described above, preferably an engineered immune cell that can expressing at the cell surface membrane a CD123 specific chimeric antigen receptor as described above.

The present invention discloses an engineered immune cell as above, derived from T-lymphocytes, optionally resistant to an anti-cancer drug, and bearing a deletion in a gene coding an alpha TCR or a beta TCR. The present invention discloses an engineered immune cell as above, wherein expression of TCR is suppressed.

The present invention discloses an engineered immune cell as above, wherein expression of at least one MHC protein, preferably β2m or HLA, is suppressed In said engineered immune cell. β2m stands for beta 2 microglobulin and HLA for human leukocyte antigen. The MHC protein is a MHC protein of Class I or of class I, The present invention discloses an engineered immune cell as above, wherein said engineered immune cell is mutated to confer resistance to at least one immune suppressive drug, chemotherapy drug, or anti-cancer drug.

The present invention discloses an engineered immune cell as above for use in therapy.

The present invention discloses an engineered immune cell for use in therapy as above, wherein the patient is a human.

The present invention discloses an engineered immune cell for use in therapy as above, wherein the condition is a pre-malignant or malignant cancer condition characterized by CD123-expressing cells.

The present invention discloses an engineered immune cell for use in therapy as above, wherein the condition is a condition which is characterized by an overabundance of CD123-expressing cells.

The present invention discloses an engineered immune cell for use in therapy as above, wherein the malignant cancer condition is a haematological cancer condition.

The present invention discloses an engineered immune cell for use in therapy as above, wherein the haematological cancer condition is leukemia or malignant lymphoproliferative disorders.

The present invention discloses an engineered immune cell for use in therapy as above, wherein said leukemia is selected from the group consisting of acute myelogenous leukemia, chronic myelogenous leukemia, myelodysplastic syndrome, acute lymphoid leukemia, chronic lymphoid leukemia, and myelodysplastic syndrome.

The present invention discloses an engineered immune cell for use in therapy as above, wherein the leukemia is acute myelogenous leukemia (AML).

The present invention discloses an engineered immune cell for use in therapy as above, wherein said hematologic cancer is a malignant lymphoproliferative disorder.

The present invention discloses an engineered immune cell for use in therapy as above, wherein said malignant lymphoproliferative disorder is lymphoma.

The present invention discloses an engineered immune cell for use in therapy as above, wherein said lymphoma is selected from the group consisting of multiple myeloma, non-Hodgkin's lymphoma, Burkitt's lymphoma, and follicular lymphoma (small cell and large cell).

The present invention discloses a method of impairing a hematologic cancer cell comprising contacting said hematologic cancer cell with an engineered cell according to any one of claims 13 to 17 in an amount effective to cause Impairment of said cancer cell.

The present invention discloses a method of engineering an immune cell comprising:
(a) Providing an immune cell,
(b) Expressing at the surface of said cell at least one CD123 specific chimeric antigen receptor according to any one of claims 1 to 10.

The present invention discloses a method of engineering an immune cell as above comprising:
(a) Providing an immune cell,
(b) Introducing into said cell at least one polynucleotide encoding said CD123 specific chimeric antigen receptor,
(c) Expressing said polynucleotide into said cell. The present invention discloses a method of engineering an immune cell as above comprising:
(a) Providing an immune cell,
(b) Introducing into said cell at least one polynucleotide encoding said CD123 specific chimeric antigen receptor,
(c) Introducing at least one other chimeric antigen receptor which is not specific for CD123.

The present invention discloses a method of treating a subject in need thereof comprising:
(a) Providing an immune cell expressing at the surface a CD123 specific Chimeric Antigen Receptor according to any one of claims 1 to 10
(b) Administrating said immune cells to said patient.

The present invention discloses a method of treating a subject in need thereof as above, wherein said immune cell is provided from a donor.

The present invention discloses a method of treating a subject in need thereof as above, wherein said immune cell is provided from the patient himself.

CD123 specific Chimeric Antigen Receptors

The present invention relates to new designs of anti-CD123 chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In a preferred embodiment, said extracellular ligand-binding domain comprises a single chain antibody fragment (scFv) comprising the light ($V_L$) and the heavy ($V_H$) variable fragment of a target antigen specific monoclonal anti CD-123 antibody joined by a flexible linker. Said $V_L$ and $V_H$ are preferably selected from the antibodies referred to in the literature as 7G3, Old4, 26292, 32716, Klon43 and 12F1 as indicated in Table 1 to 8, more preferably Old4, Klon43 and 12F1, and even more preferably, Klon43. They are preferably linked together by a flexible linker comprising the sequence SEQ ID NO. 10. In other words, said CARs preferentially comprise an extracellular ligand-biding domain comprising a polypeptide sequence displaying at least 90%, 95% 97% or 99% identity with an amino acid sequence selected from the group consisting of SEQ ID NO: 11 to SEQ ID NO: 22 (see Table 2).

More preferably, said CARs preferentially comprise an extracellular ligand-biding domain comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%,or 99% identity with an amino acid sequence selected from the group consisting of SEQ ID NO: 13, 14, 19, 20, 21 to SEQ ID NO: 22 and even more preferably said CARs preferentially comprise an extracellular ligand-biding domain comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%,or 99% identity with amino acid sequences consisting of SEQ ID NO:19 and/or 20.

Even more preferably, said CARs comprise an extracellular ligand-biding domain comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%,or 99% identity with an amino acid sequence selected from the group consisting of SEQ ID NO: 1+ SEQ ID NO: 13, SEQ ID NO: 1+ SEQ ID NO: 14, SEQ ID NO: 1+ SEQ ID NO: 19, SEQ ID NO: 1+ SEQ ID NO: 20, SEQ ID NO: 1+SEQ ID NO: 21 and SEQ ID NO: 1+ SEQ ID NO: 22 and even more preferably said CARs preferentially comprise an extracellular ligand-biding domain comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%,or 99% identity with amino acid sequences consisting of SEQ ID NO: 1+ SEQ ID NO:19 and SEQ ID NO:1+ SEQ ID NO: 20.

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

As used herein, the term "conservative sequence modifications" or "humanization" is intended to refer to amino acid modifications that do not significantly affect or alter the binding characteristics of the CAR and/or that do not significantly affect the activity of the CAR containing the modified amino acid sequence and reduce or abolish a human antimouse antibody (HAMA) response., Such conservative modifications include amino acid substitutions, additions and deletions in said antibody fragment in said CAR and/or any of the other parts of said CAR molecule. Modifications can be introduced into an antibody, into an antibody fragment or in any of the other parts of the CAR molecule of the invention by standard techniques known in the art, such as site-directed mutagenesis, PCR-mediated mutagenesis or by employing optimized germline sequences.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind CD 123 using the functional assays described herein.

The signal transducing domain or Intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases, Examples of ITAM used in the invention can include as non limiting examples those derived from TCRzeta, FcRgamma, FcRbeta, FcRepsilon, CD3gamma, CD3delta, CD3epsilon, CDS, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% or 100% sequence identity with amino acid sequence selected from the group consisting of SEQ ID NO: 9.

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, 87-1 (CD80), 87-2 (CD86), PD-L1, PD-L2, 4-1BBL, OX4L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with 87-H3. A co-stimulatory ligand also encompasses, inter alia, an antibody that specifically binds with a co-stimulatory molecule present on a T cell, such as but not limited to, CD27, CD28, 4-188, OX40, CD30, CD40, PD-1, ICOS, lymphocyte function-associated antigen-1 (LFA-1), CD2, CD7, LTGHT, NKG2C, 67-H3, a ligand that specifically binds with CD83. A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-188 (CD137), OX40, CD30, CD40, PD-1, ICOS, lymphocyte function-associated antigen-1 (LFA-1), CD2, CD7, LIGHT, NKG2C, 87-H3 and a ligand that specifically binds with CD83 and the like.

In a preferred embodiment, the signal transduction domain of the CAR of the present invention comprises a part of co-stimulatory signal molecule selected from the group consisting of fragment of 4-188 (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ◻, polypeptide constituting CD3 complex, 112 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or CLEAN VERSION OF THE SUBSTITUTE SPECIFICATION polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to SO amino acids.

Hinge region may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIa receptor or IgG1 respectively referred to in this specification as SEQ ID NO. 3, SEQ ID NO. 4 and SEQ ID NO. 5, or hinge polypeptides which display preferably at least 80%, more preferably at least 90%, 95% 97% or 99% sequence identity with these polypeptides.

A car according to the invention generally further comprises a transmembrane domain (TM) more particularly selected from CD8a and 4-1BB, showing identity with the polypeptides of SEQ ID NO. 6 or 7.

A CAR according to the invention generally further comprises a transmembrane domain (TM) more particularly a TM selected from CD8α and 4-1BB, and even more particularly showing identity with the polypeptides of SEQ ID NO. 6 or 7.

in a preferred embodiment, a CAR according to the invention further comprises a TM domain from CD8α with SEQ ID NO. 6 or showing at least 90%, 91%, 92%, 93%, 94%, 95%, 96%, 97%, 98% or 99% sequence identity with SEQ ID NO. 6 Downregulation or mutation of target antigens is commonly observed in cancer cells, creating antigen-loss escape variants. Thus, to offset tumor escape and render immune cell more specific to target, the CD123 specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains., In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

In a preferred embodiment, a CAR according to the invention comprises a polypeptide of SEQ ID NO. 19 and/or a polypeptide of SEQ ID NO. 20, more preferably a CAR according to the invention comprises a polypeptide with at least 80% identity, preferably 80% to 99% identity with SEQ ID NO. 19 and/or a polypeptide having 80 to 99% identity with SEQ ID NO. 20. Even more preferably a CAR according to the invention comprises a polypeptide having 85 to 99% identity with a polypeptide of SEQ ID NO. 19 and/or SEQ ID NO. 20.

In a more preferred embodiment, a CAR according to the invention comprises a polypeptide having the following sequences:

(SEQ ID NO. 20)
EVKLVESGGGLVQPGGSLSLSCAASGFTFTDYYMSWVRQPPGKALEWLAL

IRSKADGYTTEYSASVKGRFTLSRDDSQSILYLQMNALRPEDSATYYCAR

DAAYYSYYSPEGAMDYWGQGTSVTVSS
and (SEQ ID NO. 19)
MADYKDIVMTQSHKFMSTSVGDRVNITCKASQNVDSAVAWYQQKPGQSPK

ALIYSASYRYSGVPDRFTGRGSGTDFTLTISSVQAEDLAVYYCQQYYSTP

WTFGGGTKLEIKR.

In one preferred embodiment, a CAR according to the invention comprises at least a polypeptide having the following sequence:

(SEQ ID NO. 60)
EVKLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS,

In one preferred embodiment, a CAR according to the invention comprises a polypeptide having the following sequence:

(SEQ ID NO. 61)
EVQLVESGGGLVQPGRSLRLSCTASGFTFTDYYMSWVRQAPGKGLEWVGL

IRSKADGYTTEYSASVKGRFTISRDDSKSILYLQMNSLKTEDTAVYYCAR

DAAYYSYYSPEGAMDYWGQGTLVTVSS

In one preferred embodiment, a CAR according to the invention comprises a polypeptide having the following sequence:

(SEQ ID NO. 62)
EVQLVESGGGLVQPGRSLRLSCTASGFTFTDYYMSWVRQAPGKGLEWVGL

IRSKADGYTTEYSASVKGRFTISRDDSKSIAYLQMNSLKTEDTAVYYCAR

DAAYYSYYSPEGAMDYWGQGTLVTVSS

In one preferred embodiment, a CAR according to the invention comprises a polypeptide having the following sequence:

(SEQ ID NO. 63)
EVQLVESGGGLVQPGRSLRLSCTASGFTFTDYYMSWVRQAPGKGLEWVGF

IRSKADGYTTEYSASVKGRFTISRDDSKSIAYLQMNSLKTEDTAVYYCAR

DAAYYSYYSPEGAMDYWGQGTLVTVSS

In one preferred embodiment, a CAR according to the invention comprises a polypeptide having the following sequence:

(SEQ ID NO. 64)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCAR

DAAYYSYYSPEGAMDYWGQGTLVTVSS

In one preferred embodiment, a CAR according to the invention comprises a polypeptide having the following sequence:

(SEQ ID NO. 65)
EVQLVESGGGLVQPGRSLRLSCTASGFTFTDYYMSWVRQAPGKGLEWVGL

IRSKADGYTTEYAASVKGRFTISRDDSKSIAYLQMNSLKTEDTAVYYCAR

DAAYYSYYSPEGAMDYWGQGTLVTVSS

In one preferred embodiment, a CAR according to the invention comprises a polypeptide having the following sequence:

(SEQ ID NO. 66)
EVQLVESGGGLVQPGRSLRLSCTASGFTFTDYYMSWVRQAPGKGLEWVGF

IRSKADGYTTEYAASVKGRFTISRDDSKSIAYLQMNSLKTEDTAVYYCTR

DAAYYSYYSPEGAMDYWGQGTLVTVSS.

In one preferred embodiment, a CAR according to the invention comprises a polypeptide having the following sequence:

(SEQ ID NO. 54)
MADYKDIVMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR

In one preferred embodiment, a CAR according to the invention comprises a polypeptide having the following sequence:

(SEQ ID NO. 55)
MADYKDIQMTQSPSSVSASVGDRVTITCRASQNVDSAVAWYQQKPGKAPK

ALIYSASYRYSGVPSRFSGRGSGTDFTLTISSLQPEDFATYYCQQYYSTP

WTFGQGTKVEIKR

In one preferred embodiment, a CAR according to the invention comprises a polypeptide having the following sequence:

(SEQ ID NO. 56)
MADYKDIQMTQSPSSVSASVGDRVTITCRASQNVDSAVAWYQQKPGKAPK

ALIYSASYRYSGVPSRFSGSGSGTDFTLTISSLQPEDFATYYCQQYYSTP

WTFGQGTKVEIKR

In one preferred embodiment, a CAR according to the invention comprises a polypeptide having the following sequence:

(SEQ ID NO. 57)
MADYKDIQMTQSPSSVSASVGDRVTITCRASQNVDSAVAWYQQKPGKAPK
LLIYSASYRYSGVPSRFSGSGSGTDFTLTISSLQPEDFATYYCQQYYSTP
WTFGQGTKVEIKR,

In one preferred embodiment, a CAR according to the invention comprises a polypeptide having the following sequence:

(SEQ ID NO. 58)
MADYKDIQMTQSPSSVSASVGDRVTITCRASQNVDSAVAWYQQKPGKAPK
LLIYSASYRQSGVPSRFSGSGSGTDFTLTISSLQPEDFATYYCQQYYSTP
WTFGQGTKVEIKR,

In one preferred embodiment, a CAR according to the invention comprises a polypeptide having the following sequence:

(SEQ ID NO. 59)
MADYKDIQMTQSPSSVSASVGDRVTITCRASQNVDSAVAWYQQKPGKAPK
LLIYSASYGQSGVPSRFSGSGSGTDFTLTISSLQPEDFATYYCQQYYSTP
WTFGQGTKVEIKR

In one preferred embodiment, a CAR according to the invention comprises at least one polypeptide selected from the following sequences:

(SEQ ID NO. 60)
EVKLVESGGGLVQPGRSLRLSCTASGFTFTDYYMSWVRQAPGKGLEWVGL
IRSKADGYTTEYSASVKGRFTISRDDSKSILYLQMNSLKTEDTAVYYCAR
DAAYYSYYSPEGAMDYWGQGTLVTVSS, (SEQ ID NO. 61)
EVQLVESGGGLVQPGRSLRLSCTASGFTFTDYYMSWVRQAPGKGLEWVGL
IRSKADGYTTEYSASVKGRFTISRDDSKSILYLQMNSLKTEDTAVYYCAR
DAAYYSYYSPEGAMDYWGQGTLVTVSS, (SEQ ID NO. 62)
EVQLVESGGGLVQPGRSLRLSCTASGFTFTDYYMSWVRQAPGKGLEWVGL
IRSKADGYTTEYSASVKGRFTISRDDSKSIAYLQMNSLKTEDTAVYYCAR
DAAYYSYYSPEGAMDYWGQGTLVTVSS, (SEQ ID NO. 63)
EVQLVESGGGLVQPGRSLRLSCTASGFTFTDYYMSWVRQAPGKGLEWVGF
IRSKADGYTTEYSASVKGRFTISRDDSKSIAYLQMNSLKTEDTAVYYCAR
DAAYYSYYSPEGAMDYWGQGTLVTVSS, (SEQ ID NO. 64)
EVQLVESGGGLVQPGRSLRLSCTASGFTFTDYYMSWVRQAPGKGLEWVGF
IRSKADGYTTEYAASVKGRFTISRDDSKSIAYLQMNSLKTEDTAVYYCAR
DAAYYSYYSPEGAMDYWGQGTLVTVSS, (SEQ ID NO. 65)
EVQLVESGGGLVQPGRSLRLSCTASGFTFTDYYMSWVRQAPGKGLEWVGL
IRSKADGYTTEYAASVKGRFTISRDDSKSIAYLQMNSLKTEDTAVYYCAR
DAAYYSYYSPEGAMDYWGQGTLVTVSS
and (SEQ ID NO. 66)
EVQLVESGGGLVQPGRSLRLSCTASGFTFTDYYMSWVRQAPGKGLEWVGF
IRSKADGYTTEYAASVKGRFTISRDDSKSIAYLQMNSLKTEDTAVYYCTR
DAAYYSYYSPEGAMDYWGQGTLVTVSS and at least one sequence selected from the following sequences (SEQ ID NO. 54)
MADYKDIVMTQSPSSVSASVGDRVTITCRASQNVDSAVAWYQQKPGKAPK
ALIYSASYRYSGVPSRFSGRGSGTDFTLTISSLQPEDFATYYCQQYYSTP
WTFGQGTKVEIKR, (SEQ ID NO. 55)
MADYKDIQMTQSPSSVSASVGDRVTITCRASQNVDSAVAWYQQKPGKAPK
ALIYSASYRYSGVPSRFSGRGSGTDFTLTISSLQPEDFATYYCQQYYSTP
WTFGQGTKVEIKR, (SEQ ID NO. 56)
MADYKDIQMTQSPSSVSASVGDRVTITCRASQNVDSAVAWYQQKPGKAPK
ALIYSASYRYSGVPSRFSGSGSGTDFTLTISSLQPEDFATYYCQQYYSTP
WTFGQGTKVEIKR, (SEQ ID NO. 57)
MADYKDIQMTQSPSSVSASVGDRVTITCRASQNVDSAVAWYQQKPGKAPK
LLIYSASYRYSGVPSRFSGSGSGTDFTLTISSLQPEDFATYYCQQYYSTP
WTFGQGTKVEIKR, (SEQ ID NO. 58)
MADYKDIQMTQSPSSVSASVGDRVTITCRASQNVDSAVAWYQQKPGKAPK
LLIYSASYRQSGVPSRFSGSGSGTDFTLTISSLQPEDFATYYCQQYYSTP
WTFGQGTKVEIKR
and (SEQ ID NO. 59)
MADYKDIQMTQSPSSVSASVGDRVTITCRASQNVDSAVAWYQQKPGKAPK
LLIYSASYGQSGVPSRFSGSGSGTDFTLTISSLQPEDFATYYCQQYYSTP
WTFGQGTKVEIKR.

In one preferred embodiment, a CAR according to the invention comprises one polypeptide selected from the following sequences: SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO 61, SEQ ID NO. 62, SEQ ID NO. 63, SEQ ID NO. 64, SEQ ID NO. 65, and, SEQ ID NO. 66.

In a more preferred embodiment, a CAR according to the invention comprises one polypeptide selected from the following sequences: SEQ ID NO. 54, SEQ ID NO. 55, SEQ ID NO. 56, SEQ ID NO. 57, SEQ ID NO. 58, SEQ ID NO. 59, and a peptide selected from the following sequences: SEQ ID NO. 60, SEQ ID NO. 61, SEQ ID NO. 62, SEQ ID NO. 63, SEQ ID NO. 64, SEQ ID NO. 65, and SEQ ID NO. 66.

In one embodiment, a CAR according to the invention comprises a polypeptide selected from the list consisting in SEQ ID NO. 42, SEQ ID NO. 44, and SEQ ID NO. 46, preferably a CAR comprising 80%, 81%, 82%, 83%, 84%, 85%, 86%, 87%, 88%, 89%, 90%, 91%, 92%, 93%, 94%, 95%, 96%, 97%, 98%,or 99% identity with a polypeptide of SEQ ID NO. 42, a CAR comprising 80%, 81%, 82%, 83%, 84%, 85%, 86%, 87%, 88%, 89%, 90%, 91%, 92%, 93%, 94%, 95%, 96%, 97%, 98%, or 99% identity with a polypeptide of SEQ ID NO. 44, and a CAR comprising 80%, 81%, 82%, 83%, 84%, 85%, 86%, 87%, 88%, 89%, 90%, 91%, 92%, 93%, 94%, 95%, 96%, 97%, 98%, or 99% identity with a polypeptide of SEQ ID NO. 46.

In a more preferred embodiment, a CAR according to the invention comprises a polypeptide comprising 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. 1+ SEQ ID NO. 42.

In another preferred embodiment, a CAR according to the invention comprises a polypeptide of SEQ ID NO. 10+ SEQ ID NO. 42, even more preferably a CAR comprising 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. 10+ SEQ ID NO. 42, in particular a CAR comprising 85% to 99% identity with SEQ ID NO. 10+ SEQ ID NO. 42.

In a more preferred embodiment, a CAR according to the invention comprises a polypeptide comprising 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. 1+ SEQ ID NO. 44.

In an even more preferred embodiment, a CAR according to the invention comprises a polypeptide of SEQ ID NO. 10+ SEQ ID NO. 44, even more preferably a CAR comprising 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. 10+ SEQ ID NO. 44, in particular a CAR comprising 85% to 99% identity with SEQ ID NO. 10+ SEQ ID NO. 44.

In a more preferred embodiment, a CAR according to the invention comprises a polypeptide comprising 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO. 1+ SEQ ID NO. 46.

In an even more preferred embodiment, a CAR according to the invention comprises a polypeptide of SEQ ID NO. 10+ SEQ ID NO. 46, even more preferably a CAR comprising 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. 10+ SEQ ID NO. 46, in particular a CAR comprising 85% to 99% identity with SEQ ID NO. 10+ SEQ ID NO. 46.

In another preferred embodiment, a CAR according to the invention consists in a polypeptide of SEQ ID NO. 1+ SEQ ID NO. 10+ SEQ ID NO. 42 even more preferably a CAR is consisting in 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. SEQ ID NO. 1+ SEQ ID NO. 10+SEQ ID NO. 42.

In another preferred embodiment, a CAR according to the invention consists in a polypeptide of SEQ ID NO. SEQ ID NO. 1+ SEQ ID NO. 10+ SEQ ID NO. 44 even more preferably a CAR is consisting in 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. SEQ ID NO. 1+ SEQ ID NO. 10+ SEQ ID NO. 44.

In another preferred embodiment, a CAR according to the invention consists in a polypeptide of SEQ ID NO. SEQ ID NO. 1+ SEQ ID NO. 10+ SEQ ID NO. 46 even more preferably a CAR is consisting in 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO. SEQ ID NO. 1+ SEQ ID NO. 10+ SEQ ID NO. 46.

According to the invention, the immune cells expressing the anti-CD123 CAR of the invention trigger an anti-cancer immune response. In a preferred embodiment, the immune cells expressing the CAR of the invention endowed with the anti-CD123 CAR of the invention does trigger an immune response which does not comprise a human anti-mouse antibody (HAMA) response.

According to the invention, an efficient amount of the engineered immune cell can be administered to a patient in need thereof at least once, twice, or several times, alone or in combination with another treatment.

The present invention concerns a CD123 specific chimeric antigen receptor (CAR) having one of the polypeptide structure selected from V1 to V6 as illustrated in FIG. 2, said structure comprising an extra cellular ligand binding-domain comprising VH and VL from a monoclonal anti-CD123 antibody, a hinge, a transmembrane domain and a cytoplasmic domain including a CD3 zeta signaling domain and a co-stimulatory domain from 4-188.

Polynucleotides, Vectors:

The present invention also relates to polynucleotides, vectors encoding the above described CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame.

Such ribosomal skip mechanisms are well known in the art and are known to be used by several vectors for the expression of several proteins encoded by a single messenger RNA. To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al, U.S. Pat. No. 5,037,743; Holland et al., U.S. Pat. No. 5,143,830). in a preferred embodiment the signal peptide comprises the amino acid sequence SEQ ID NO: 1 and 2 or at least 90%, 95% 97% or 99% sequence identity with SEQ ID NO: 1 and/or 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent In highly expressed genes of such species, such codons encoding the amino acids as the codons that are being exchanged.

Cells

Cell according to the present invention refers to a cell of hematopoietic origin functionally involved in the initiation and/or execution of innate and/or adaptive immune response. Cell according to the present invention is preferably a T-cell obtained from a donor. Said T cell according to the present invention can be derived from a stem cell. The stem cells can be adult stem cells, embryonic stem cells, more particularly non-human stem cells, cord blood stem cells, progenitor cells, bone marrow stem cells, totipotent stem cells or hematopoietic stem cells. In a preferred embodiment, cells are human cells, in particular human stem cells.

Representative human stem cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available and known to those skilled in the art, may be used. In another embodiment, said cell is preferably derived from a healthy donor. In another embodiment, said cell is part of a mixed population of cells which present different phenotypic characteristics.

Preferably, isolation and preparation of stem cells does not require the destruction of at least one human embryo. The immune cells can originate from the patient, in view of operating autologous treatments, or from donors in view of producing allogeneic cells, which can be used in allogeneic treatments.

More preferably the immune cell of the invention express an anti-CD123 CAR corresponding to SEQ ID NO 42, SEQ ID NO 44,or SEQ ID NO 46, even more preferably the immune cell of the invention express an humanized anti-CD123 CAR corresponding to humanized SEQ ID NO 42, SEQ ID NO 44,or SEQ ID NO 46.

Methods of Engineering Immune Cells Endowed with CARs:

The present invention encompasses the method of preparing immune cells for immunotherapy comprising introducing ex-vivo into said immune cells the polynucleotides or vectors encoding the CD123 CAR previously described in WO2014/130635, WO2013176916, WO2013176915 and incorporated herein by reference.

In a preferred embodiment, said polynucleotides are included in lentiviral vectors in view of being stably expressed in the immune cells.

According to further embodiments, said method further comprises the step of genetically modifying said cell to make them more suitable for allogeneic transplantation.

Modifying T-Cell by Inactivating at Least One Gene Encoding a T-Cell Receptor (TCR) Component.

According to a first aspect, the immune cell can be made less allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced.

Accordingly, when the immune cells are T-cells, the present invention also provides methods to engineer T-cells that are less allogeneic.

Methods of making cells less allogenic can comprise the step of inactivating at least one gene encoding a T-Cell Receptor (TCR) component, in particular TCRalpha, TCR-beta genes.

Methods disclosed in WO2013/176915 to prepare CAR expressing immune cell suitable for allogeneic transplantation, by inactivating one or more component of T-cell receptor (TCR), are all incorporated herein by reference.

The present invention encompasses an anti-CD123 CAR expressing immune cell wherein at least one gene expressing one or more component of T-cell receptor (TCR) has been inactivated. Thus, the present invention provides an anti-CD123 CAR expressing T cell wherein the CAR is derived from Klon 43, in particular having at least 80% identity with SEQ ID N" 44 and wherein at least one gene expressing one or more component of T-cell receptor (TCR) is inactivated.

According to the invention, anti-CD123 CAR immune cells with one or more component of T-cell receptor (TCR) inactivated, are intended to be used as a medicament.

By inactivating a TCR gene it is intended that the gene of interest is not expressed in a functional protein form. In particular embodiments, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art. In a particular embodiment, the step of inactivating at least a gene encoding a component of the T-cell receptor (TCR) into the cells of each individual sample comprises introducing into the cell a rare-cutting endonuclease able to disrupt at least one gene encoding a component of the T-cell receptor (TCR). In a more particular embodiment, said cells of each individual sample are transformed with nucleic acid encoding a rare-cutting endonuclease capable of disrupting at least one gene encoding a component of the T-cell receptor (TCR), and said rare-cutting endonuclease is expressed into said cells.

Said rare-cutting endonuclease can be a meganuclease, a Zinc finger nuclease, CRISPR/Cas9 nuclease, Argonaute nuclease, a TALE-nuclease or a MBBBD-nuclease. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012). In the present invention new TALE-nucleases have been designed for precisely targeting relevant genes for adoptive immunotherapy strategies.

Preferred TALE-nucleases recognizing and cleaving the target sequence are described in PCT/EP2014/075317. In particular, additional catalytic domain can be further introduced into the cell with said rare-cutting endonuclease to increase mutagenesis in order to enhance their capacity to inactivate targeted genes. More particularly, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExol (EX-Ol_HUMAN), Yeast Exol (EXOl_YEAST), E. coli Exol, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX2 polypeptide. Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells of an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. In a particular embodiment, the homologous sequence can be from 200 bp to 6000 bp, more preferably from 1000 bp to 2000 bp, Indeed, shared nucleic acid homologies are located in regions flanking upstream and downstream the site of the break and the nucleic acid sequence to be introduced should be located between the two arms.

Immune Check Points

The present invention provides allogeneic T-cells expressing an anti-CD123 CAR, in particular an anti-CD123 CAR of SEQ ID N'44, or of SEQ ID N' 1+ SEQ ID N' 44, wherein at least one gene expressing one or more component of T-cell receptor (TCR) is inactivated and/or one gene selected from the genes CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGF≠BRII. TGFBRI, SMAD2, SMAD3, SMAD4, SMAD10, SKI, SKIL, TGIF1, ILIORA, IL10RB, HMOX2, IL6R, IL6ST, CSK, PAG1, SITI, FOXP3, PRDMI (orblimpl), BATF, GUCYIA2, GUCY1A3, GUCY182, GUCY183, is inactivated as referred to in WO2014/184741.

Drug Resistant T-Cells

According to another aspect, the anti-CD123 CAR expressing T-cell of the invention can be further genetically engineered to improve its resistance to immunosuppressive drugs or chemotherapy treatments, which are used as standard care for treating CD123 positive malignant cells.

Several cytotoxic agents (anti-cancer drugs) such as antimetabolites, alkylating agents, anthracyclines, DNA methyltransferase inhibitors, platinum compounds and spindle poisons have been developed to kill cancer cells. However, the introduction of these agents with novel therapies, such as immunotherapies, is problematic. For example, chemotherapy agents can be detrimental to the establishment of robust anti-tumor immunocompetent cells due to the agents' non-specific toxicity profiles. Small molecule-based therapies targeting cell proliferation pathways may also hamper the establishment of anti-tumor immunity. If chemotherapy regimens that are transiently effective can be combined with novel immunocompetent cell therapies then significant improvement in anti-neoplastic therapy might be achieved (for review (Dasgupta, McCarty et al. 2011)).

To improve cancer therapy and selective engraftment of allogeneic T-cells, drug resistance is conferred to said allogeneic T cells to protect them from the toxic side effects of chemotherapy agent. The drug resistance of T-cells also permits their enrichment in or ex vivo, as T-cells which express the drug resistance gene will survive and multiply relative to drug sensitive cells.

Methods for engineering T-cells resistant to chemotherapeutic agents are disclosed in PCT/EP2014/075317 which is fully Incorporated by reference herein.

In particular, the present invention relates to a method of engineering allogeneic cells suitable for immunotherapy wherein at least one gene encoding a T-cell receptor (TCR) component is inactivated and one gene is modified to confer drug resistance comprising:

Providing an anti-CD123 CAR expressing T-cell; in particular an anti-CD123 CAR of SEQ ID NO' 42, SEQ ID NO'44, SEQ ID NO 46 expressing T cell, preferably humanized 123 CAR of SEQ ID NO' 42, SEQ ID NO'44, SEQ ID NO 46

Modifying said anti-CD123 CAR expressing T-cell by inactivating at least one gene encoding a T-cell receptor (TCR) component;

Modifying said anti-CD123 CAR expressing T-cell to confer drug resistance to said anti-CD123 CAR expressing T-cell;

Expanding said engineered anti-CD123 CAR expressing T-cell in the presence of said drug.

Alternatively, the present invention relates to a method comprising:

Providing an anti-CD123 CAR expressing T-cell; in particular an anti-CD123 CAR of SEQ ID N'42 SEQ ID NO 4, SEQ ID NO 46 expressing T cell, preferably humanized 123 CAR of SEQ ID NO'42, SEQ ID NO'44, SEQ ID NO 46

Modifying said anti-CD123 CAR expressing T-cell to confer drug resistance to is said anti-CD123 CAR expressing T-cell;

Modifying said anti-CD123 CAR expressing T-cell by inactivating at least one gene encoding a T-cell receptor (TCR) component;

Expanding said engineered anti-CD123 CAR expressing T-cell in the presence of said drug.

In particular, the present invention also relates to a method of engineering allogeneic cells suitable for immunotherapy wherein at least one gene encoding a T-cell receptor (TCR) component is inactivated and one gene is modified to confer drug resistance comprising:

Providing an anti-CD123 CAR expressing T-cell; in particular an anti-CD123 CAR of SEQ ID NO'75, SEQ ID NO' 76, SEQ ID NO 77 expressing T cell, preferably humanized 123 CAR of SEQ ID NO' 75, SEQ ID NO'76, SEQ ID NO 77, more preferably humanized 123 CAR of SEQ ID NO' 75, Modifying said anti-CD123 CAR expressing T-cell by inactivating at least one gene encoding a T-cell receptor (TCR) component;

Modifying said anti-CD123 CAR expressing T-cell to confer drug resistance to said anti-CD123 CAR expressing T-cell;

Expanding said engineered anti-CD123 CAR expressing T-cell in the presence of said drug.

Alternatively, the present invention relates to a method comprising:

Providing an anti-CD123 CAR expressing T-cell; in particular an anti-CD123 CAR of SEQ ID NO 75, SEQ ID NO' 76, SEQ ID NO 77 expressing T cell, preferably humanized 123 CAR of SEQ ID NO 475, SEQ ID NO 76, SEQ ID NO 77, more preferably humanized 123 CAR of SEQ ID NO' 75, Modifying said anti-CD123 CAR expressing T-cell to confer drug resistance to said anti-CD123 CAR expressing T-cell;

Modifying said anti-CD123 CAR expressing T-cell by inactivating at least one gene encoding a T-cell receptor (TCR) component; Expanding said engineered anti-CD123 CAR expressing T-cell in the presence of said drug.

Expression of drug resistance genes in anti-CD123 CAR-expressing immune cells in a particular embodiment, said drug resistance can be conferred to the T-cell by the expression of at least one drug resistance gene. Said drug resistance gene refers to a nucleic acid sequence that encodes "resistance" to an agent, such as a chemotherapeutic agent (e.g. methotrexate). in other words, the expression of the drug resistance gene in a cell permits proliferation of the cells in the presence of the agent to a greater extent than the proliferation of a corresponding cell without the drug resistance gene. The expression of the drug resistance gene in a cell permits proliferation of the cells in the presence of the agent and does not affect its activity. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

In one embodiment, a drug resistance gene of the invention can confer resistance to a drug (or an agent), in particular an anti-cancer drug selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, combination of arsenic trioxyde, transretinoic acid, mechlorethamine, procarbazine, chlorambucil, cytarabine, anthracyclines, 6-thioguanine, hydroxyurea, prednisone, and combination thereof.

Several drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis, Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer, Dicker et al, 1990); International application WO94/24277; US patent U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide set forth in GenBank: AAH71996,1. In a particular embodiment, the serine residue at position 1S is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino- 4-deoxypteroyl)-N delta-hemiphthaloyi-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of lonisine-5'-monophosphate dehydrogenase II (IMPDH2), a rate-limiting enzyme in the de nova synthesis of guanosine nucleotides. The mutant or modified form of IMPDH2 is an IMPDH inhibitor resistance gene. IMPDH inhibitors can be mycophenolic acid (MPA) or its prodrug mycophenolate mofetil (MMF). The mutant IMPDH2 can comprises at least one, preferably two mutations In the MAP binding site of the wild type human IMPDH2 (NP_000875.2) that lead to a significantly increased resistance to IMPDH inhibitor. The mutations are preferably at positions T333 and/or S351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue. Correspondence of amino acid positions described herein is frequently expressed in terms of the positions of the amino acids of the form of wild-type human IMPDH2 polypeptide set forth in NP_000875.2.

Another drug resistance gene is the mutant form of calcineurin. Calcineurin (PP2B), an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms)., After engagement of the T-cell receptor, calcineurin dephosphorylates the transcription factor NFAT, allowing it to translocate to the nucleus and active key target gene such as 112. FKS06 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA>In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine residue at position 354 can be replaced with an alanine residue; the lysine at position 360 can be replaced with an alanine or phenylaianine residue of a sequence corresponding to GenBank: ACX34092.1. Correspondence of amino acid positions described herein is frequently expressed in terms of the positions of the amino acids of the form of wild-type human calcineurin heterodimer a polypeptide set forth in (GenBank: ACX34092.1).

In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylaianine or leucine residue; the asparagine at position 123 can be replaced with a tryptophan, lysine, phenylaianine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence corresponding to GenBank: ACX34095.1. Correspondence of amino acid positions described herein is frequently expressed in terms of the positions of the amino acids of the form of wild-type human calcineurin heterodimer b polypeptide set forth in (GenBank: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-8G) is an Inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-1G, but retain their ability to repair DNA damage (Maze, Kurpad et al. 1999). In a particular embodiment, AGT mutant form can comprise a mutated amino acid of the wild type AGT position P140, in the amino acid sequence SEQ ID NO: 18 (UniProtKB: P16455). In a preferred embodiment, said proline at position 140 is replaced with a lysine residue.

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents.

Overexpressing multidrug resistance protein 1 has been described to confer resistance to drugs such as Mitoxantrone (Charles S. Morrow, Christina Pekiak-Scott, Bimjhana Bishwokarma, Timothy E. Kute, Pamela K. Smitherman, and Alan J. Townsend.

Multidrug Resistance Protein 1 (MRP1, ABCC1) Mediates Resistance to Mitoxantrone via Glutathione-Dependent Drug Efflux MolPharmacol Apr. 2006 69:1499-1505).

Thus, drug resistance can be conferred to cells by the expression of nucleic acid sequence that encodes MDR-1 (NP.000918).

Still another way of preparing drug resistant cells is to prepare cells with specific mutation (s) such as mutations at Arg486 and Glu571 in the Human Topoisomerase II gene, to confer resistance to amsacrine (S. PATEL, 8. A. KELLER, and L. M. FISHER. 2000. MOLECULAR PHARMACOLOGY. Vol 57: p784-791 (2000).

Still another way of preparing drug resistant cells is to prepare cells overexpressing microRNA-21 to confer resistance to Daunorubicine (involvement of miR-21 in resistance to daunorubicin by regulating PTEN expression in the leukaemia K562 cell line Bai, Haitao et al. FEBS Letters, Volume 585, Issue 2, 402-408).

In a preferred embodiment, cells bearing such a drug resistance conferring mRNA or protein also comprise an inhibitory mRNA or a gene the expression of which is conditioned, allowing the selective destruction of said drug resistant cells in the presence of said drug or upon administration of said drug.

Drug resistance gene can also confer resistance to cytotoxic antibiotics, and can be ble gene or mcrA gene. Ectopic expression of ble gene or mcrA in an immune cell gives a selective advantage when exposed to the chemotherapeutic agent, respectively the bleomycine or the mitomycin C.

The most practical approach to gene therapy is the addition of a gene to engineer T-cell by using efficient gene delivery with vectors, preferably viral vector. Thus, in a particular embodiment, said drug resistance gene can be expressed in the cell by introducing a transgene preferably encoded by at least one vector into a cell.

In one embodiment, cells bearing a drug resistance gene or a modified gene conferring resistance to a drug also comprise an inducible suicide gene—the induction of which provokes cell death-allowing their selective destruction.

The random insertion of genes into the genome may lead to the inappropriate expression of the inserted gene or the gene near the insertion site. Specific gene therapy using homologous recombination of exogenous nucleic acid comprising endogenous sequences to target genes to specific sites within the genome can allow engineering secure T-cells. As described above, the genetic modification step of the method can comprise a step of introduction into cells of an exogeneous nucleic acid comprising at least a sequence encoding the drug resistance gene and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Endonucleolytic breaks are known to stimulate the rate of homologous recombination. Thus, in a particular embodiment, the method of the invention further comprises the step of expressing in the cell a rare-cutting endonuclease which is able to cleave a target sequence within an endogenous gene. Said endogenous gene can encode for examples DHFR, IMPDH2, calcineurin or AGT. Said rare-cutting endonuclease can be a TALE-nuclease, a Zinc finger nuclease, a CRISPR/Cas9 endonuclease, a MBBBD-nuclease or a meganuclease.

Inactivation of Drug Sensitizing Genes in Anti-CD123 CAR-Expressing Immune Cells in another particular embodiment, said drug resistance can be conferred to the cell of the invention (anti-CD123 CAR expressing immune cell,) by the inactivation of a drug sensitizing gene.

The inventor sought to inactivate potential drug sensitizing gene to engineer T-cell for immunotherapy, in particular to engineer anti-CD123 CAR expressing immune cell that can be used in combination with a therapeutic agent (anti-cancer drug).

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, the step of inactivating at least one drug sensitizing gene comprises introducing into the cell a rare-cutting endonuclease able to disrupt at least one drug sensitizing gene. In a more particular embodiment, said cells are transformed with nucleic acid encoding a rare-cutting endonuclease capable of disrupting a drug sensitizing gene, and said rare-cutting endonuclease is expressed into said cells. Said rare-cutting endonuclease can be a meganuclease, a Zinc finger nuclease, CRISPR/Cas9 nuclease, A MBBBD-nuclease or a TALE-nuclease. In a preferred embodiment, said rare-cutting endonuclease is a TALE-nuclease.

In a preferred embodiment, drug sensitizing gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA, Their triphosphate forms and particularly clofarabine triphosphate compete with ATP for DNA synthesis, acts as proapoptotic agent and are potent inhibitors of ribonucleotide reductase (RNR) which is involved in trinucleotide production.

Preferably, the inactivation of dCK in T cells is mediated by TALE nuclease. To achieve this goal, several pairs of dCK TALE-nuclease have been designed, assembled at the polynucleotide level and validated by sequencing. Examples of TALE-nuclease pairs which can be used according to the invention are depicted in PCT/EP2014/075317.

This dCK Inactivation in T cells confers resistance to purine nucleoside analogs (PNAs) such as clofarabine and fludarabine.

In another preferred embodiment, the dCK inactivation in T cells is combined with an inactivation of TRAC genes rendering these double knock out (KO) T cells both resistant to drug such as clofarabine and less allogeneic. This double features is particularly useful for a therapeutic goal, allowing "off-the-shelf" allogeneic cells for immunotherapy in conjunction with chemotherapy to treat patients with cancer. This double KO inactivation dCK/TRAC can be performed simultaneously or sequentially. One example of TALE-nuclease dCK/TRAC pairs which gave success in the invention is described in PCT/EP2014/075317, in particular, the target sequences in the 2 loci (dCK and TRAC).

Another example of enzyme which can be inactivated is human hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, In particular leukemias (Hacke, Treger et al. 2013). Guanines analogs are metabolized by HPRT transferase that catalyzes addition of phosphoribosyl moiety and enables the formation of TGMP Guanine analogues including 6 mercapthopurine (6MP) and 6 thioguanine (6TG) are usually used as lymphodepleting drugs to treat ALL. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate groupment and generate random point mutation that are highly deleterious for cell integrity.

In another embodiment, the inactivation of the CD3 normally expressed at the surface of the T-cell can confer resistance to anti-CD3 antibodies such as teplizumab.

The terms "therapeutic agent", "chemotherapeutic agent", or "drug" or "anti-cancer drug" as used herein refers to a medicament, preferably a compound or a derivative thereof that can interact with a cancer cell, thereby reducing the proliferative status of the cell and/or killing the cell. Examples of chemotherapeutic agents or "anti-cancer drug"

include, but are not limited to, alkylating agents (e.g., Busulfan • Carboolatine • Chlorambucil • Cisplatine • Cyclophosphamide a Ifosfamide • Melphalan • Mkchlorkthamine • Oxaliplatine SUramustine • Temozolomide • Fotemustine), metabolic antagonists (e.g., purine nucleoside antimetabolite such as ciofarabine, fludarabine or 2'-deoxyadenosine, methotrexate (MTX), 5-fluorouracil or derivatives thereof, Azathioprine • Capecitabine • Cytarabine • Floxuridine • Fluorouracile • Gemcitabine • Methotrexate • Pemetrexed), antitumor antibiotics (e.g., mitomycin, Adriamycin, Bleomycine • Daunorubicine • Doxorubicine • Epirubicine • Hydroxyurea a Idarubicine • Mitomycin C • Mitoxantrone), plant-derived antitumor agents (e.g., vincristine, vindesine, Taxol, Vinblastine • (Vinorelbine) • Docetaxel • Paclitaxel), topoisomerase inhibitor (Irinotecan • Topotecan a Etoposide), in a preferred embodiment, a therapeutic agent, a chemotherapy drug as used herein refers to a compound or a derivative thereof that may be used to treat cancer, in particular to treat a hematopoietic cancer cell and more particularly AML, thereby reducing the proliferative status of the cancer cell and/or killing the cancer cell. Examples of chemotherapeutic agents include, but are not limited to Aracytine, Cytosine Arabinoside, Amsacrine, Daunorubicine, Idarubicine, Novantrone, Mitoxantrone, Vepeside, Etoposide (VP16), arsenic trioxyde, transretinoic acid, mechlorethamine, procarbazine, chlorambucil, and combination thereof.

In other embodiments of the present invention, cells of the invention are administered to a patient in conjunction with a drug (or an agent) selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, cytarabine, anthracyclines, 6-thioguanine, hydroxyurea, prednisone, and combination thereof.

Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR),6-benzyguanidine (6-BG), bis-chloronitrosourea (BCNU) and CAMPTOTHECIN" ", or a therapeutic derivative of any thereof.

In a more preferred embodiment an anti-CD123 CAR of SEQ ID N' 44 expressing T cell, is administered to a patient, in combination with at least one therapeutic agent selected from Aracytine, Cytosine Arabinoside, Amsacrine, Daunorubicine, Idarubicine, Novantrone, Mitoxantrone, Vepeside, Etoposide (VP16), arsenic trioxyde, transretinoic acid and combination thereof.

As used herein, a cell which is "resistant or tolerant" to an agent means a cell which has been genetically modified so that the cell proliferates in the presence of an amount of an agent that inhibits or prevents proliferation of a cell without the modification.

Multiple Drug Resistance of Anti-CD123 CAR-Expressing Immune Cells

In another particular embodiment, the inventors sought to develop an "off-the shelf" immunotherapy strategy, using allogeneic T-cells, in particular allogenic anti-CD123 CAR expressing T-cell resistant to multiple drugs to mediate selection of engineered T-cells when the patient is treated with different drugs. The therapeutic efficiency can be significantly enhanced by genetically engineering multiple drug resistance allogeneic T-cells. Such a strategy can be particularly effective in treating tumors that respond to drug combinations that exhibit synergistic effects. Moreover multiple resistant engineered T-cells can expand and be selected using minimal dose of drug agents.

Thus, the method according to the present invention can comprise modifying T-cell to confer multiple drug resistance to said T-cell. Said multiple drug resistance can be conferred by either expressing more than one drug resistance gene or by inactivating more than one drug sensitizing gene. In another particular embodiment, the multiple drug resistance can be conferred to said T-cell by expressing at least one drug resistance gene and inactivating at least one drug sensitizing gene. In particular, the multiple drug resistance can be conferred to said T-cell by expressing at least one drug resistance gene such as mutant form of DHFR, mutant form of IMPDH2, mutant form of calcineurin, mutant form of MGMT, the ble gene, and the mcrA gene and inactivating at least one drug sensitizing gene such as HPRT gene. In a preferred embodiment, multiple drug resistance can be conferred by inactivating HPRT gene and expressing a mutant form of DHFR; or by inactivating HPRT gene and expressing a mutant form of IMPDH2; or by inactivating HPRT gene and expressing a mutant form of calcineurin; by inactivating HPRT gene and expressing a mutant form of MGMT; by inactivating HPRT gene and expressing the ble gene; by inactivating HPRT gene and expressing the mcrA gene.

In one embodiment, the present invention provides allogenic anti-CD123 CAR expressing T-cell expressing more than one drug resistance gene or wherein more than one drug sensitizing gene is inactivated.

Suicide Genes in Anti-CD123 CAR-Expressing Immune Cells

In some instances, since engineered T-cells can expand and persist for years after administration, it can be desirable to include a safety mechanism to allow selective deletion of administrated T-cells. Thus, in some embodiments, the method of the invention can comprises the transformation of said T-cells with a recombinant suicide gene. Said recombinant suicide gene is used to reduce the risk of direct toxicity and/or uncontrolled proliferation of said T-cells once administrated in a subject (Quintarelli C, Vera F, blood 2007; Tey S K, Dotti G., Rooney C M, boil blood marrow transplant 2007). Suicide genes enable selective deletion of transformed cells in vivo. In particular, the suicide gene has the ability to convert a non-toxic pro-drug into cytotoxic drug or to express the toxic gene expression product. In other words, "Suicide gene" is a nucleic acid coding for a product, wherein the product causes cell death by itself or in the presence of other compounds.

A representative example of such a suicide gene is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil. Suicide genes also include as non limiting examples caspase-9 or caspase-8 or cytosine deaminase. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU (1-(2-deoxy-2-fluoro-β-D-arabinofuranosyl)-5-iodouracill, 6-methoxypurine arabinoside for VZV-TK, and 5-fluorocytosine for cytosine deaminase.

One preferred suicide gene system employs a recombinant antigenic polypeptide comprising antigenic motif recognized by the anti-CD20 mAb Rituximab, especially Q8en10, such as in the so-called RQR8 polypeptide described in WO2013153391. Rituximab, an authorized antibody drug, can then be used for cell depletion when needed.

In one embodiment, the present invention provides allogenic anti-CD123 CAR expressing T-cell expressing more than one drug resistance gene or wherein more than one drug sensitizing gene is inactivated, and a suicide gene allowing said cells to be destroyed.

Clofarabine Resistant Anti-CD123 CAR-Expressing Immune Cells

The invention encompasses the manufacture of T cells for therapeutic use, which are resistant a drug such as to Clofarabine. They can be obtained by inactivation of the dCK gene such as previously explained, According to a preferred embodiment, the T-cells are made resistant to chemotherapy and less allogeneic by combining inactivation of dCK and TCR genes as previously described.

Thus, the present invention provides an anti-CD123 CAR expressing cell, in particular an anti-CD123 CAR expressing T cell wherein the CAR is derived from Klon 43 (comprising a SEQ ID N042 or SEQ ID NO. 44. optionally humanized) and wherein the dCK gene is inactivated.

CD123+/Luc+ Drug Resistant Daudi Cells for Testing the Cytotoxicity of Drug Resistant Allogenic CAR T Cells The present invention encompasses also a method for manufacturing target cells which express both a surface receptor specific to the CAR T cells and a resistance gene. These target cells are particularly useful for testing the cytotoxicity of CAR T cells. These cells are readily resistant to clinically relevant dose of clofarabine and harbor luciferase activity. This combination of features enable traking them in vivo in a mice model or destroy them when required.

More particularly, they can be used to assess the cytotoxicity properties drug resistant T cells in mice in the presence of clofarabine or other PNAs. Clofarabine resistant Daudi cells mimick the physiological state of acute lymphoblastic leukemia (ALL) patients relapsing form induction therapy, that harbor drug resistant B cell malignancies. Thus, these cells are of great interest to evaluate the reliability and cytotoxicity of drug resistant CART cells.

Preferably, these target cells are CD123+Luciferase+ Daudi cells.

Isolated Cell

The present invention relates to an isolated cell expressing a CAR which binds to CD123. Thus, the invention relates to an anti-CD123 CAR expressing cell. In a particular embodiment, said anti-CD123 CAR expressing cell is resistant to at least one drug and/or comprises at least one disrupted gene encoding a T-cell receptor component.

In a preferred embodiment, the present invention relates to an isolated T cell expressing a CAR which binds to CD123. The invention relates to an anti-CD123 CAR expressing T-cell. In a particular embodiment, said anti-CD123 CAR expressing T cell is resistant to at least one drug and/or comprises at least one disrupted gene encoding a T-cell receptor component.

In a particular embodiment, said anti-CD123 CAR T-cell expresses at least one drug resistance gene, preferably ble gene or mcrA gene or gene encoding a mutant DHFR, a mutant IMPDH2, a mutant AGT or a mutant calcineurin.

In another particular embodiment, said anti-CD123 CAR expressing T cell comprises at least one disrupted drug sensitizing gene such as dCK or HPRT gene. In a more particular embodiment, said isolated anti-CD123 CAR T-cell comprises a disrupted HPRT gene and express a DHFR mutant; said isolated anti-CD123 CAR T-cell comprises a disrupted HPRT gene and express a IMPDH2 mutant; said isolated anti-CD123 CAR T-cell comprises a disrupted HPRT gene and express a calcineurin mutant; said isolated anti-CD123 CAR T-cell comprises a disrupted HPRT gene and express a AGT mutant.

Allogeneic Anti-CD123 CAR T-Cell Resistant to a Drug for its Use in Immunotherapy In particular, the present invention relates to an allogeneic T-cell, in particular an allogeneic ant-CD123 CAR expressing T-cell, and preferably an allogeneic anti-CD123 CAR expressing T-cell comprising a peptide having 80% to 100% identity with scfv from Klon 43, said allogeneic anti-CD123 CAR expressing T-cell comprising a peptide having 80% to 100% identity with scfv from klon 43 is more particularly resistant to a drug, and specifically suitable for immunotherapy.

In a preferred embodiment, said allogeneic anti-CD123 CAR expressing T-cell comprises a peptide having 80% to 100% identity with SEQ ID NO. 44 and is is more particularly resistant to a drug, and specifically suitable for Immunotherapy.

The resistance of a drug can be conferred by inactivation of drug sensitizing genes or by expression of drug resistance genes. Some examples of drugs which suit to the invention are the purine nucleoside analogues (PNAs) such as clofarabine or fludarabine, or other drugs such as 6-Mercaptopurine (6MP) and 6 thio-guanine (6TG).

In one aspect, the present invention provides methods for engineering immune cells to make them resistant to purine nucleotide analogs (PNA), such a clorofarabine or fludarabine, so that they can be used in cancer immunotherapy treatments in patients pre-treated with these conventional chemotherapies.

The resistance to drugs can be conferred to the T-cells by inactivating one or more gene(s) responsible for the cell's sensitivity to the drug (drug sensitizing gene(s)), such as the dcK and/or HPRT genes.

According to another aspect, the resistance to drugs can be conferred to a T-cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell according to the invention.

For instance, CD52 and glucocorticoid receptors (GR), which are drug targets of Campath (alemtuzumab) or rituximab and glucocorticoids treatments, can be inactivated to make the cells resistant to these treatments and give them a competitive advantage over patient's own T-cells not endowed with specific CD123 CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

According to further aspect of the invention, the immune cells can be further manipulated to make them more active or limit exhaustion, by inactivating genes encoding proteins that act as "immune checkpoints" that act as regulators of T-cells activation, such as the following gene selected from CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF1OB, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10A, IL10RB, HMOX2, IL6R, IL6ST, CSK, PAG1, SITI, FOXP3, PRDM1 (orblimpl), BATF, GUCYIA2, GUCY1A3, GUCY1B2, GUCY1B3, preferably, said gene is PDCD1 or CTLA-4. Examples of genes, which expression could be reduced or suppressed are indicated in Table 9.

In one embodiment said gene is a gene that acts as a regulator of T-cells activation coding the beta 2 microglobulin protein.

According to a further aspect of the invention, the anti-CD123 CAR-immune cells of the invention can be further manipulated to make them resistant to a drug, in particular to a drug used during chemotherapy against cancer, in particular a CD123-expressing cell-mediated cancer such as AML. This can be achieved by introducing a gene conferring resistance to said drug. This same gene may be turned on and off by using a gene inducible inhibition/expression system as previously described (Garcia E L, Mills A A (2002) Getting around lethality with inducible Cre-mediated excision. Semin Cell Dev Biol 13:151-8, lewandoski M (2001) Conditional control of gene expression in the mouse. Nat Rev Genet 2:743-55; Scharfenberger L, Hennerici T, Kirly G et al. (2014) Transgenic mouse technology in skin biology: Generation of complete or tissue-specific knockout mice. J invest Dermatol 134:e16; Schwenk F, Kuhn R, Angrand PO et a/. (1998) Temporally and spatially regulated somatic mutagenesis in mice. Nucleic Acids Res 26:1427-32

Thus, anti-CD123 CAR-expressing, drug resistant immune cell, wherein (i) at least one gene expressing one or more component of T-cell receptor (TCR) is inactivated (ii) at least one gene conferring resistance to a drug is incorporated or a gene conferring sensitivity to said drug is deleted or mutated to be inactivated (iii) optionally another gene selected from the gene disclosed in table 9 is inactivated—is an object of the present invention.

The present invention encompasses the isolated anti-CD123 CAR-immune cells or cell lines obtainable by the method of the invention, more particularly isolated cells comprising any of the proteins, polypeptides, allelic variants, altered or deleted genes or vectors described herein.

The immune cells of the present invention or cell lines can further comprise exogenous recombinant polynucleotides, in particular CARs or suicide genes or they can comprise altered or deleted genes coding for checkpoint proteins or ligands thereof that contribute to their efficiency as a therapeutic product, ideally as an "off the shelf" product. In another aspect, the present invention concerns the method for treating or preventing cancer in the patient by administrating at least once an engineered immune cell obtainable by the above methods.

TABLE 9

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

TABLE 10

Sequence of the different humanized antibody fragments

| Functional domains | SEQ ID # | Raw amino acid sequence |
|---|---|---|
| Humanized scFv Klon43 Variant VL1 | SEQ ID NO. 54 | MADYKDIVMTQSPSSVSASVGDRVTITCRASQNV DSAVAWYQQKPGKAPKALIYSASYRYSGVPSRFS GRG5GTDFTLTISSLQPEDFATYYCQQYY5TPWTF GQGTKVEIKR |
| Humanized scFv Klon43 Variant VL2 | SEQ ID NO. 55 | MADYKDIQMTQSPSSVSASVGDRVTITCRASQN VDSAVAWYQQKPGKAPKALIYSASYRYSGVPSRF SGRGSGTDFTLTISSLQPEDFATYYCQQYYSTPWT FGQGTKVEIKR |

TABLE 10-continued

Sequence of the different humanized antibody fragments

| Functional domains | SEQ ID # | Raw amino acid sequence |
|---|---|---|
| Humanized scFv Klon43 Variant VL3 | SEQ ID NO. 56 | MADYKDIQMTQSPSSVSASVGDRVTITCRASQN VDSAVAWYQQKPGKAPKALIYSASYRYSGVPSRF SGSGSGTDFTLTISSLQPEDFATYYCQQYYSTPWT FGQGTKVEIKR |
| Humanized scFv Klon43 Variant VL4 | SEQ ID NO. 57 | MADYKDIQMTQSPSSVSASVGDRVTITCRASQN VDSAVAWYQQKPGKAPKLLIYSASYRYSGVPSRFS GSGSGTDFTLTISSLQPEDFATYYCQQYYSTPWTF GQGTKVEIKR |
| Humanized scFv Klon43 Variant VL5 | SEQ ID NO. 58 | MADYKDIQMTQSPSSVSASVGDRVTITCRASQN VDSAVAWYQQKPGKAPKLLIYSASYRQSGVPSRF SGSGSGTDFTLTISSLQPEDFATYYCQQYYSTPWT FGQGTKVEIKR |
| Humanized scFv Klon43 Variant VL6 | SEQ ID NO. 59 | MADYKDIQMTQSPSSVSASVGDRVTITCRASQN VDSAVAWYQQKPGKAPKLLIYSASYGQSGVPSRF SGSGSGTDFTLTISSLQPEDFATYYCQQYYSTPWT FGQGTKVEIKR |
| Humanized scFv Klon43 Variant VH1 | SEQ ID NO. 60 | EVKLVESGGGLVQPGRSLRLSCTASGFTFTDY YMSWVRQAPGKGLEWVGLIRSKADGYTTEYSAS VKGRFTISRDDSKSILYLQMNSLKTEDTAVYYC ARDAAYYSYYSPEGAMDYWGQGTLVTVSS |
| Humanized scFv Klon43 Variant VH2 | SEQ ID NO. 61 | EVQLVESGGGLVQPGRSLRLSCTASGFTFTDY YMSWVRQAPGKGLEWVGLIRSKADGYTTEYSA SVKGRFTISRDDSKSILYLQMNSLKTEDTAVY YCARDAAYYSYYSPEGAMDYWGQGTLVTVSS |
| Humanized scFv Klon43 Variant VH3 | SEQ ID NO. 62 | EVQLVESGGGLVQPGRSLRLSCTASGFTFTDY YMSWVRQAPGKGLEWVGLIRSKADGYTTEYSAS VKGRFTISRDDSKSIAYLQMNSLKTEDTAVYYCA RDAAYYSYYSPEGAMDYWGQGTLVTVSS |
| Humanized scFv Klon43 Variant VH4 | SEQ ID NO. 63 | EVQLVESGGGLVQPGRSLRLSCTASGFTFTDY YMSWVRQAPGKGLEWVGFIRSKADGYTTEYSAS VKGRFTISRDDSKSIAYLQMNSLKTEDTAVYYCA RDAAYYSYYSPEGAMDYWGQGTLVTVSS |
| Humanized scFv Klon43 Variant VH5 | SEQ ID NO. 64 | EVQLVESGGGLVQPGRSLRLSCTASGFTFTDY YMSWVRQAPGKGLEWVGFIRSKADGYTTEYAAS VKGRFTISRDDSKSIAYLQMNSLKTEDTAVYYCA RDAAYYSYYSPEGAMDYWGQGTLVTVSS |
| Humanized scFv Klon43 Variant VH6 | SEQ ID NO. 65 | EVQLVESGGGLVQPGRSLRLSCTASGFTFTDY YMSWVRQAPGKGLEWVGLIRSKADGYTTEYAA SVKGRFTISRDDSKSIAYLQMNSLKTEDTAVYY CARDAAYYSYYSPEGAMDYWGQGTLVTVSS |
| Humanized scFv Klon43 Variant VH7 | SEQ ID NO. 66 | EVQLVESGGGLVQPGRSLRLSCTASGFTFTDYYM SWVRQAPGKGLEWVGFIRSKADGYTTEYAASVK GRFTISRDDSKSIAYLQMNSLKTEDTAVYYCTRDA AYYSYYSPEGAMDYWGQGTLVTVSS |

In a preferred embodiment said method of further engineer the immune cells involves introducing into said T cells polynucleotides, in particular mRNAs, encoding specific rare-cutting endonuclease to selectively inactivate the genes mentioned above by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Delivery Methods

The different methods described above involve expressing a protein of interest such as drug resistance gene, rare-cutting endonuclease, Chimeric Antigen Receptor (CAR), in particular an anti-CD123 CAR and more particularly, a CAR comprising a SEQ ID NO. 1+ SEQ ID NO. 44, and a suicide gene into a cell, As non-limiting example, said protein of interest can be expressed in the cell by its introduction as a transgene preferably encoded by at least one plasmid vector. Polypeptides may be expressed in the cell as a result of the introduction of polynucleotides encoding said polypeptides into the cell. Alternatively, said polypeptides could be produced outside the cell and then introduced thereto.

Methods for introducing a polynucleotide construct into cells are known in the art and include as non limiting examples stable transformation methods wherein the polynucleotide construct is integrated into the genome of the cell, transient transformation methods wherein the polynucleotide construct is not integrated into the genome of the cell and virus mediated methods.

Said polynucleotides may be introduced into a cell by for example, recombinant viral vectors (e.g. retroviruses, adenoviruses), liposome and the like. For example, transient transformation methods include for example microinjection, electroporation or particle bombardment, cell fusion. Said polynucleotides may be included in vectors, more particularly plasmids or virus, in view of being expressed in cells. Said plasmid vector can comprise a selection marker which provides for identification and/or selection of cells which received said vector.

Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al, J of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)).

By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

In a more preferred embodiment of the invention, polynucleotides encoding polypeptides according to the present invention can be mRNA which is Introduced directly into the cells, for example by electroporation. The inventors determined the optimal condition for mRNA electroporation in T-cell. The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, MA 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow moving the polynucleotide into the cell.

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified Immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptive immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with a CD123 CAR as described above, that do not express functional TCR and that a reactive towards CD123 positive cells, for their allogeneic transplantation into patients.

As a more preferred embodiment, the present invention provides T-cells or a population of T-cells endowed with a CD123 CAR and that a reactive towards CD123 positive cells as described above, that do not express a functional TCR and are resistant to a selected drug, for their allogeneic transplantation into patients treated with said selected drug.

in an even more preferred embodiment, the present invention provides T-cells or a population of T-cells endowed with an anti-CD123 CAR comprising a polypeptide of SEQ ID NO. 1+ SEQ ID NO. 44, even more preferably an anti-CD123 CAR comprising 80%, 81%, 82%, 83%, 84%, 85%, 86%, 87%, 88%, 89%, 90%, 91%, 92%, 93%, 94%, 95%, 96%, 97%, 98%,or 99% identity with SEQ ID NO. 1+ SEQ ID NO. 44, in particular an anti CD123-CAR comprising 85% to 99% identity with SEQ ID NO. 1+ SEQ ID NO. 44.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-ceil.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, −10, -2, 1L-15, TGFp, and TNF-or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPM11640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament.

In another embodiment, said medicament can be used for treating cancer, particularly for the treatment of B-cell lymphomas and leukemia in a patient in need thereof.

In another embodiment, said isolated cell according to the invention or cell line derived from said isolated cell can be used in the manufacture of a medicament for treatment of a cancer in a patient in need thereof.

In a particular embodiment, an anti-CD123 CAR expressing T cell is provided as a medicament for the treatment of AML, of an AML subtype, of an AML-related complication, of an AML-related condition. In a preferred embodiment, an anti-CD123 CAR expressing T cell wherein said anti-CD123 CAR comprises SEQ ID NO 44 is provided as a medicament.

In another embodiment, said medicament can be used for treating a CD123-expressing cell-mediated pathological condition or a condition characterized by the direct or indirect activity of a CD123-expressing cell. In other words, the invention is related to an anti-CD123 CAR expressing T cell comprising 80% to 100% of SEQ ID NO 44 for its use as a medicament to treat a condition linked to the detrimental activity of CD123-expressing cells, in particular to treat a condition selected from AML, AML subtype, AML-related complication, and AML-related conditions;

In another aspect, the present invention relies on methods for treating patients in need thereof, said method comprising at least one of the following steps:
(a) providing an immune-cell obtainable by any one of the methods previously described;
(b)Administrating said transformed immune cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed wherein a pre-malignant or malignant cancer condition characterized by CD123-expressing cells, especially by an overabundance of CD123-expressing cells. Such conditions are found in hematologic cancers, such as leukemia or malignant lymphoproliferative disorders. Lymphoproliferative disorder can be lymphoma, in particular multiple myeloma, non-Hodgkin's lymphoma, Burkitt's lymphoma, and follicular lymphoma (small cell and large cell), Cancers that may be treated may comprise nonsolid tumors (such as hematological tumors, including but not limited to pre-B ALL (pediatric indication), adult ALL, mantle cell lymphoma, diffuse large B-cell lymphoma and the like. Types of cancers to be treated with the CARs of the invention include, but are not limited leukemia or lymphoid malignancies. Adult tumors/cancers and pediatric tumors/cancers are also included.

In one embodiment, the present invention provides a composition for its use in the treatment of a CD123 expressing cells-mediated disease, in particular a CD123 expressing cells-mediated hematologic cancer, said composition comprising said anti-CD123 CAR expressing T cell of the invention, preferably said anti-CD123 CAR is of SEQ ID NO. 44 or of SEQ ID NO. 1+ SEQ ID NO. 44.

Any other CD123-mediating or CD123-involving malignant lymphoproliferative disorders disclosed herein may be improved with the anti-CD123 CAR-expressing cells of the present invention.

In a preferred embodiment, the cancer that may be treated using the anti-CD123 CAR-expressing cells of the present invention is leukemia, a disease associated to leukemia or a complication thereof, Leukemias that can be treated using the anti-CD123 CAR-expressing cells of the present invention can be acute myelogenous leukemia (AML), chronic myelogenous leukemia, myelodysplastic syndrome, acute lymphoid leukemia, chronic lymphoid leukemia, and myelodysplastic syndrome.

AML or AML subtypes that may be treated using the anti-CD123 CAR-expressing cells of the present invention may be in particular, acute myeloblastic leukemia, minimally differentiated acute myeloblastic leukemia, acute myeloblastic leukemia without maturation, acute myeloblastic leukemia with granulocytic maturation, promyeiocytic or acute promyelocytic leukemia (APL), acute myelomonocytic leukemia, myelomonocytic together with bone marrow eosinophilia, acute monoblastic leukemia (MSa) or acute monocytic leukemia (M5b), acute erythroid leukemias, including erythroleukemia (M6a) and very rare pure erythroid leukemia (M6b), acute megakaryoblastic leukemia, acute basophilic leukemia, acute panmyelosis with myelofibrosis, whether involving CD123-positive cells.

Subtypes of AML also include, hairy cell leukemia, philadelphia chromosome-positive acute lymphoblastic leukemia.

AML may be classified as AML with specific genetic abnormalities. Classification is based on the ability of karyotype to predict response to induction therapy, relapse risk, survival.

Accordingly, AML that may be treated using the anti-CD123 CAR-expressing cells of the present invention may be AML with a translocation between chromosomes 8 and 21, AML with a translocation or inversion in chromosome 16, AML with a translocation between chromosomes 9 and 11, APL (M3) with a translocation between chromosomes 15 and 17, AML with a translocation between chromosomes 6 and 9, AML with a translocation or inversion in chromosome 3, AML (megakaryoblastic) with a translocation between chromosomes1 and 22, The present invention is particularly useful for the treatment of AML associated with these particular cytogenetic markers.

The present invention also provides an anti-CD123 CAR expressing T cell for the treatment of patients with specific cytogenetic subsets of AML, such as patients with t(15;17) (q22;q21) identified using all-trons retinoic acid (ATRA)16-19 and for the treatment of patients with t(8;21)(q22;q22) or inv(16)(p13422)/t(16;16)(p13;q22) identified using repetitive doses of high-dose cytarabine.

Preferably, the present invention provides an anti-CD123 CAR expressing T cell for the treatment of patients with aberrations, such as −5/del(5q), −7, abnormalities of 3q, or a complex karyotype, who have been shown to have inferior complete remission rates and survival.

Group of Patients

In a preferred embodiment, the invention provides a treatment for AML in patients over 60 years or in patients of less than 20 years.

In a more preferred embodiment, the present invention provides a pediatric treatment, in particular a pediatric treatment against AML, or AML-related diseases or complications.

In still another preferred embodiment, the present invention is used as a treatment in AML patients with low, poor or unfavorable status that is to say with a predicted survival of less than 5 years survival rate. In this group, patients suffering AML with the following cytogenetic characteristics: −5; 5q; −7; 7q-;11q23; non t(9;11); inv(3); t(3;3); t(6;9); t(9;22) is associated with poor-risk status (Byrd J. C. et aL, Dec. 15, 2002; Blood: 100 (13) and is especially contemplated to be treated according to the present invention or with an object of the present invention.

In one embodiment, the anti-CD123 CAR expressing T cell of present invention may be used as induction therapy, as post remission therapy of AML or as a consolidation therapy in patient with AML. Preferably, cells expressing at least one anti-CD123 CAR of SEQ ID NO. 1+ SEQ ID NO., 44 are used as post remission therapy of AML or as a consolidation therapy in patient with AML.

In one embodiment, the anti-CD123 CAR expressing T cell of the present invention may be used in case of AML relapse, or in case of refractory or resistant AML. Preferably, cells comprising at least one anti-CD123 CAR of SEQ ID NO. 1+ SEQ ID NO. 44 of the invention are used in patients with AML relapse, or with refractory or resistant AML, more preferably, in combination with at least one other anti-cancer drug In another preferred embodiment, at least one anti-CD123 CAR of SEQ ID NO. 1+ SEQ ID NO. 44 expressing cell is used for preventing cancer cells development occurring in particular after anti-cancer treatment, during bone marrow depletion or before bone marrow transplantation, after bone marrow destruction.

AML Complications

In one particular embodiment the invention provides a medicament that improves the health condition of a patient, in particular a patient undergoing a complication related to AML. More preferably, said engineered anti-CD123 CAR expressing T cell of the invention is expressing at least one anti-CD123 CAR of SEQ ID NO. 1+ SEQ ID NO. 44 and is used as a medicament for the treatment of a complication related to AML.

A complication or disease related to AML may Include a preceding myelodysplasia phase, secondary leukemia, in particular secondary AML, high white blood cell count, and absence of Auer rods. Among others, leukostasis and involvement of the central nervous system (CNS), Hyperleukocytosis, residual disease. are also considered as a complication or disease related to AML.

AML Associated Diseases

In one embodiment, the present invention also provides an anti-CD123 CAR expressing T cell for the treatment of a pathological condition related to AML. Preferably, the present invention provides a cell expressing at least one anti-CD123 CAR of SEQ ID NO. 1+ SEQ ID NO. 44 for the treatment of a pathological condition related to AML The present invention provides a therapy for AML related myeloid neoplasms, for acute myelold leukemia and myelodysplastic syndrome, a treatment of relapsed or refractory acute myeloid leukemia, a treatment of relapsed or refractory acute promyelocytic leukemia in adults, a treatment for acute promyeloid leukaemia, a treatment of acute myeloid leukemia in adults over 60 years.

According to another aspect, the present invention provides a composition for the treatment of AML associated diseases, in particular hematologic malignancy related to AML.

Hematologic malignancy related to AML conditions include myelodysplasia syndromes (MDS, formerly known as "preleukemia") which are a diverse collection of hematological conditions united by ineffective production (or dysplasia) of myeloid blood cells and risk of transformation to AM In another embodiment, the invention provides a medicament that improves the health state of a patient suffering multiple myeloma.

Other pathological conditions or genetic syndromes associated with the risk of AML can be improved with the adequate use of the present invention, said genetic syndromes include Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome) Other CD123-mediated pathological conditions According to another aspect, the present invention provides a composition for the treatment of CD123+ cell-mediated diseases. These CD123+ cell mediated diseases include inflammation, autoimmune diseases.

In particular, the present invention can be used for the treatment of CD123+ cell mediated diseases such as inflammation of the gastrointestinal mucosae and more particularly, inflammatory bowel diseases, nasal allergy, inflammation of the skin such as juvenile dermatomyositis, hematodermia.

The present invention can be used as a medicament for the treatment of CD123+ cell mediated diseases such as autoimmune diseases in particular Kikushi disease.

Preferably, the present invention provides a treatment for a recurrent infection including infection due to viruses such as Epstein-Barr virus, herpes simplex virus, in particular oncogenic viruses, HHV-8, HHV-6, HTLV or HIV, parasitic infection such as infection due to *Plasmodium falciparum, Plasmodium vivax, Plasmodium ovale,* or *Plasmodium malariae.*

In particular, the present invention provides a treatment for Epstein-Barr virus lymphadenitis, herpes simplex virus lymphadenitis.

In another aspect, the present invention provides a composition for the treatment of systemic lupus erythematosus lymphadenitis, tuberculosis, cystic fibrosis, hepatitis, billary atresia, in particular virus-induced hepatitis or biliary atresia in children, autoimmune hepatitis; primary biliary cirrhosis.

Composition comprising an engineered T cells according to the invention for use as a medicament and method The present invention also provides a composition for its use or a method for treating a disease. In one aspect, the disease is a hematologic cancer, in particular a stem cell cancer including but is not limited to leukemia (such as acute myelogenous leukemia (AML), chronic myelogenous leukemia, acute lymphoid leukemia, chronic lymphoid leukemia and myelodysplasia syndrome) and malignant lymphoproliferative conditions, including lymphoma (such as multiple myeloma, non-Hodgkin's lymphoma, Burkitt's lymphoma, and small cell- and large cell-follicular lymphoma), or a complication thereof.

The present invention also provides a composition for its use or a method for inhibiting the proliferation or reducing a CD123-expressing cell population or activity in a patient. An exemplary method includes contacting a population of cells comprising a CD123-expressing cell with a CD 123 CART cell of the invention that binds to the CD123-expressing cell.

In a more specific aspect, the present invention provides a composition for its use or a method for inhibiting the proliferation or reducing the population of cancer cells expressing CD 123 in a patient, the methods comprising contacting the CD123-expressing cancer cell population with a CD 123 CART cell of the invention that binds to the CD123-expressing cell, binding of a CD 123 CART cell of the invention to the CD123-expressing cancer cell resulting in the destruction of the CD123-expressing cancer cells In certain aspects, the CD 123 CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% (to undetectable level) in a subject with or animal model for myeloid leukemia or another cancer associated with CD123-expressing cells, relative to a negative control.

The present invention also provides a composition for its use or a method for preventing, treating and/or managing a disorder or condition associated with CD123-expressing cells (e.g., associated with a hematologic cancer), the methods comprising administering to a subject in need a CD 123 CART cell of the invention that binds to the CD123-expressing cell, in one aspect, the subject is a human. Non-limiting examples of disorders associated with CD123-expressing cells include autoimmune disorders (such as lupus), inflammatory disorders (such as allergies, IBD, and asthma) and cancers (such as hematological cancers, in particular AML or AML complications).

The present invention also provides a composition for its use or a method for preventing, treating and/or managing a disease associated with CD123-expressing cells, the method comprising administering to a subject in need a CD 123 CART cell of the invention that binds to the CD123-expressing cell. In one aspect, the subject is a human. Non-limiting examples of diseases associated with CD123-expressing cells include Acute Myeloid leukemia (AML), myelodysplasia, B-cell Acute Lymphoid Leukemia, T-cell Acute Lymphoid Leukemia, hairy cell leukemia, blastic plasmacytoid dendritic cell neoplasm, chronic myeloid leukemia, hodgkin lymphoma.

The present invention provides a composition for Its use or a method for treating or preventing relapse of cancer associated with CD123-expressing cells, the method comprising administering to a subject in need thereof a CD 123 CART cell of the invention that binds to the CD 123-expressing cell. In another aspect, the methods comprise administering to the subject in need thereof an effective amount of a CD 123 CART cell of the invention that binds to the CD123-expressing cell in combination with an effective amount of another therapy.

In one aspect, CD 123 is considered to be a "cancer stem cell" marker in AML. Therefore, a CD 123 CART cell of the invention can prevent relapse of AML, or even treat AML that is mostly CD 123-negative but with a "stem" population of CD 123+ cells (a CD123-expressing cells).

In one aspect, the invention provides compositions and methods for treating subjects that have undergone treatment for a disease or disorder associated with elevated expression levels of CD 19, and exhibits a disease or disorder associated with elevated levels of CD123.

In one aspect, B-cell acute lymphoid leukemia (ALL) is an example of disease requiring a serial treatment using CART cells. For example, treatment with anti-CD 19 CAR T cells can sometimes result in CD19-negative relapse, which can be treated with anti-CD123 CAR T cells of the invention. Alternatively, the present invention includes dual targeting of B-ALL using CART cells comprising an anti-CD 19 CAR and an anti-CD 123 CAR.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

Preferably, the treatment with the engineered immune cells according to the invention may be administered in combination (e.g., before, simultaneously or following) with one or more therapies against cancer selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, combination of arsenic trioxyde, transretinoic acid, mechlorethamine, procarbazine, chlorambucil, and combination thereof.

According to a preferred embodiment of the invention, said treatment can be administrated into patients undergoing an immunosuppressive treatment. indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 10-10W cells per kg body weight, preferably 10" to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments of the present invention, anti-CD123 CAR expressing cells are administered to a patient in conjunction (e.g., before, simultaneously or following) with a drug selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, mechlorethamine, procarbazine, chlorambucil, and combination thereof. In these embodiments anti-CD123 CAR expressing cells may be resistant to the particular drug or combination of drugs that is (are) administered in conjunction with anti-CD123 CAR expressing cells.

In other embodiments of the present invention, anti-CD123 CAR expressing cells are administered to a patient in conjunction with a drug selected from cytarabine, anthracyclines, 6-thioguanine, hydroxyurea, prednisone, and combination thereof. Other

Definitions

Unless otherwise specified, "a," "an," "the," and "at least one" are used interchangeably and mean one or more than one.-Amino acid residues in a polypeptide sequence are designated herein according to the one-letter code, in which, for example, Q means Gin or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: an is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n representing g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFv Fc) fused to the intracellular signaling domain of the T cell antigen receptor complex zeta chain (scFv Fc:z) and have the ability, when expressed in T cells, to redirect antigen recognition based on the monoclonal antibody's specificity. One example of CAR used in the present invention is a CAR directing against CD123 antigen and can comprise as non limiting example the amino acid sequences: SEQ ID NO: 23 to 48.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as Foki (Porteus and Carroll 2005), a Cas9 endonuclease from CRISPR system (Gasiunas, Barrangou et al. 2012; Jinek, Chylinski et al. 2012; Cong, Ran et al. 2013; *Mali*, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-1. In a particular embodiment, the TALE domain can be fused to a meganuclease like for instance I-CreI and I-OnuI or functional variant thereof. in a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Engineered TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; *Mali*, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif-PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an1-CreI variant.

By "delivery vector" or "delivery vectors" is intended any delivery vector which can be used in the present invention to put into cell contact (i.e "contacting") or deliver inside cells or subcellular compartments (i.e "introducing") agents/ chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene is delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; urkat cells; HepG2 cells; HeLa cells; HT-1080 cells; HCT-116 cells; Hu-h7 cells; Huvec cells; Molt 4 cells., All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

- by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.
- by "variant(s)", it is intended a repeat variant, a variant, a DNA binding variant, a TALE-nuclease variant, a polypeptide variant obtained by mutation or replacement of at least one residue in the amino acid sequence of the parent molecule.
- by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means. For example, a functional variant of pTalpha can have 70%, 75%, 80%, 85%, 87.5%, 90%, 92.5%, 95%, 97.5%, 98%, 99% sequence similarity to the amino acid sequence of SEQ ID NO: 107. A polynucleotide encoding such a functional variant would be produced by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, 87-1 (CD80), 87-2 (CD86), PD-L1, PD-12, 4-1181, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, 87-H3, a ligand that specifically binds with CD83.

A "co-stimulatory molecule" refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo-or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The term "relapsed" refers to a situation where a subject or a mammal, who has had a remission of cancer after therapy has a return of cancer cells.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic (or primary resistance), which means the disease has never been responsive to the drug or drugs, or it can be acquired, which means the disease ceases responding to a drug or drugs that the disease had previously responded to (secondary resistance). In certain embodiments, drug resistance is intrinsic, In certain embodiments, the drug resistance is acquired.

The term "hematologic malignancy" or "hematologic cancer" refers to a cancer of the body's blood-bone marrow and/or lymphatic tissue. Examples of hematological malignancies include, for instance, myelodysplasia, leukemia, lymphomas, such as cutaneous Lymphomas. non-Hodgkin's lymphoma, Hodgkin's disease (also called Hodgkin's lymphoma), and myeloma, such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM).

The term "leukemia" refers to malignant neoplasms of the blood-forming tissues, including, but not limited to, chronic lymphocytic leukemia or chronic lymphoid leukemia, chronic myelocytic leukemia, or chronic myelogenous leukemia, acute lymphoblastic leukemia, acute myeloid leukemia or acute myelogenous leukemia (AML) and acute myeloblastic leukemia.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

General Method

Primary T-Cell Cultures

T cells were purified from Buffy coat samples provided by EFS (Etablbssement Frangais du Sang, Paris, France) using Ficoll gradient density medium. The PBMC layer was recovered and T cells were purified using a commercially available T-cell enrichment kit. Purified T cells were activated in X-Vivo™-15 medium (Lonza) supplemented with 20 ng/mL Human IL-2, 5% Human, and Dynabeads Human T activator CD3/CD28 at a bead:cell ratio 1:1 (Life Technologies).

CAR mRNA Transfection

Transfections were done at Day 4 or Day 11 after T-cell purification and activation. 5 millions of cells were transfected with 15 μg of mRNA encoding the different CAR constructs. CAR mRNAs were produced using T7 mRNA polymerase transfections done using Cytopulse technology, by applying two 0.1 mS pulses at 3000V/cm followed by four 0.2 mS pulses at 325V/cm in 0.4 cm gap cuvettes in a final volume of 200 μl of "Cytoporation buffer T" (BTX Harvard Apparatus). Cells were Immediately diluted in X-Vivo™-15 media and incubated at 37'C with 5% $CO_2$. IL-2 was added 2h after electroporation at 20 ng/mL Dearanulation Assay (CD107a Mobilization)

T-cells were Incubated in 96-well plates (40,000 cells/well), together with an equal amount of cells expressing various levels of the CD123 protein. Co-cultures were maintained in a final volume of 100 μl of X-Vivo™-15 medium (Lonza) for 6 hours at 37° C. with 5% $CO_2$.

CD107a staining was done during cell stimulation, by the addition of a fluorescent anti-CD107a antibody at the beginning of the co-culture, together with 1 μg/ml of anti-CD49d, 1 μg/ml of anti-CD28, and 1x Monensin solution. After the 6h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24h after mRNA transfection.

IFN Gamma Release Assay

T-cells were incubated in 96-well plates (40,000 cells/well), together with cell lines expressing various levels of the CD123 protein. Co-cultures were maintained in a final volume of 100 μl of X-Vivo −15 medium (Lonza) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay. The IFN gamma release assays were carried by starting the cell co-cultures 24h after mRNA transfection.

Cytotoxicity Assay

T-cells were incubated in 96-well plates (100,000 cells/well), together with 10,000 target cells (expressing CD123) and 10,000 control (CD123neg) cells in the same well. Target and control cells were labelled with fluorescent intracellular dyes (CFSE or Cell Trace Violet) before co-culturing them with CAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or CD123neg control cells)

was determined and the % of specific cell lysis was calculated. Cytotoxicity assays were carried out 48h after mRNA transfection.

T-Cell Transduction

Transduction of T-cells with recombinant lentiviral vectors expression the CAR was carried out three days after T-cell purification/activation. CAR detection at the surface of T-cells was done using a recombinant protein consisting on the the fusion of the extracellular domain of the human CD123 protein, together with a murine IgG1 Fc fragment. Binding of this protein to the CAR molecule was detected with a fluorochrome-conjugated secondary antibody targeting the mouse Fc portion of the protein, and analyzed by flow cytometry.

Anti-Tumor Mouse Model

Immunodeficient NOG mice were intravenously (iv) injected with (CD123 expressing_MOLM13-Luciferase cells as an AML xenograft mouse model. Optionally, mice received an anti-cancer treatment. Mice were then iv injected (either 2 or 7 days after injection of the tumor cell line) with different doses of CAR+ T-cells to be tested, or with T-cells that were not transduced with the CAR lentiviral vector. Bioluminescent signals were determined at the day of T-cell injection (DO), at D7, 14, 21, 28 and 40 after T-cell injection in order to follow tumoral progression on the different animals.

EXAMPLES

Example 1: Proliferation of TCRalpha Inactivated Cells Expressing a CD123-CAR

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10.

TABLE 10

TAL-nucleases targeting TCRalpha gene

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 49) | Repeat TRAC_T01-L (SEQ ID NO: 50) Repeat TRAC_T01-R (SEQ ID NO: 51) | TRAC_T01-L TALEN (SEQ ID NO: 52) TRAC_T01-R TALEN (SEQ ID NO: 53) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with antiCD3/CD28 coated beads were is transfected with each of the 2 mRNAs encoding both half TRAC_T01 TALE-nucleases. 48 hours post-transfection, different groups of T cells from the same donor were respectively transduced with a lentiviral vector encoding one of the CD-123 CAR previously described (SEQ ID NO: 23 to 48). 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the CD-123 CARs, especially when reactivated with anti-CD28, was observed compared to non-transduced cells.

To investigate whether the human T cells expressing the CD123-CAR display activated state, the expression of the activation marker CD2S are analyzed by FACS 7 days post transduction. The purified cells transduced with the lentiviral vector encoding CD-123 CAR assayed for CD25 expression at their surface in order to assess their activation in comparison with the non-transduced cells. Increased CD25 expression is expected both in CD28 reactivation or no reactivation conditions, Example 2

Construction of CD123 CAR Using Various Anti-CD123 Antibody Fragments

Primary T-Cell Cultures

T cells were purified from Buffy coat samples provided by EFS (Etablissement Franeais du Sang, Paris, France) using Ficoll gradient density medium (Ficoll Paque PLUS/GE Healthcare Life Sciences). The PBMC layer was recovered and T cells were purified using a commercially available T-cell enrichment kit (Stem Cell Technologies). Purified T cells were activated in X-Vivo™-15 medium (Lonza) supplemented with 20 ng/mL Human IL-2 (Miltenyi Biotech), 5% Human Serum (Sera Laboratories), and Dynabeads Human T activator CD3/CD28 at a bead:cell ratio 1:1 (Life Technologies). After activation cells were grown and maintained in X-Viv™-15 medium (Lonza) supplemented with 20 ng/mL Human IL-2 (Miltenyi Biotec) and 5% Human Serum (Sera Laboratories)

CAR mRNA Transfection

Transfections were done at Day 4 or Day 11 after T-cell purification and activation. S millions of cells were transfected with 15 µg of mRNA encoding the different CAR constructs. CAR mRNAs were produced using the mMESSAGE mMACHINE T7 Kit (Life Technologies) and purified using RNeasy Mini Spin Columns (Qiagen). Transfections were done using Cytopulse technology, by applying two 0.1 mS pulses at 3000V/cm followed by four 0.2 mS pulses at 325 V/cm in 0.4 cm gap cuvettes in a final volume of 200 µl of "Cytoporation buffer T" (BTX Harvard Apparatus). Cells were immediately diluted in X-Vivo™-15 media (Lonza) and incubated at 37° C. with 5% $CO_2$. IL-2 (from Miltenyi Biotec was added 2h after electroporation at 20 ng/mL.

Degranulation Assay (CD107a Mobilization)

T-cells were incubated in 96-well plates (40,000 cells/well), together with an equal amount of cells expressing or not the CD123 protein. Co-cultures were maintained in a final volume of 100 µl of X-Vivo™-15 medium (Lonza) for 6 hours at 37° C. with 5% $CO_2$. CD107a staining was done during cell stimulation, by the addition of a fluorescent anti-CD107a antibody (APC conjugated, from Miltenyi Biotec) at the beginning of the co-culture, together with 1 µg/ml of anti-CD49d (BD Pharmingen), 1 g/ml of anti-CD28 (Miltenyi Biotec), and 1x Monensin solution (eBioscience). After the 6h incubation period, cells were stained with a fixable viability dye (eFluor 780, from eBioscience) and fluorochrome-conjugated anti-CD8 (PE conjugated Miltenyi Biotec) and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24h after mRNA transfection.

IFN Gamma Release Assay

T-cells were incubated in 96-well plates (40,000 cells/well), together with cell lines expressing or not the CD123 protein. Co-cultures were maintained in a final volume of 100 μl of X-Vivo™-15 medium (Lonza) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay (Human IFN-gamma Quantikine ELISA Kit, from R&D Systems). The IFN gamma release assays were carried by starting the cell co-cultures 24h after mRNA transfection.

Cytotoxicity Assay

T-cells were incubated in 96-well plates (100,000 cells/well), together with 10,000 target cells (expressing CD123) and 10,000 control (CD123neg) cells in the same well. Target and control cells were labelled with fluorescent intracellular dyes (CFSE or Cell Trace Violet, from Life Technologies) before co-culturing them with CAR+ T-cells. The co-cultures were incubated for 4 hours at 37° C. with 5% $CO_2$. After this incubation period, cells were labelled with a fixable viability dye (eFluor 780, from eBioscience) and analyzed by flow cytometry. Viability of each cellular population (target cells or CD123neg control cells) was determined and the % of specific cell lysis was calculated. Cytotoxicity assays were carried out 48h after mRNA transfection.

Results 6 different scFvs from 7G3, 32716, Klon 43 12F1, 26292, and 0d4 were used to generate Chimeric Antigen Receptors (CARs) and to screen them for their degranulation activity towards CD123+ cells.

Figure 3:
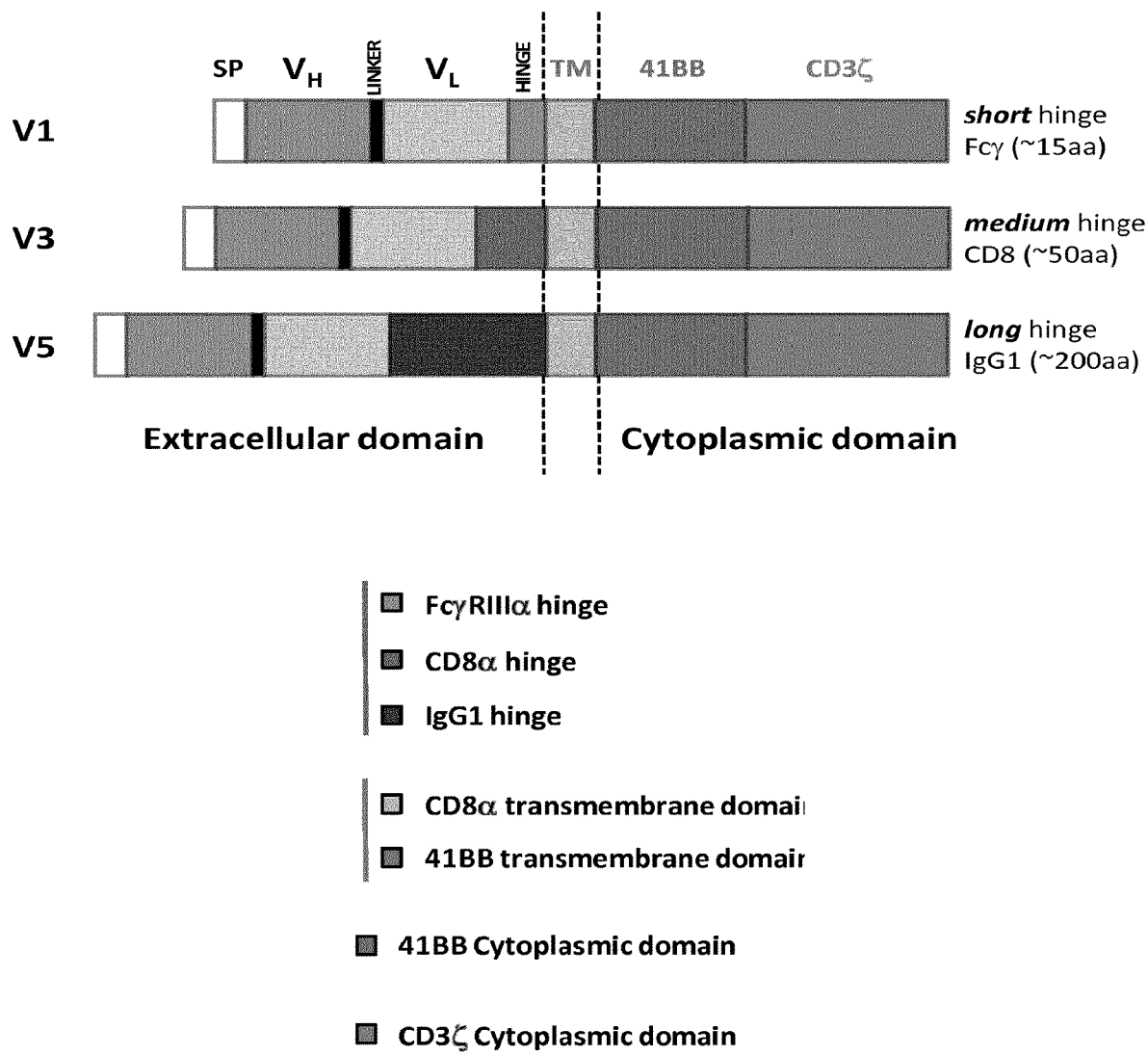
FIG. 3: shows the different architectures for the CAR according to the invention, each of which differs in the hinge region used.
Figure 6:
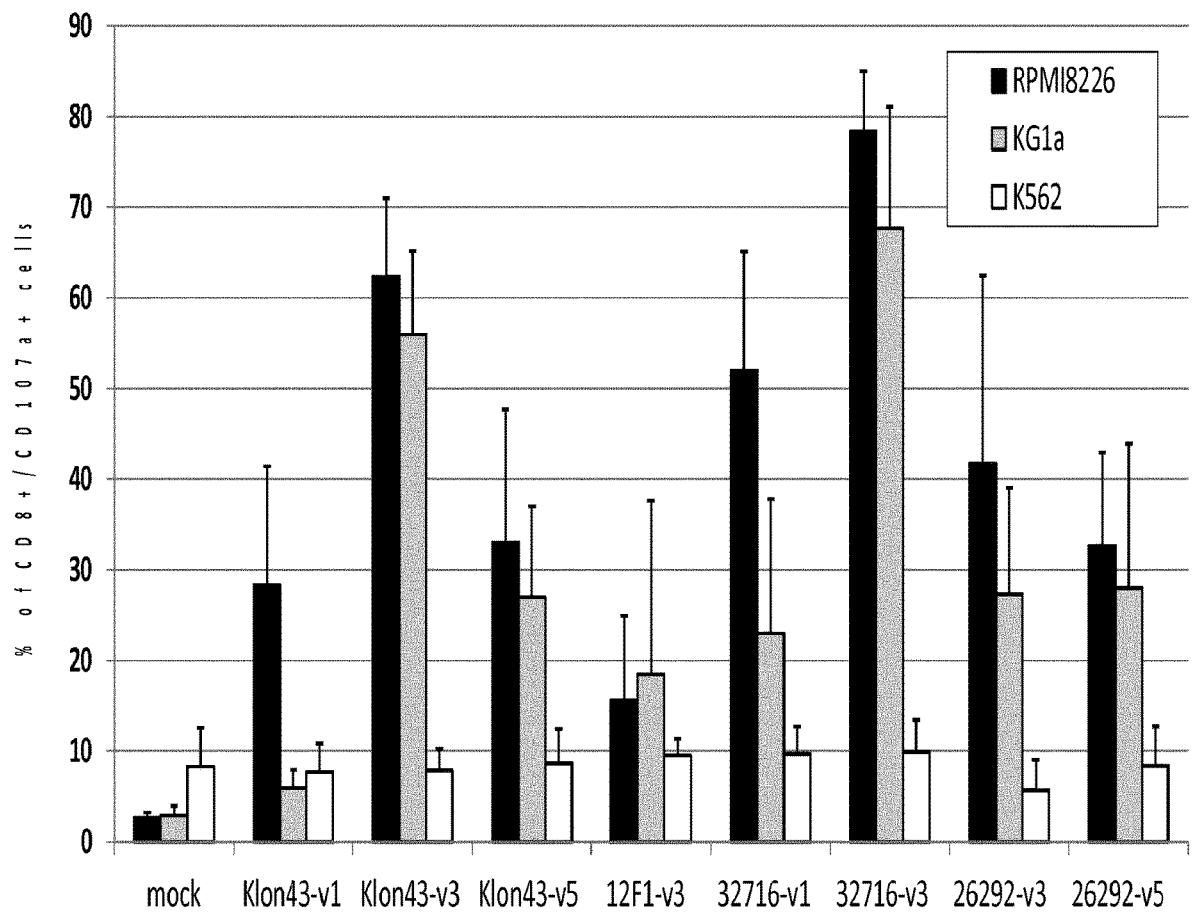
FIG. 6: shows the percentage (%) of degranulation, of various anti-CD123 CAR T cells when co-cultured for 6h with cells expressing different levels of CD123 (KG1a or RPM18226), or with cells that do not express CD123 (K562).
Figure 7:
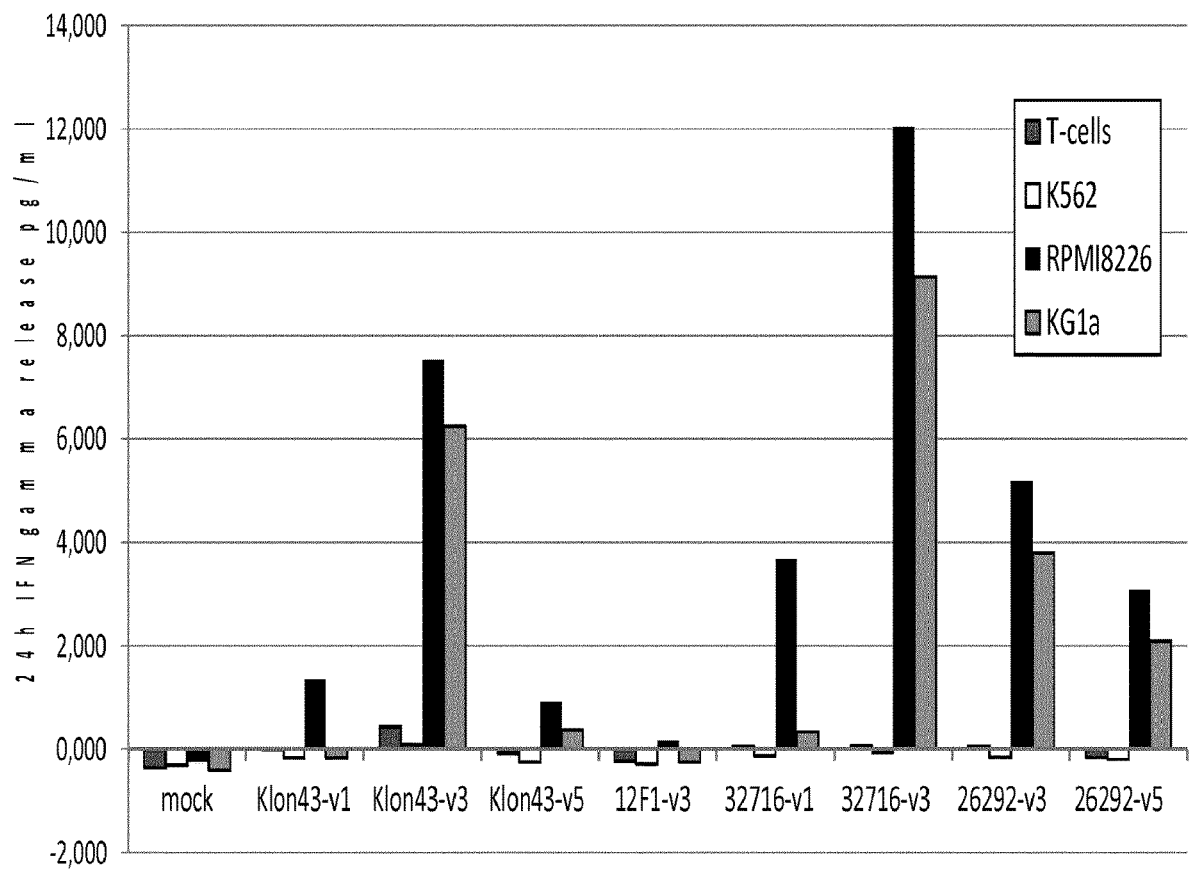
FIG. 7: shows the amount of IFN gamma (IFN$\gamma$) released by various anti-CD123 CAR T cells when co-cultured for 24h with cells expressing different levels of CD123 (KG1a or RPM18226), or with cells that do not express CD123 (K562).
Figure 8:
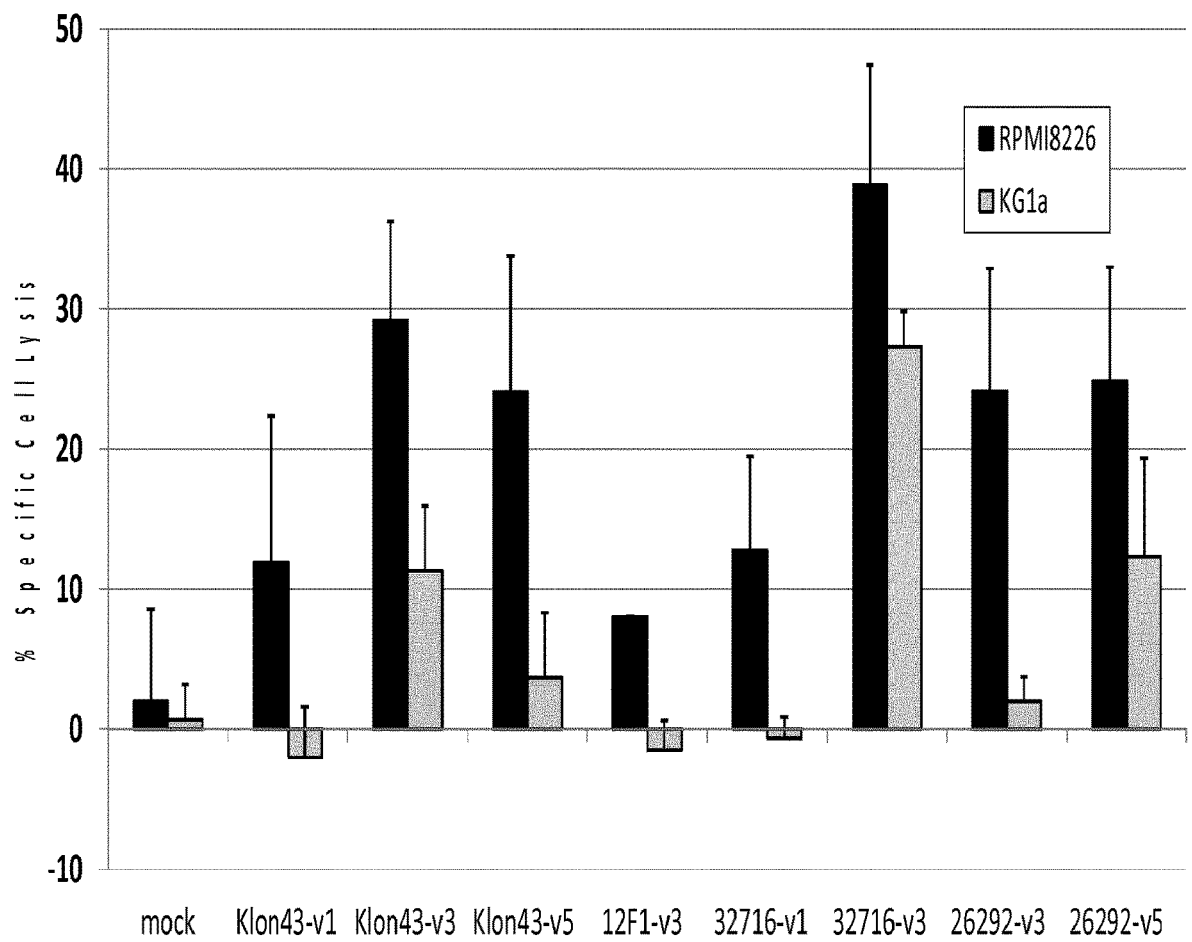
FIG. 8: shows the specific cytolytic activity of various anti-CD123 CAR T cells. Assays were done 48h after CAR mRNA transfection. T-cells were co-cultured with K562+ KG1a or K5624RPM18226 cells. Cellular viability for each of the cell lines was determined at the end of the co-cultured and a specific cell lysis percentage was calculated.

Different architectures were designed (FIG. 2 and FIG. 3) and their activity was determined upon transient expression in human T-cells (Figure S, FIG. 6, FIG. 7 and FIG. 8).

T-cells were purified from buffy-coat samples and activated using CD3/CD28 beads. 4 days after activation cells were transfected with mRNAs encoding different CAR molecules (using PulseAgile electroporation) and degranulation activity was assessed 24h after transfection.

Figure 4:
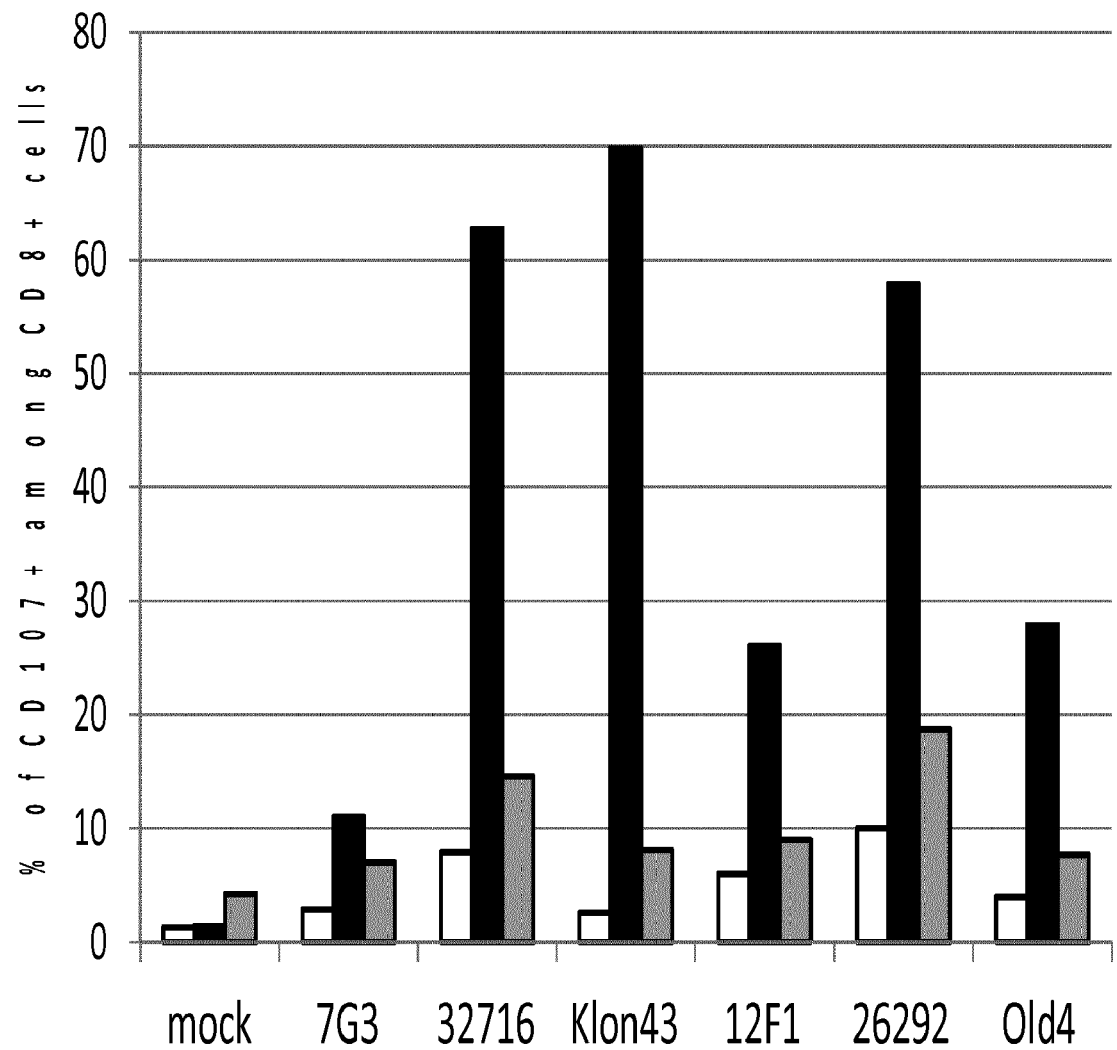
FIG. 4: shows degranulation activity in percentage (%) of degranulation of the 6 different scFv's for one single architecture (v3: CD8-hinge/CD8-transmembrane), when CAR+ T-cells were co-cultured for 6 hours with CD123 expressing cells (RPM18226), or with cells that do not express CD123 (K562). White bars correspond to degranulation signals observed in T-cells that were cultured alone, black bars represent the signals observed when T-cells were co-cultured with RPM18226 cells, and gray bars show degranulation signals of T-cells co-cultured with K562 cells.
Figure 5:
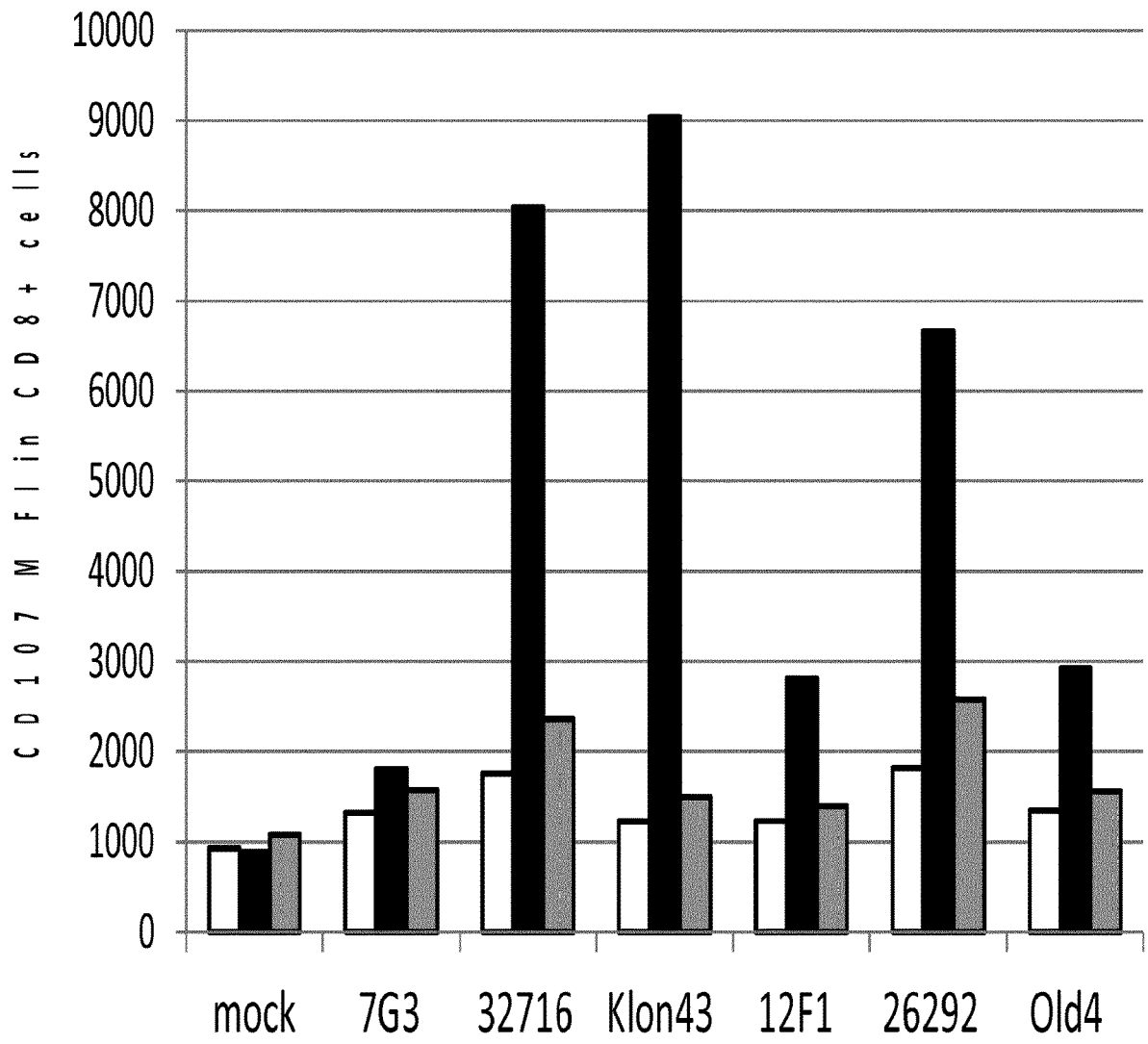
FIG. 5: shows the degranulation activity (CD107a+ cells) in mean fluorescence intensity (MFI) of CAR T-cells after 6h co-cultures with CD123neg cells (K562) or cells expressing high or low levels of CD123 (RPM18226 and KG1a, respectively).

The results illustrated in FIG. 4 and In. FIG. 5 shows degranulation activity of 6 different scFv's for one single architecture (v3: CD8-hinge/CD8-transmembrane), when CAR+ T-cells were co-cultured for 6 hours with CD123 expressing cells (RPM18226), or with cells that do not express CD123 (K562). White bars correspond to degranulation signals observed in T-cells that were cultured alone, black bars represent the signals observed when T-cells were co-cultured with RPM18226 cells, and gray bars show degranulation signals of TI-cells co-cultured with K562 cells.

FIG. 4 shows degranulation activity in percentage (%) of degranulation of the 6 different scFv's for one single architecture (v3: CD8-hinge/CD8-transmembrane), when CAR+ T-cells were co-cultured for 6 hours with CD123 expressing cells (RPM18226), or with cells that do not express CD123 (K562), FIG. 5 shows the degranulation activity (CD107a+ cells) in mean fluorescence activity (MFI) of CAR T-cells after 6h co-cultures with CD123neg cells (K562) or cells expressing high or low levels of CD123 (RPM18226 and KG1a, respectively). The results represent the mean values of three independent experiments.

Surprisingly, the results show that although 7G3 is an anti-CD123 antibody exhibiting a strong affinity and avidity and in vivo effectiveness (Jin et al., 2009; Cell Stem Cell 5, 31-42), the CD123 CART cells derived from 7G3 were not active in the present experimental settings.

26292-, 32716-, and Klon43-CAR expressing cells exhibited a strong activity as compared to control-mock) with Klon43 CAR expressing cells being the most active.

Interestingly, whereas 26292 CAR expressing cells and 32716 CAR expressing cells were slightly active towards cells that do not express CD123 (K562) (grey bars), the activity of Klon43 towards cells that do not express CD123 was comparable to that of Mock T cells.

Among the CAR molecules generated as illustrated in FIG. 2, 8 of them were selected for further activity tests (FIG. 6, FIG. 7 and FIG. 8).

Construction of CD123 CAR Using Anti-CD123 scFv Antibody Fragments Derived from Klon43, 12F1, 32716, and 26292 and Functional Analysis For this, T-cells were isolated from buffy-coat samples and activated using CD3/CD28 beads. Cells were transiently transfected with mRNAs encoding the different candidates at D11 after activation. CAR activity was assessed by measuring their degranulation capacity, the IFN gamma release, and the cytotoxic activity when co-cultured with cells expressing or not CD123.

FIG. 6 shows the degranulation activity (CD107a+ cells) of CAR T-cells after 6h co-cultures with CD123neg cells (K562) or cells expressing high or low levels of CD123 (RPM18226 and KG1a, respectively). Co-cultures were started 24h after CAR mRNA electroporation. The results represent the mean values of three independent experiments.

FIG. 7 shows the amount of IFN gamma released by T-cells when co-cultured for 24h with cells expressing different levels of CD123 (KG1a or RPM18226), or with cells that do not express CD123 (K562). IFN gamma release from T-cells cultured alone, in the same conditions that the co-cultures, is also shown. The experiments were done for three independent donors, and results from a representative donor are shown here.

FIG. 8 shows the specific cytolytic activity of CAR-T cells. Assays were done 48h after CAR mRNA transfection. T-cells were co-cultured with K562+KG1a or K562+RPM18226 cells for 4 hours. Cellular viability for each of the cell lines was determined at the end of the co-cultured and a specific cell lysis percentage was calculated.

All constructions were active, with Klon 43 V3 CAR and 32716V3 CAR exhibiting the higher activity as compared to control than other CARS.

T-Cell-Transduction

Figure 9:
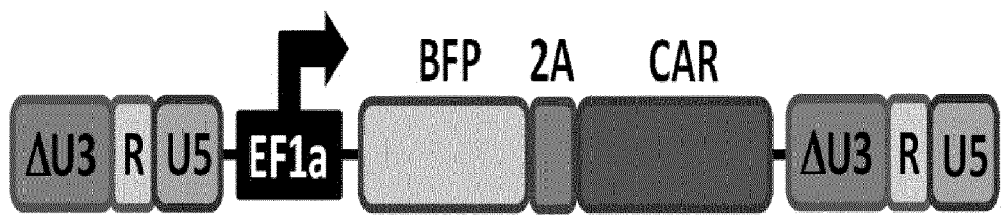
FIG. 9: shows the general construction used for transduction of T cells and the percentage (%) of T cells expressing the CAR or BFP at Day 8 or 10 post transduction for two different donors analyzed by flow cytometry. The CARs correspond to CAR construction klon 43-v3 CAR and 32716-V3 CAR.

Transduction of T-cells with recombinant lentiviral vectors expression the CAR was carried out three days after T-cell purification/activation. Lentiviral vectors were produced by Vectalys SA (Toulouse, France) by transfection of genomic and helper plasmids in HEK-293 cells. Transductions were carried out at a multiplicity of infection of 5, using $10^6$ cells per transduction. CAR detection at the surface of T-cells was done using a recombinant protein consisting on the the fusion of the extracellular domain of the human CD123 protein together with a murine IgG1 Fc fragment (produced by LakePharma). Binding of this protein to the CAR molecule was detected with a PE-conjugated secondary antibody (Jackson Immunoresearch) targeting the mouse Fc portion of the protein, and analyzed by flow cytometry, Two CAR candidates, namely CAR Klon 43 V3 and CAR 32716V3 were then selected and cloned into a lentiviral vector, in which CAR expression is coupled to the BFP through a 2A peptide, and driven by an EF1a promoter. A schematic representation of the lentiviral vector is shown in FIG. 9 upper panel. T-cells were isolated from buffy-coat samples, activated with CD3/CD28 beads, and transduced 3 days after activation with the lentiviral vectors, at an MOI of 5.

CAR detection was done using a fusion protein in which the extracellular domain of the human CD123 protein was fused to a mouse IgG1 derived Fc fragment. Binding of the CAR at the cell surface with the CD123 portion of the fusion protein was detected with anti-Fc PE-conjugated antibody and analyzed by flow cytometry. FIG. 9 represents the % of CAR+ or of Blue fluorescent protein (BFP+) cells (measured by FACS analysis) at Day 8 or 10 post transduction for two different donors.

Figure 10:
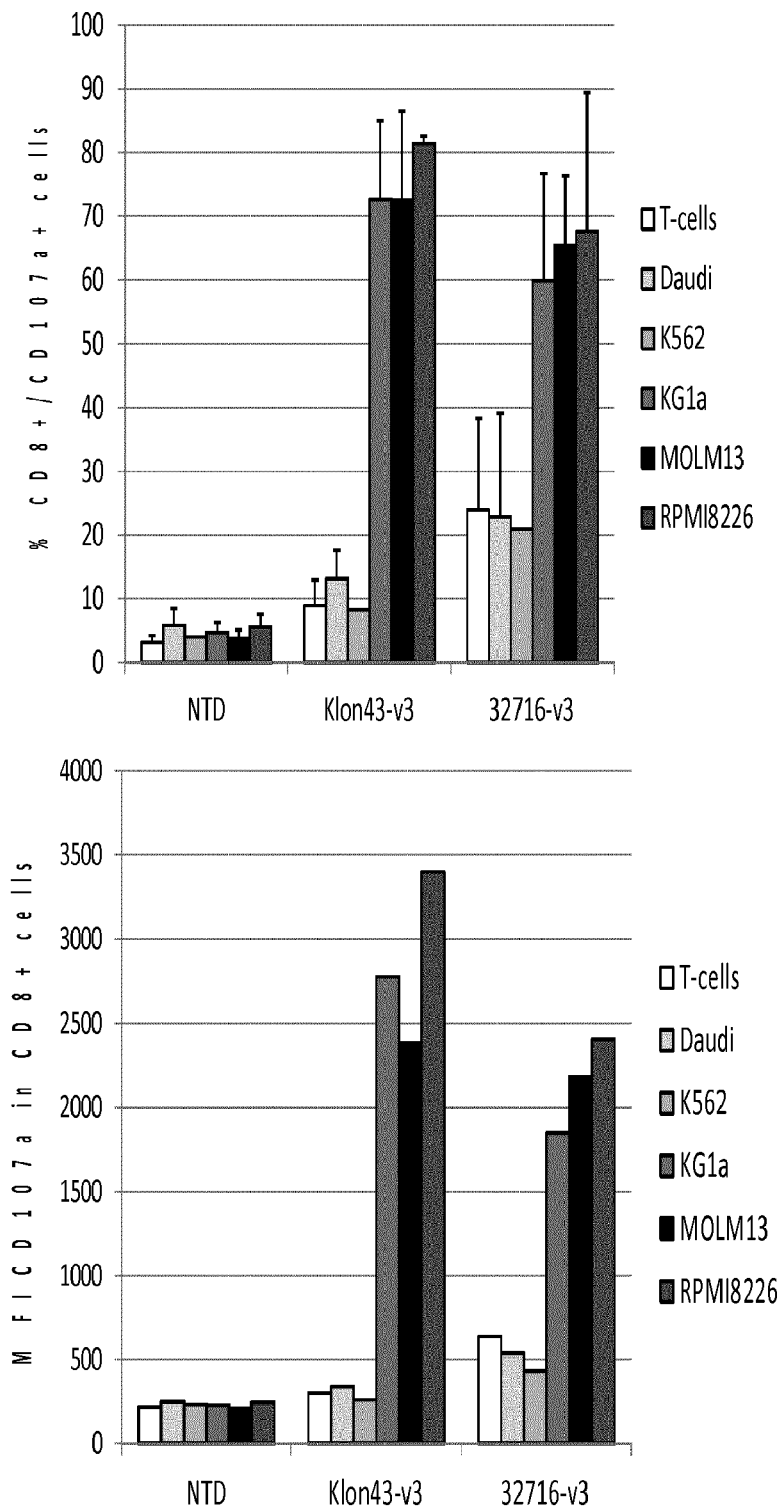
FIG. 10: represents the degranulation activity of T-cells expressing Klon 43-v3 CAR and 32716-V3 CAR, against different cells lines (Daudi and KS62 cells that do not express CD123, KG1a, MOLM13 and RPM18226 that express increasing levels of CD123 (KG1a<MOLM13<RPM18226). The % of CD107a+ cells (among CD8+ cells) for three independent donors is given in the upper panel, and the intensity of CD107a staining is shown in the lower panel for a representative donor. NTD stands for Non Transduced cells.

Activity tests were carried out between D10 and 12 after transduction:

FIG. 10 represents the degranulation activity against different cells lines of transduced cells. Daudi and K562 cells do not express CD123, while KG1a, MOLM13 and RPM18226 express different levels of CD123 (KG1a<MOLM13<RPM18226). The % of CD107a+ cells (among CD8+ cells) for three independent donors is given in the upper panel, and the intensity of CD107a staining is shown in the lower panel for a representative donor. NTD stands for Non Transduced cells.

Figure 11:
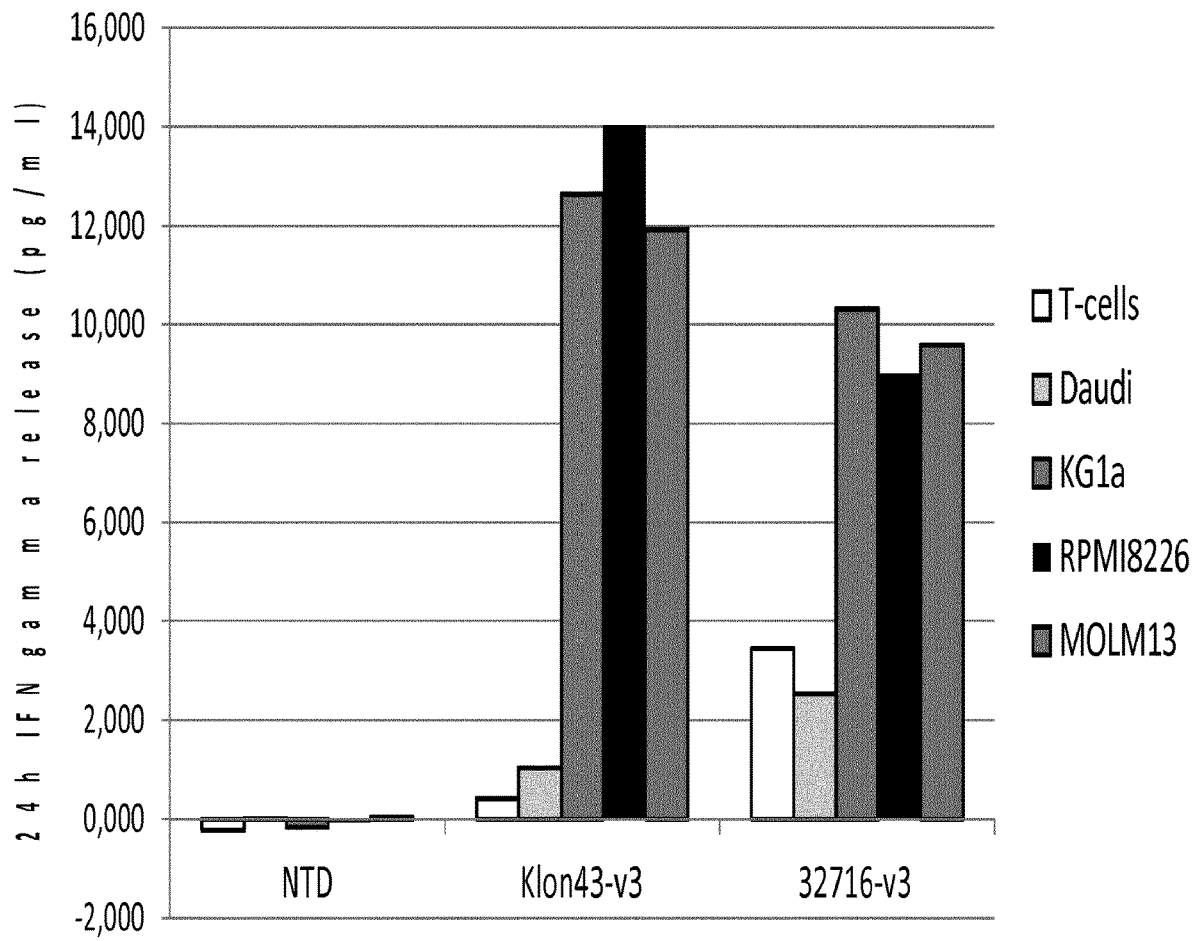
FIG. 11: shows the IFN gamma release upon 24h co-culture of Klon 43-v3 CAR and 32716-V3 CAR expressing T-cells with different cell lines.

Again, the data show that the activity (degranulation FIG. 10 or lysis of CD123+ cells FIG. 11) of the anti-CD123 CAR expressing cells derived from Klon 43 V3 is equivalent to that of 32716V3 (FIG. 10 and FIG. 11).

Most surprisingly, 32716V3-derived CAR expressing cells exhibited a stronger background activity (activity against cells expressing no CD123, DAUDI and K562) than Klon 43 V3 derived CAR expressing cells (FIG. 10 and FIG. 11).

Klon 43 V3 derived CAR expressing cells had a more specific activity and a slightly but significantly higher activity that, 32716V3-derived CAR expressing cells (FIG. 10, FIG. 11 and FIG. 12) in particular toward cells RPM18226 cells that express the higher level of CD123. (see FIG. 13 and FIG. 14)

FIG. 11 shows the IFN gamma release upon 24h co-culture of CAR T-cells with different cell lines.

Figure 12:
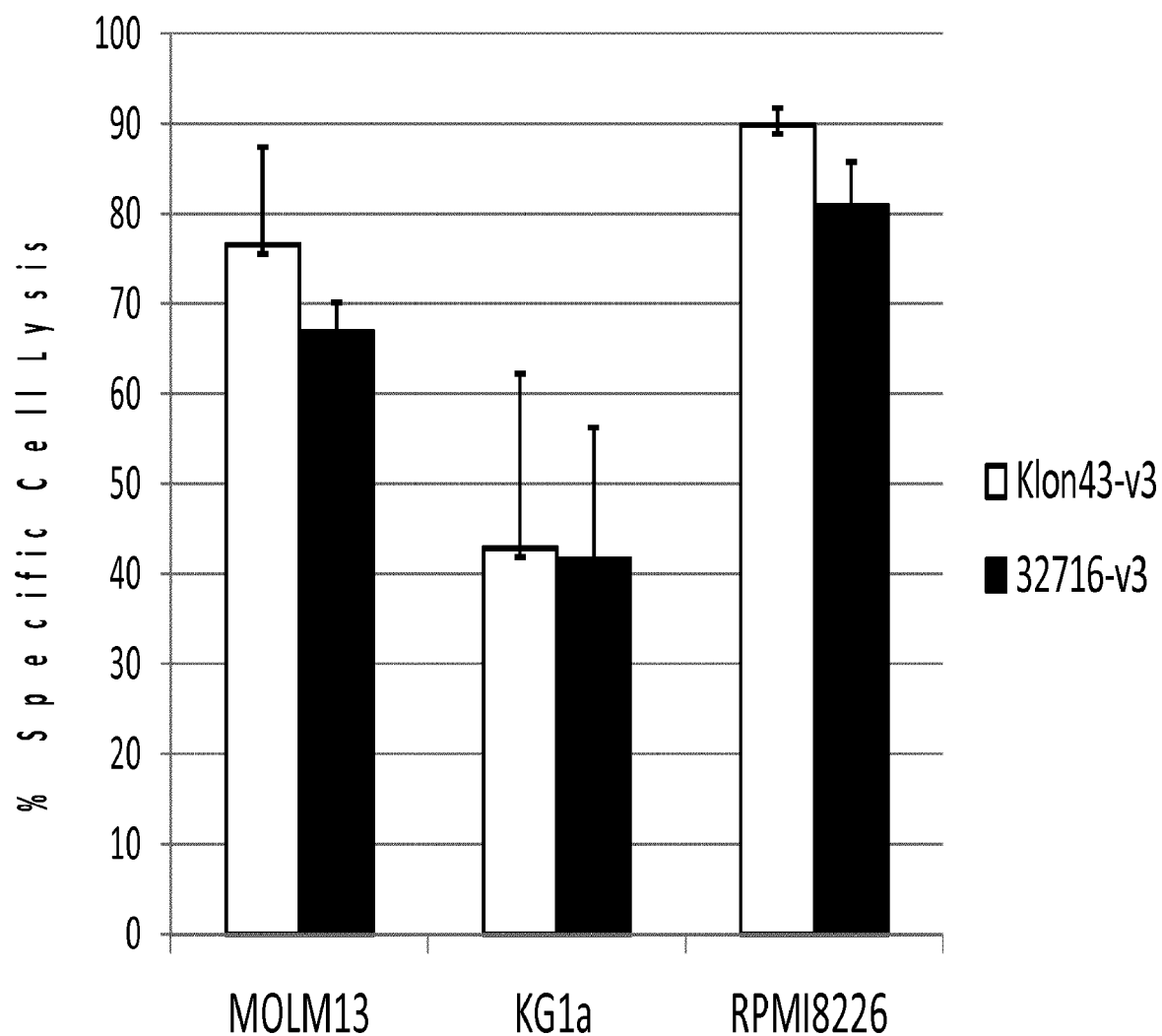
FIG. 12: shows the specific cytolytic activity of klon 43-v3 CAR and 32716-V3 CAR expressing-T cells. A specific cell lysis percentage was calculated. The results represent results obtained in at least two independent donors.

FIG. 12 shows the shows the specific cytolytic activity of CAR-T cells. T-cells were co-cultured with Daudi+KG1a, Daudi+MOLM13, or Daudi+RPM18226 cells for 4 hours. Cellular viability for each of the cell lines was determined at the end of the co-cultured and a specific cell lysis percentage was calculated. The results represent results obtained in at least two independent donors, The results indicate that in T-cells stably expressing the CAR, Klon43-v3 displays a slightly higher activity than 32716-v3 in all the activity tests. In addition, background activity was observed in the degranulation and IFNgamma release assays, when T-cells expressing the 32716-v3 CAR were cultured alone or in the presence of cells that did not express CD123. This was not observed in T-cells expressing the Klon43-v3 CAR. For these reasons, the Klon43-v3 CAR was selected to carry out antitumor in vivo experiments in a mouse model.

Figure 13:
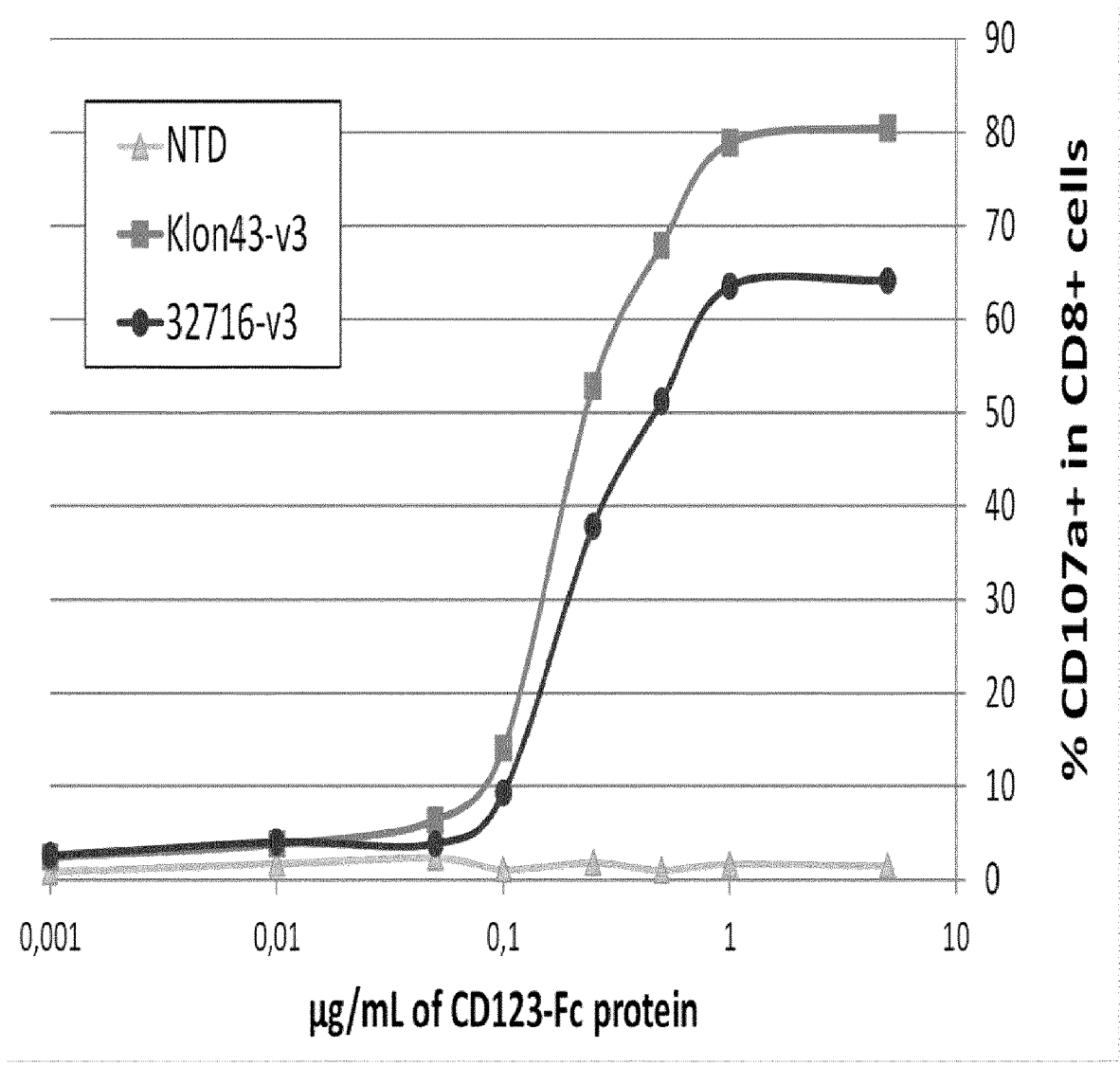
FIG. 13: shows a degranulation activity (in percentage (%) of degranulation) of klon 43-v3 CAR and 32716-V3 CAR expressing-T cells.
Figure 14:
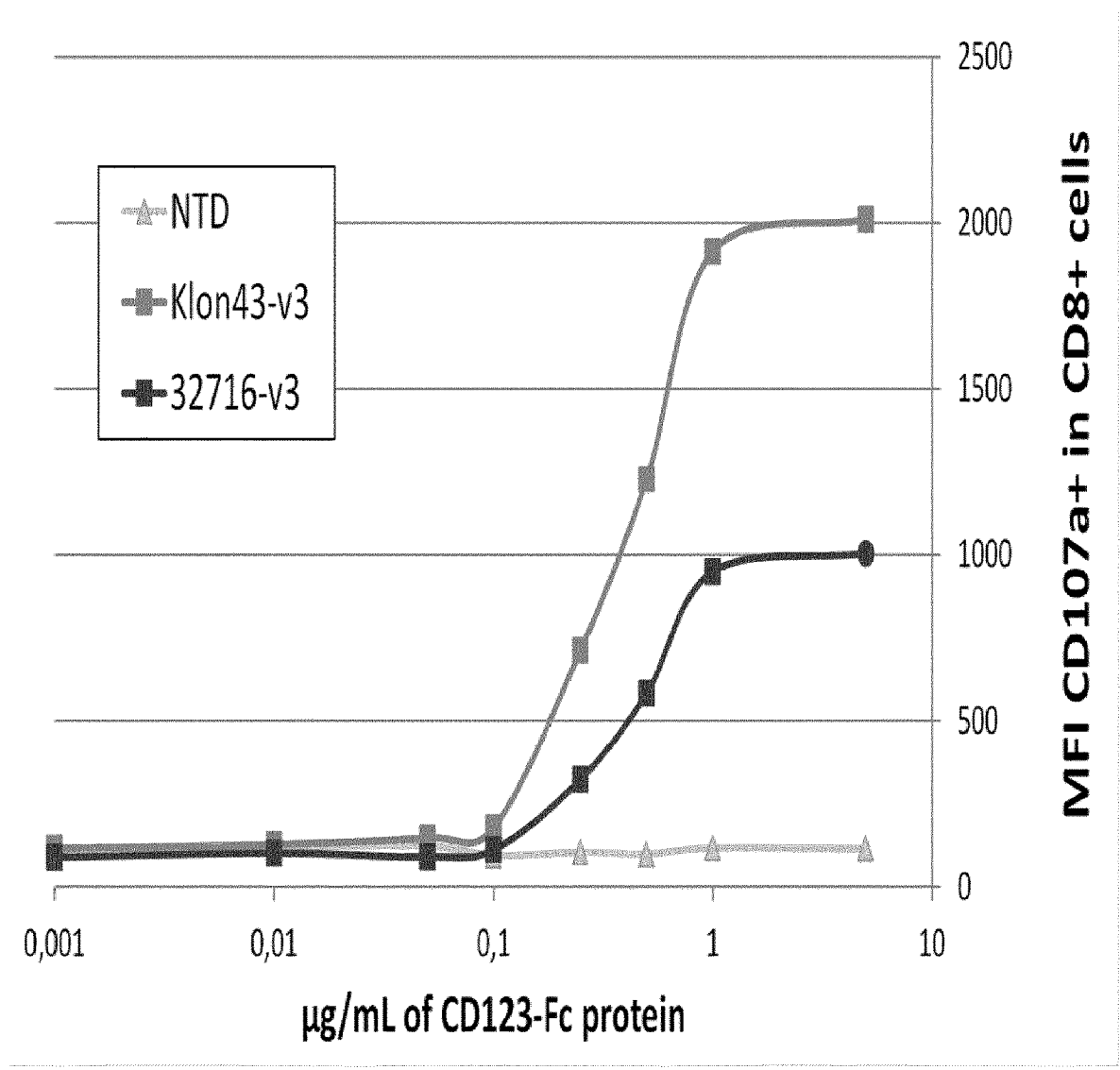
FIG. 14: shows a degranulation activity (in MFI) of Klon 43-v3 CAR and 32716-V3 CAR expressing-T-cells.

FIG. 13 and FIG. 14 shows a dose-response degranulation activity for each of the CAR used. 96-well plates were coated with different doses of CD123-Fc protein (the same used for detection of CAR+ T-cells, see legend in FIG. 5), and cells were cultured for 6h in this plate in the presence of fluorescent CD107a antibody. The results show the degranulation activity (% of CD107a+ cells (FIG. 13) and intensity of CD107a signal (FIG. 14) in CD8+ cells, respectively), Example 3 Anti-Tumor Mouse Model Immunodeficient female NOG mice were intravenously (iv) injected with MOLM13-Luciferase cells as an AML xenograft mouse model. NOG (NOD,Cg-Prkdcscidil2rgtmlSug/JicTac) mice, 6-8 weeks old, were obtained from Taconic (Ry, Danemark) To establish the MOLM13-Luc cell line, MOLM13 cells (DSM2 ACC 554) were transduced with a lentivirus encoding the GFP and the firefly luciferase (amsbio LVP438-PBS). The GFP-positive cells have been selected with Neomycin (ref 10131-027, Gibco, Life Technologies, Saint-Aubin, France). For information, MOLM13 cell line has been established from the peripheral blood of a 20-year-old man with acute myeloid leukemia AML FAB MSa at relapse in 199S after initial myelodysplastic syndromes (MDS, refractory anemia with excess of blasts, RAEB).

Mice were then iv injected (either 2 or 7 days after injection of the tumor cell line) with different doses of CAR+ T-cells (Klon43-v3 CAR), or with T-cells that were not transduced with the CAR lentiviral vector. Bioluminescent signals were determined at the day of T-cell injection (DO) or at D7, 14, 21, 28 and 40 after T-cell injection in order to follow tumoral progression on the different animals.

Animal housing and experimental procedures were carried out by Oncodesign (Dijon, France; http://www.oncodesign.com/), according to the French and European Regulations and NRC Guide for the Care and Use of Laboratory Animals.

Results

Figure 15:
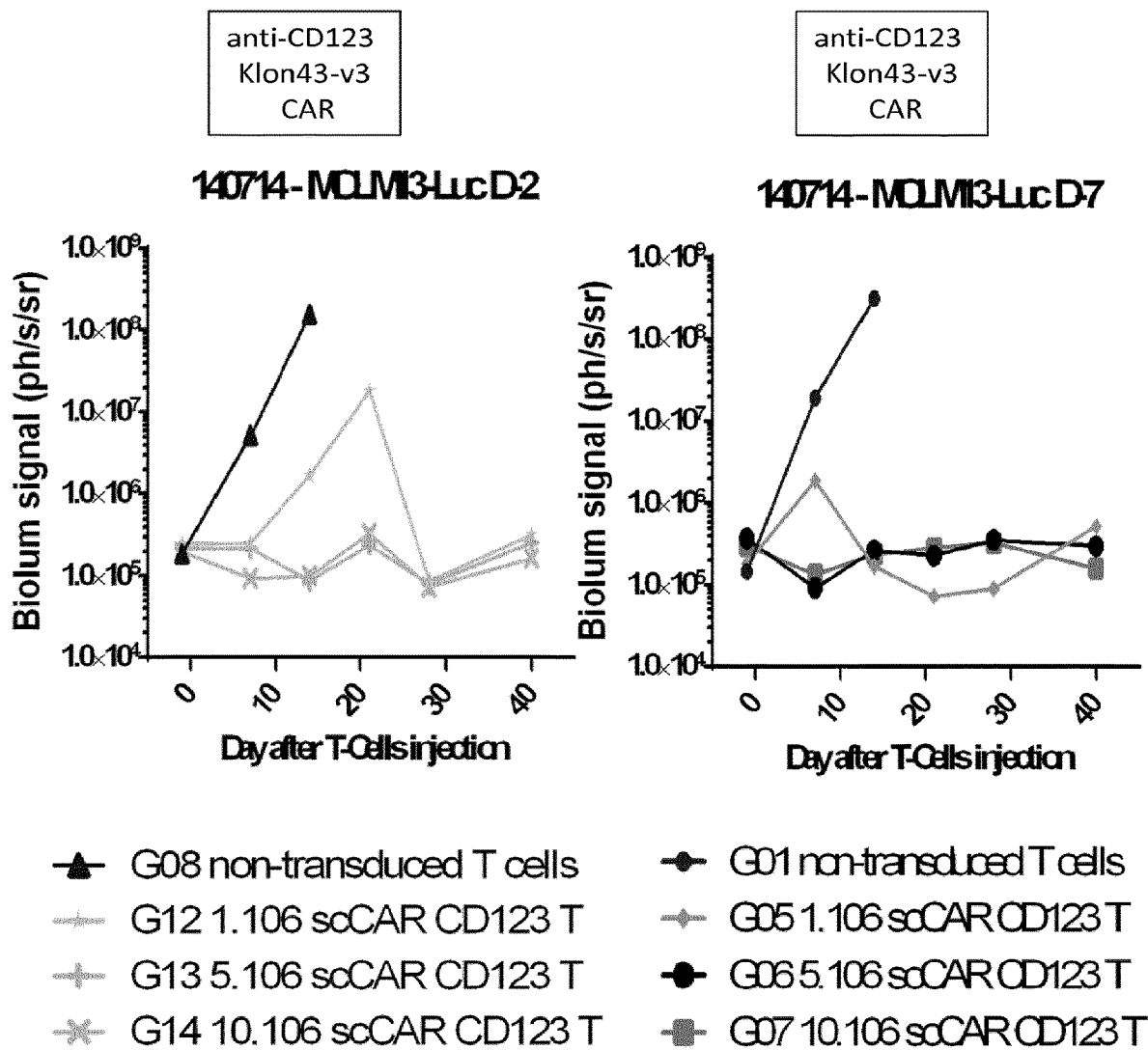
FIG. 15: shows the in vivo activity of T-cells expressing the Klon 43-v3 CAR in NOG Immunodeficient mice. Mice were Injected with MOLM13-Luciferase cells either 2 or 7 days before injection of non-transduced human T-cells, and with different doses of anti-CD123 CAR+ T-cells. The results represent the bioluminescent signal observed at different time points after T-cell injection (mean of 4 mice in each group, except for 612, in which 1 of the 4 mice died between days 21 and 28).

FIG. 15 shows the in vivo activity of T-cells expressing the Klon43-v3 CAR.

immunodeficient mice were injected with MOLM13-Luciferase cells either 2 or 7 days before injection of non-transduced human T-cells, or with different doses of anti-CD123 CAR+ T-cells. The results represent the bioluminescent signal observed at different time points after T-cell injection (mean of 4 mice in each group, except for G12, in which 1 of the 4 mice died between days 21 and 28).

The data show that the object of the present invention can be used against CD123+ cancer cells, for the treatment of CD123+ cancer human leukemia cells.

7G3-1

(SEQ ID NO. 1 + SEQ ID NO. 23)

MALPVTALLLPLALLLHAARP MGWSWIFLFLVSGTGGVLSEVQLQQSGPELVKPGASVKMSCKASGYTF

TDYYMKWVKQSHGKSLEWIGDIIPSNGATFYNQKFKGKATLTVDRSSSTAYMHLNSLTSEDSAVYYCTRS

HLLRASWFAYWGQGTLVTVSAAS GGGGSGGGGSGGGGS MESQTQVLMSLLFWVSGTCGDFVMTQS

PSSLTVTAGEKVTMSCKSSQSLLNSGNQKNYLTWYLQKPGQPPKLLIYWASTRESGVPDRFTGSGSGTDF

TLTISSVQAEDLAVYYCQNDYSYPYTFGGGTKLEIKRGLAVSTISSFFPPGYQIYIWAPLAGTCGVLLLSLVIT

LYCKRGRKKLLYIFKQPFMRPVQTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSEIGMKGERRRGKGHDGLYQG

LSTATKDTYDALHMQALPPR

7G3-2

(SEQ ID NO. 1 + SEQ ID NO. 24)

MALPVTALLLPLALLLHAARPMGWSWIFLFLVSGTGGVLSEVQLQQSGPELVKPGASVKMSCKASGYTF

TDYYMKWVKQSHGKSLEWIGDIIPSNGATFYNQKFKGKATLTVDRSSSTAYMHLNSLTSEDSAVYYCTRS

HLLRASWFAYWGQGTLVTVSAASGGGGSGGGGSGGGGSMESQTQVLMSLLFWVSGTCGDFVMTQS

PSSLTVTAGEKVTMSCKSSQSLLNSGNQKNYLTWYLQKPGQPPKLLIYWASTRESGVPDRFTGSGSGTDF

TLTISSVQAEDLAVYYCQNDYSYPYTFGGGTKLEIKRGLAVSTISSFFPPGYQIISFFLALTSTALLFLLFFLTLR

FSVVKRGRKKLLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRGKGHDGLYQ

GLSTATKDTYDALHMQALPPR

7G3-3

(SEQ ID NO. 1 + SEQ ID NO. 25)

MALPVTALLLPLALLLHAARPMGWSWIFLFLVSGTGGVLSEVQLQQSGPELVKPGASVKMSCKASGYTF

TDYYMKWVKQSHGKSLEWIGDIIPSNGATFYNQKFKGKATLTVDRSSSTAYMHLNSLTSEDSAVYYCTRS

HLLRASWFAYWGQGTLVTVSAASGGGGSGGGGSGGGGSMESQTQVLMSLLFWVSGTCGDFVMTQS

PSSLTVTAGEKVTMSCKSSQSLLNSGNQKNYLTWYLQKPGQPPKLLIYWASTRESGVPDRFTGSGSGTDF

TLTISSVQAEDLAVYYCQNDYSYPYTFGGGTKLEIKRTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

7G3-4

(SEQ ID NO. 1 + SEQ ID NO. 26)

MALPVTALLLPLALLLHAARPMGWSWIFLFLVSGTGGVLSEVQLQQSGPELVKPGASVKMSCKASGYTF

TDYYMKWVKQSHGKSLEWIGDIIPSNGATFYNQKFKGKATLTVDRSSSTAYMHLNSLTSEDSAVYYCTRS

HLLRASWFAYWGQGTLVTVSAASGGGGSGGGGSGGGGSMESQTQVLMSLLFWVSGTCGDFVMTQS

PSSLTVTAGEKVTMSCKSSQSLLNSGNQKNYLTWYLQKPGQPPKLLIYWASTRESGVPDRFTGSGSGTDF

TLTISSVQAEDLAVYYCQNDYSYPYTFGGGTKLEIKRTTTPAPRPPTPAPTIASQPLSLRPEACRPAAGGAV

HTRGLDFACDIISFFLALTSTALLFLLFFLTLRFSVVKRGRKKLLYIFKQPFMRPVQTTQEEDGCSCRFPEEEE

GGCELRVKFSRSADAPAYQQGQNQLYNELNLGRREEYDKRRGRDPEMGGKPRRKNPQEGLYNELQKD

KMAEAYSEIGMKGERRRGKGHDGLYQGLSTATKDTYDALHMQALPPR

7G3-5

(SEQ ID NO. 1 + SEQ ID NO. 27)

MALPVTALLLPLALLLHAARP MGWSWIFLFLVSGTGGVLSEVQLQQSGPELVKPGASVKMSCKASGYTF
TDYYMKWVKQSHGKSLEWIGDIIPSNGATFYNQKFKGKATLTVDRSSSTAYMHLNSLTSEDSAVYYCTRS
HLLRASWFAYWGQGTLVTVSAAS GGGGSGGGGSGGGGS MESQTQVLMSLLFWVSGTCGDFVMTQS
PSSLTVTAGEKVTMSCKSSQSLLNSGNQKNYLTWYLQKPGQPPKLLIYWASTRESGVPDRFTGSGSGTDF
TLTISSVQAEDLAVYYCQNDYSYPYTFGGGTKLEIKR EPKSPDKTHTCPPCPAPPVAGPSVFLFPPKPKDTL
MIARTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGKIYIWAPLAGTCGV
LLLSLVITLYCKRGRKKLLYIFKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMAEAYSEIGMKGERRRGKG
HDGLYQGLSTATKDTYDALHMQALPPR

7G3-6

(SEQ ID NO. 1 + SEQ ID NO. 28)

MALPVTALLLPLALLLHAARP MGWSWIFLFLVSGTGGVLSEVQLQQSGPELVKPGASVKMSCKASGYTF
TDYYMKWVKQSHGKSLEWIGDIIPSNGATFYNQKFKGKATLTVDRSSSTAYMHLNSLTSEDSAVYYCTRS
HLLRASWFAYWGQGTLVTVSAAS GGGGSGGGGSGGGGS MESQTQVLMSLLFWVSGTCGDFVMTQS
PSSLTVTAGEKVTMSCKSSQSLLNSGNQKNYLTWYLQKPGQPPKLLIYWASTRESGVPDRFTGSGSGTDF
TLTISSVQAEDLAVYYCQNDYSYPYTFGGGTKLEIKR EPKSPDKTHTCPPCPAPPVAGPSVFLFPPKPKDTL
MIARTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGKIISFFLALTSTALLFL
LFFLTLRFSVVKRGRKKLLYIFKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMAEAYSEIGMKGERRRGKG
HDGLYQGLSTATKDTYDALHMQALPPR

O1d4-3

(SEQ ID NO. 1 + SEQ ID NO. 29)

MALPVTALLLPLALLLHAARP WTWRFLFVVAAATGVQSQVQLLQSGAEVKKPGSSVKVSCKASGGTFST
YAISWVRQAPGQGLEWMGGIIPIFGIVNYAQKFQGRVTITADESTSTAYMELSSLRSEDTAVYYCARGGG
SGPDVLDIWGQGTMVTVSSAST GGGGSGGGGSGGGGS MDMRVPAQLLGLLLLWLPGARCVIWMTQ
SPSLLSASTGDRVTISCRMSQGIRSYLAWYQQKPGKAPELLIYAASTLQSGVPSRFSGSGSGTDFTLTISSLQ
SEDFATYYCQQYYSFPYTFGQGTKLEIKRTV TTTPAPRPPTPAPTIASQPLSLRPEACRPAAGGAVHTRGLD
FACDIYIWAPLAGTCGVLLLSLVITLYCKRGRKKLLYIFKQPFMRPVQTTQEEDGCSCRFPEEEEGGCELRVK
FSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR

-continued 26292-1
(SEQ ID NO. 1 + SEQ ID NO. 30)
MALPVTALLLPLALLLHAARPQVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGSDVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIKGLAVSTISSFFPPGYQIYIWAP

LAGTCGVLLLSLVITLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGE

RRRGKGHDGLYQGLSTATKDTYDALHMQALPPR 26292-2
(SEQ ID NO. 1 + SEQ ID NO. 31)
MALPVTALLLPLALLLHAARPQVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGSDVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIKGLAVSTISSFFPPGYQIISFFLAL

TSTALLFLLFFLTLRFSVVKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGE

RRRGKGHDGLYQGLSTATKDTYDALHMQALPPR 26292-3
(SEQ ID NO. 1 + SEQ ID NO. 32)
MALPVTALLLPLALLLHAARPQVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGSDVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIKTTTPAPRPPTPAPTIASQPLSL

RPEACRPAAGGAVHTRGLDFACDIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR 26292-4
(SEQ ID NO. 1 + SEQ ID NO. 33)
MALPVTALLLPLALLLHAARPQVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGSDVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIKTTTPAPRPPTPAPTIASQPLSL

RPEACRPAAGGAVHTRGLDFACDIISFFLALTSTALLFLLFFLTLRFSVVKRGRKKLLYIFKQPFMRPVQTTQ

EEDGCSCRFPEEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPPR

-continued 26292-5
(SEQ ID NO. 1 + SEQ ID NO. 34)
MALPVTALLLPLALLLHAARP QVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGS DVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIK EPKSPDKTHTCPPCPAPPVAG

PSVFLFPPKPKDTLMIARTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSLSLSPG

KIYIWAPLAGTCGVLLLSLVITLYCKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGLYNELQKDKMAEAYSEI

GMKGERRRGKGHDGLYQGLSTATKDTYDALHMQALPPR 26292-6
(SEQ ID NO. 1 + SEQ ID NO. 35)
MALPVTALLLPLALLLHAARP QVQLQQPGAELVRPGASVKLSCKASGYTFTSYWMNWVKQRPDQGLE

WIGRIDPYDSETHYNQKFKDKAILTVDKSSSTAYMQLSSLTSEDSAVYYCARGNWDDYWGQGTTLTVSS

GGGGSGGGGSGGGGS DVQITQSPSYLAASPGETITINCRASKSISKDLAWYQEKPGKTNKLLIYSGSTLQS

GIPSRFSGSGSGTDFTLTISSLEPEDFAMYYCQQHNKYPYTFGGGTKLEIK EPKSPDKTHTCPPCPAPPVAG

PSVFLFPPKPKDTLMIARTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSLSLSPG

KIISFFLALTSTALLFLLFFLTLRFSVVKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR 32716-1
(SEQ ID NO. 1 + SEQ ID NO. 36)
MALPVTALLLPLALLLHAARP QIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGS DIVLTQSPASLAVSLGQRATISCRASESVDNYGNTFMHWYQQKPGQPPKLLIY

RASNLESGIPARFSGSGSRTDFTLTINPVEADDVATYYCQQSNEDPPTFGAGTKLELK GLAVSTISSFFPPG

YQIYIWAPLAGTCGVLLLSLVITLYCKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR 32716-2
(SEQ ID NO. 1 + SEQ ID NO. 37)
MALPVTALLLPLALLLHAARP QIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGS DIVLTQSPASLAVSLGQRATISCRASESVDNYGNTFMHWYQQKPGQPPKLLIY

-continued

RASNLESGIPARFSGSGSRTDFTLTINPVEADDVATYYCQQSNEDPPTFGAGTKLELKGLAVSTISSFFPPG

YQIISFFLALTSTALLFLLFFLTLRFSVVKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRKNPQEGLYNELQKDKMAEAY

SEIGMKGERRRGKGHDGLYQGLSTATKDTYDALHMQALPPR 32716-3
(SEQ ID NO. 1 + SEQ ID NO. 38)
MALPVTALLLPLALLLHAARPQIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGSDIVLTQSPASLAVSLGQRATISCRASESVDNYGNTFMHWYQQKPGQPPKLLIY

RASNLESGIPARFSGSGSRTDFTLTINPVEADDVATYYCQQSNEDPPTFGAGTKLELKTTTPAPRPPTPAPT

IASQPLSLRPEACRPAAGGAVHTRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPP

R 32716-4
(SEQ ID NO. 1 + SEQ ID NO. 39)
MALPVTALLLPLALLLHAARPQIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGSDIVLTQSPASLAVSLGQRATISCRASESVDNYGNTFMHWYQQKPGQPPKLLIY

RASNLESGIPARFSGSGSRTDFTLTINPVEADDVATYYCQQSNEDPPTFGAGTKLELKTTTPAPRPPTPAPT

IASQPLSLRPEACRPAAGGAVHTRGLDFACDIISFFLALTSTALLFLLFFLTLRFSVVKRGRKKLLYIFKQPFMR

PVQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPP

R 32716-5
(SEQ ID NO. 1 + SEQ ID NO. 40)
MALPVTALLLPLALLLHAARPQIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGSDIVLTQSPASLAVSLGQRATISCRASESVDNYGNTFMHWYQQKPGQPPKLLIY

RASNLESGIPARFSGSGSRTDFTLTINPVEADDVATYYCQQSNEDPPTFGAGTKLELKEPKSPDKTHTCPPC

PAPPPVAGPSVFLFPPKPKDTLMIARTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQ

KSLSLSPGKIYIWAPLAGTCGVLLLSLVITLYCKRGRKKLLYIFKQPFMRPVQTTQEEDGCSCRFPEEEEGGC

ELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPPR

-continued 32716-6
(SEQ ID NO. 1 + SEQ ID NO. 41)
MALPVTALLLPLALLLHAARP QIQLVQSGPELKKPGETVKISCKASGYIFTNYGMNWVKQAPGKSFKWM

GWINTYTGESTYSADFKGRFAFSLETSASTAYLHINDLKNEDTATYFCARSGGYDPMDYWGQGTSVTVSS

GGGGSGGGGSGGGGS DIVLTQSPASLAVSLGQRATISCRASESVDNYGNTFMHWYQQKPGQPPKLLIY

RASNLESGIPARFSGSGSRTDFTLTINPVEADDVATYYCQQSNEDPPTFGAGTKLELK EPKSPDKTHTCPPC

PAPPVAGPSVFLFPPKPKDTLMIARTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQ

KSLSLSPGKIISFFLALTSTALLFLLFFLTLRFSVVKRGRKKLLYIFKQPFMRPVQTTEEDGCSCRFPEEEEGG

CELRVKFSRSADAPAYQQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

Klo43-1
(SEQ ID NO. 1 + SEQ ID NO. 42)
MALPVTALLLPLALLLHAARP EVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSS GGGGSGGGGSGGGGS MADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

R GLAVSTISSFFPPGYQIYIWAPLAGTCGVLLLSLVITLYCKRGRKKLLYIFKQPFMRPVQTTQEEDGCSCRF

PEEEEGGCELRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

Klo43-2
(SEQ ID NO. 1 + SEQ ID NO. 43)
MALPVTALLLPLALLLHAARP EVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSS GGGGSGGGGSGGGGS MADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

R GLAVSTISSFFPPGYQIISFFLALTSTALLFLLFFLTLRFSVVKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

Klo43-3
(SEQ ID NO. 1 + SEQ ID NO. 44)
MALPVTALLLPLALLLHAARP EVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSS GGGGSGGGGSGGGGS MADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

R TTTPAPRPPTPAPTIASQPLSLRPEACRPAAGGAVHTRGLDFACDIYIWAPLAGTCGVLLLSLVITLYCKR

GRKKLLYIFKQPFMRPVQTTQEEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGERRRGKGHDGLYQGLSTAT

KDTYDALHMQALPPR

Klo43-4

(SEQ ID NO. 1 + SEQ ID NO. 45)

MALPVTALLLPLALLLHAARPEVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSSGGGGSGGGGSGGGGSMADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

RTTTPAPRPPTPAPTIASQPLSLRPEACRPAAGGAVHTRGLDFACDIISFFLALTSTALLFLLFFLTLRFSVVKR

GRKKLLYIFKQPFMRPVQTTQEEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGERRRGKGHDGLYQGLSTAT

KDTYDALHMQALPPR

Klo43-5

(SEQ ID NO. 1 + SEQ ID NO. 46)

MALPVTALLLPLALLLHAARPEVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSSGGGGSGGGGSGGGGSMADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

REPKSPDKTHTCPPCPAPPVAGPSVFLFPPKPKDTLMIARTPEVTCVVVDVSHEDPEVKFNWYVDGVEV

HNAKTKPREEQYNSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDKSRWQQGNVFSC

SVMHEALHNHYTQKSLSLSPGKIYIWAPLAGTCGVLLLSLVITLYCKRGRKKLLYIFKQPFMRPVQTTQEED

GCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

Klo43-6

(SEQ ID NO. 1 + SEQ ID NO. 47)

MALPVTALLLPLALLLHAARPEVKLVESGGGLVQPGGSLSLSCAASGFTFTDYYMSWVRQPPGKALEWL

ALIRSKADGYTTEYSASVKGRFTLSRDDSQSILYLQMNALRPEDSATYYCARDAAYYSYYSPEGAMDYWG

QGTSVTVSSGGGGSGGGGSGGGGSMADYKDIVMTQSHKFMSTSVGDRVNITCKASQNVDSAVAWY

QQKPGQSPKALIYSASYRYSGVPDRFTGRGSGTDFTLTISSVQAEDLAVYYCQQYYSTPWTFGGGTKLEIK

REPKSPDKTHTCPPCPAPPVAGPSVFLFPPKPKDTLMIARTPEVTCVVVDVSHEDPEVKFNWYVDGVEV

HNAKTKPREEQYNSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDKSRWQQGNVFSC

SVMHEALHNHYTQKSLSLSPGKIISFFLALTSTALLFLLFFLTLRFSVVKRGRKKLLYIFKQPFMRPVQTTQEE

DGCSCRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

12F1-3

(SEQ ID NO. 1 + SEQ ID NO. 48)

MALPVTALLLPLALLLHAARP|VQLQESGPGLVKPSQSLSLTCSVTDYSITSGYYWNWIRQFPGNKLEWMG

YISYDGSNNYNPSLKNRISITRDTSKNQFFLKLSSVTTEDTATYYCSRGEGFYFDSWGQGTTLTVSSARS|GG

GGSGGGGSGGGGS|DIMMSQSPSSLAVSVGEKFTMTCKSSQSLFFGSTQKNYLAWYQQKPGQSPKLLIY

WASTRESGVPDRFTGSGSGTDFTLAISSVMPEDLAVYYCQQYYNYPWTFGGGTKLEIK|TTTPAPRPPTPA

PTIASQPLSLRPEACRPAAGGAVHTRGLDFACDIYIWAPLAGTCGVLLLSLVITLYCKRGRKKLLYIFKQPFM

RPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRGKGHDGLYQGLSTATKDTYDALHMQALP

PR

The invention claimed is:

1. An ex vivo method of engineering a T cell suitable for an allogenic immunotherapy treatment of a pre-malignant or malignant cancer condition characterized by CD123-expressing cells, the method comprising:
(a) providing a T cell;
(b) inactivating at least one gene encoding one or more components of a T-cell receptor (TCR) in the T cell;
(c) introducing into the T cell at least one polynucleotide encoding a CD123 specific chimeric antigen receptor (CAR) to be expressed at the surface of the cell;
wherein the CD123 specific CAR comprises an extracellular ligand binding domain comprising a heavy chain variable region ($V_H$) and a light chain variable region ($V_L$) from a monoclonal anti-CD123 antibody, wherein the $V_H$ region comprises CDR sequences set forth in SEQ ID NOs: 67, 68, and 69, and wherein the $V_L$ region comprises CDR sequences set forth in SEQ ID NOs: 70, 71, and 72; an FcγRIIIα, CD8a, or IgG1 hinge; a CD8α transmembrane domain; and a cytoplasmic domain comprising a CD3-ζ signaling domain and a co-stimulatory domain from 4-1BB.

2. The method of claim 1, wherein the $V_H$ region has at least 80% sequence identity with SEQ ID NO: 20, and the $V_L$ region has at least 80% sequence identity with SEQ ID NO: 19.

3. The method of claim 1, wherein the $V_H$ region has a polypeptide sequence selected from SEQ ID NOs: 60, 61, 62, 63, 64, and 65; and the $V_L$ region has a polypeptide sequence selected from SEQ ID NOs: 54, 55, 56, 57, 58, and 59.

4. The method of claim 1, wherein the CD123 CAR has at least 80% sequence identity with SEQ ID NO: 42, SEQ ID NO: 44, or SEQ ID NO: 46.

5. The method of claim 1, wherein the CD123 CAR comprises a CD8α hinge and has at least 80% sequence identity with SEQ ID NO: 44.

6. The method of claim 1, wherein the at least one gene encoding one or more TCR components is a gene encoding TCR alpha or a gene encoding TCR beta.

7. The method of claim 1, wherein the inactivation of the at least one gene encoding one or more TCR components in step (b) comprises expression of a rare-cutting endonuclease capable of disrupting the at least one gene encoding one or more TCR components.

8. The method according to claim 7, wherein the rare-cutting endonuclease is a TALE-nuclease.

9. The method of claim 7, wherein the rare-cutting endonuclease is encoded by mRNAs introduced into the T cell by electroporation.

10. The method of claim 1, wherein the inactivation of the at least one gene encoding one or more TCR components in step (b) is at a genomic locus comprising the target sequence set forth in SEQ ID NO: 49.

11. The method of claim/6, wherein expression of at least one major histocompatibility complex (MHC) protein is suppressed in the T cell.

12. The method of claim 11, wherein the at least one MHC protein is β-2-microglobulin (02m) or human leukocyte antigen (HLA).

13. The method of claim 1, wherein expression of at least one gene encoding an immune checkpoint protein is reduced or suppressed in the T cell, wherein the checkpoint protein is selected from the group consisting of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF1OB, TNFRSF1OA, CASP8, CASP10, CASP3, CASP6, CASP7, FADD, FAS, TGFBRII, TGFBRI, SMAD2, SMAD3, SMAD4, SMAD10, SKI, SKIL, TGIF1, IL1ORA, IL1ORB, HMOX2, IL6R, IL6ST, CSK, PAG1, SIT1, FOXP3, PRDM1_(or blimp1), BATF, GUCY1A2, GUCY1A3, GUCY1B2, and GUCY1B3.

14. The method of claim 13, wherein the immune checkpoint protein is PDCD1.

15. The method of claim 1, further comprising introducing at least one additional CAR that is not specific for CD123.

16. The method of claim 1, wherein the T cell is obtained from a donor.

17. An engineered T cell expressing at its cell surface membrane the CD123 specific CAR produced by the method of claim 1, wherein at least one gene encoding one or more components of a T-cell receptor (TCR) is inactivated in the T cell.

18. The engineered T cell of claim 17, wherein the at least one gene encoding one or more TCR components is a gene encoding TCR alpha or a gene encoding TCR beta.

19. A method of administering allogenic immunotherapy treatment to a subject in need thereof, the method comprising administering the engineered T cell of claim 17.

20. The method of claim 19, wherein:
(i) the subject has been diagnosed with leukemia, wherein the leukemia is selected from the group consisting of acute myelogenous leukemia, chronic myelogenous leukemia, myelodysplastic syndrome, acute lymphoid leukemia, chronic lymphoid leukemia, and myelodysplastic syndrome; or
(ii) the subject has been diagnosed with lymphoma, wherein the lymphoma is selected from the group consisting of multiple myeloma, non-Hodgkin's lymphoma, Burkitt's lymphoma, and follicular lymphoma.

21. The engineered T cell of claim 17, wherein said cell is mutated to confer resistance to at least one immune suppressive drug, chemotherapy drug, or anti-cancer drug.

* * * * *

UNITED STATES PATENT AND TRADEMARK OFFICE
CERTIFICATE OF CORRECTION

PATENT NO. : 11,919,961 B2
APPLICATION NO. : 17/124971
DATED : March 5, 2024
INVENTOR(S) : Roman Galetto Page 1 of 1

It is certified that error appears in the above-identified patent and that said Letters Patent is hereby corrected as shown below:

In the Claims

In Claim 1, Column 235, Line 41:
"CD8a"
Should read as:
--CD8α--

In Claim 12, Column 236, Line 36:
Delete the occurrence of "(02m)"

In Claim 13, Column 236, Line 48 appears as:
"PRDM1_(or blimp1)"
Should read as:
--PRDM1 (or blimp1)--

In Claim 20, Column 237, Lines 6-7 read:
"leukemia, chronic lymphoid leukemia, and myelodysplastic syndrome; or"
Whereas they should read:
--leukemia, and chronic lymphoid leukemia, or--

Signed and Sealed this
Fourth Day of June, 2024

Katherine Kelly Vidal
*Director of the United States Patent and Trademark Office*